United States Patent
Horiuchi et al.

(10) Patent No.: US 9,917,264 B2
(45) Date of Patent: Mar. 13, 2018

(54) ORGANOMETALLIC COMPLEX AND ORGANIC LIGHT-EMITTING ELEMENT USING THE COMPLEX

(71) Applicant: CANON KABUSHIKI KAISHA, Tokyo (JP)

(72) Inventors: Takayuki Horiuchi, Tokyo (JP); Kengo Kishino, Tokyo (JP); Hirokazu Miyashita, Tokyo (JP); Yosuke Nishide, Kawasaki (JP); Tetsuya Kosuge, Yokohama (JP); Naoki Yamada, Inagi (JP); Jun Kamatani, Tokyo (JP); Akihito Saitoh, Gotemba (JP); Shigemoto Abe, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 12 days.

(21) Appl. No.: 14/761,049

(22) PCT Filed: Jan. 20, 2014

(86) PCT No.: PCT/JP2014/051597
§ 371 (c)(1),
(2) Date: Jul. 15, 2015

(87) PCT Pub. No.: WO2014/112657
PCT Pub. Date: Jul. 24, 2014

(65) Prior Publication Data
US 2015/0364701 A1 Dec. 17, 2015

(30) Foreign Application Priority Data

Jan. 21, 2013 (JP) .................................. 2013-008463

(51) Int. Cl.
*C09K 11/06* (2006.01)
*H05B 33/08* (2006.01)
(Continued)

(52) U.S. Cl.
CPC ...... *H01L 51/0085* (2013.01); *C07F 15/0033* (2013.01); *C09B 57/00* (2013.01);
(Continued)

(58) Field of Classification Search
CPC ........... H01L 2251/552; H01L 51/5024; H01L 51/5004; H01L 51/0054; H01L 51/0074;
(Continued)

(56) References Cited

U.S. PATENT DOCUMENTS 6,824,894 B2  11/2004  Takiguchi et al.
7,078,115 B2   7/2006  Takiguchi et al.
(Continued)

FOREIGN PATENT DOCUMENTS

JP   2009-84256 A    4/2009
JP   2009-114137 A   5/2009
(Continued)

OTHER PUBLICATIONS

Pending U.S. Appl. No. 14/758,683, filed Jun. 30, 2015.
(Continued)

*Primary Examiner* — Daniel R Carcanague
(74) *Attorney, Agent, or Firm* — Fitzpatrick, Cella, Harper & Scinto

(57) ABSTRACT

Provided is an organic light-emitting element having high light-emitting efficiency and a long element lifetime, the organic light-emitting element including an anode, a cathode, and an organic compound layer placed between the anode and the cathode, in which: the organic compound layer includes an emission layer; the emission layer includes a host and a guest; the host is an aromatic hydrocarbon compound; the guest is an iridium complex of a specific structure; and a content of the host is 50 wt % or more with reference to the total amount of the constituent materials for the emission layer.

23 Claims, 1 Drawing Sheet

(51) Int. Cl.

| | | |
|---|---|---|
| *C07F 15/00* | (2006.01) | |
| *H01L 27/32* | (2006.01) | |
| *H01L 51/00* | (2006.01) | |
| *H01L 51/50* | (2006.01) | |
| *H05B 33/14* | (2006.01) | |
| *C09B 57/00* | (2006.01) | |
| *C09B 57/10* | (2006.01) | |

(52) U.S. Cl.
CPC ............ *C09B 57/10* (2013.01); *C09K 11/06* (2013.01); *H01L 27/322* (2013.01); *H01L 27/3244* (2013.01); *H01L 51/0052* (2013.01); *H01L 51/0054* (2013.01); *H01L 51/0055* (2013.01); *H01L 51/0058* (2013.01); *H01L 51/5004* (2013.01); *H05B 33/0896* (2013.01); *H05B 33/14* (2013.01); *C09K 2211/1007* (2013.01); *C09K 2211/1011* (2013.01); *C09K 2211/1029* (2013.01); *C09K 2211/1088* (2013.01); *C09K 2211/1092* (2013.01); *C09K 2211/185* (2013.01); *H01L 51/006* (2013.01); *H01L 51/0056* (2013.01); *H01L 51/0057* (2013.01); *H01L 51/0059* (2013.01); *H01L 51/0061* (2013.01); *H01L 51/0072* (2013.01); *H01L 51/0073* (2013.01); *H01L 51/0074* (2013.01); *H01L 51/0081* (2013.01); *H01L 51/0092* (2013.01); *H01L 51/5016* (2013.01); *H01L 51/5024* (2013.01); *H01L 2251/552* (2013.01)

(58) Field of Classification Search
CPC ............ H01L 51/0052; H01L 51/0056; H01L 51/0073; H01L 51/0061; H01L 51/0057; H01L 51/006; H01L 51/0072; H01L 51/0059; H01L 51/0092; H01L 51/0055; H01L 51/0081; C09K 2211/1007; C09K 2211/1088; C09K 2211/1011; C07F 15/0033
USPC ............................................................ 546/1
See application file for complete search history.

(56) References Cited

U.S. PATENT DOCUMENTS

| | | | |
|---|---|---|---|
| 7,232,618 B2 | 6/2007 | Yamada et al. | |
| 7,976,958 B2 | 7/2011 | Takiguchi et al. | |
| 8,084,937 B2 | 12/2011 | Kosuge et al. | |
| 8,268,455 B2 | 9/2012 | Kamatani et al. | |
| 8,330,153 B2 | 12/2012 | Ooishi et al. | |
| 8,367,223 B2 | 2/2013 | Xia et al. | |
| 8,519,384 B2 | 8/2013 | Xia et al. | |
| 9,466,804 B2* | 10/2016 | Kish Ino; Kengo ... | C09K 11/06 |
| 2007/0231601 A1 | 10/2007 | Nakasu et al. | |
| 2007/0278936 A1 | 12/2007 | Herron et al. | |
| 2008/0210930 A1 | 9/2008 | Kamatani et al. | |
| 2008/0269491 A1 | 10/2008 | Jabbour et al. | |
| 2009/0039776 A1 | 2/2009 | Yamada et al. | |
| 2009/0091252 A1 | 4/2009 | Kosuge et al. | |
| 2010/0141127 A1 | 6/2010 | Xia et al. | |
| 2010/0219407 A1 | 9/2010 | Kamatani et al. | |
| 2010/0289406 A1 | 11/2010 | Ma et al. | |
| 2011/0227049 A1 | 9/2011 | Xia et al. | |
| 2012/0061657 A1 | 3/2012 | Kosuge et al. | |
| 2013/0323719 A1 | 12/2013 | Cysewski et al. | |
| 2013/0341599 A1 | 12/2013 | Xia et al. | |
| 2014/0021449 A1 | 1/2014 | Xia et al. | |
| 2015/0295188 A1* | 10/2015 | Kosuge ............ | C09K 11/06 345/173 |
| 2015/0303386 A1* | 10/2015 | Kishino ........... | C09K 11/06 257/40 |
| 2015/0333267 A1* | 11/2015 | Kamatani ......... | H01L 51/0054 257/40 |
| 2015/0333279 A1* | 11/2015 | Kamatani ......... | C07F 15/0033 257/40 |
| 2015/0357586 A1* | 12/2015 | Horiuchi .......... | C09K 11/06 257/40 |
| 2015/0357587 A1* | 12/2015 | Kishino ........... | C09K 11/06 257/40 |
| 2015/0364702 A1* | 12/2015 | Abe ................. | C09K 11/06 257/40 |
| 2015/0364703 A1* | 12/2015 | Miyashita ........ | H01L 27/3234 345/204 |
| 2015/0372244 A1* | 12/2015 | Abe ................. | H01L 51/0058 257/40 |
| 2016/0145281 A1 | 5/2016 | Cysewski et al. | |

FOREIGN PATENT DOCUMENTS

| | | |
|---|---|---|
| JP | 2009-539768 A | 11/2009 |
| JP | 2012502046 A | 1/2012 |
| JP | 2012-508258 A | 4/2012 |
| WO | 2006/014599 A2 | 2/2006 |
| WO | 2007/072889 A1 | 6/2007 |
| WO | 2007/143201 A1 | 12/2007 |
| WO | 2009/060995 A1 | 5/2009 |
| WO | 2010/028151 A1 | 3/2010 |
| WO | 2012/107419 A1 | 8/2012 |

OTHER PUBLICATIONS

Pending U.S. Appl. No. 14/648,494, filed May 29, 2015.
Pending U.S. Appl. No. 14/648,095, filed May 28, 2015.
Pending U.S. Appl. No. 14/649,048, filed Jun. 2, 2015.
Pending U.S. Appl. No. 14/760,093, filed Jul. 9, 2015.
Pending U.S. Appl. No. 14/764,204, filed Jul. 29, 2015.
Pending U.S. Appl. No. 14/764,376, filed Jul. 29, 2015.
N. M. Shavaleev, et al., "Bright Blue Phosphorescence from Cationic Bis-Cyclometalated Iridium (III) Isocyanide Complexes," Inorganic Chem., vol. 51, No. 4, pp. 2263-2271 (2012).
Extended European Search Report dated Aug. 2, 2016, in counterpart EP application No. 14741011.2 (5 pages).

* cited by examiner

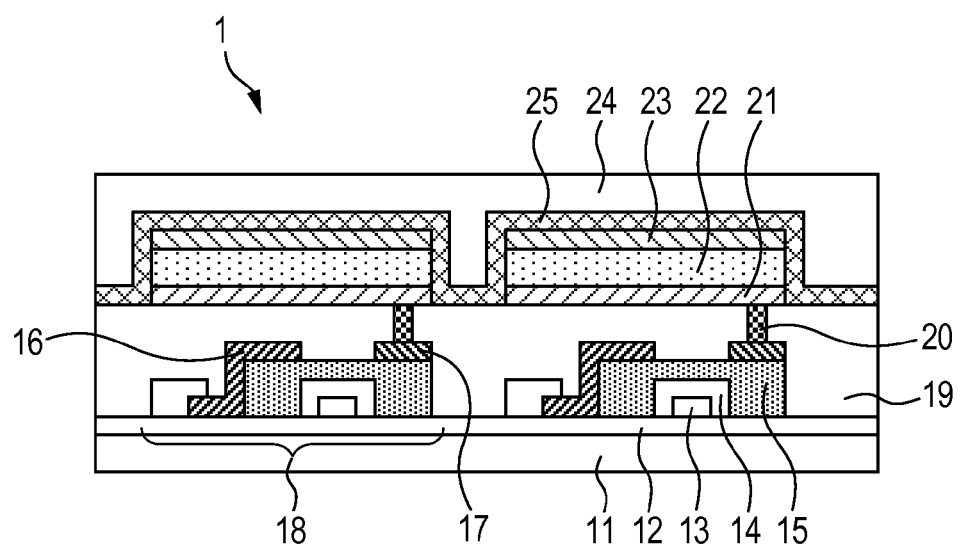

ORGANOMETALLIC COMPLEX AND ORGANIC LIGHT-EMITTING ELEMENT USING THE COMPLEX

TECHNICAL FIELD

The present invention relates to an organometallic complex and an organic light-emitting element using the complex.

BACKGROUND ART

Organic light-emitting elements (organic electroluminescent elements or organic EL elements) are each an electronic element including an anode, a cathode, and an organic compound layer placed between both of these electrodes. A hole and electron injected from both the electrodes recombine in the organic compound layer to produce an exciton, and the organic light-emitting element emits light upon return of the exciton to its ground state. Recent advance of the organic light-emitting elements is significant and the advanced light-emitting elements have, for example, the following features. The elements can be driven at low voltages, emit light beams having various wavelengths, have high-speed responsiveness, and can be reduced in thickness and weight.

Of the organic light-emitting elements, a phosphorescent light-emitting element is an organic light-emitting element that: includes, in its organic compound layer, a material that emits phosphorescence; and provides light emission derived from a triplet exciton of the material that emits phosphorescence. In recent years, creation of a novel phosphorescent light-emitting material has been vigorously performed for providing a high-performance phosphorescent light-emitting element.

For example, a trivalent iridium complex having a metal-carbon bond has been frequently used as a guest material for a phosphorescent light-emitting element because of its high phosphorescence quantum yield. Meanwhile, PTL 1 describes an iridium complex shown below in which three different kinds of bidentate ligands coordinate to iridium.

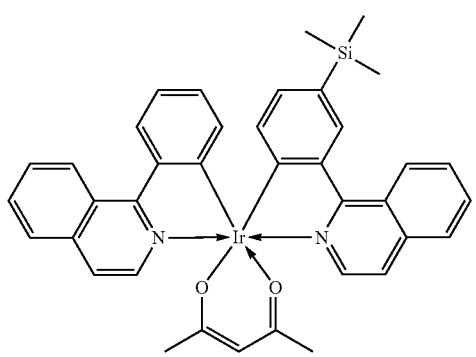

CITATION LIST

Patent Literature

PTL 1: International Publication No. 2007/143201
PTL 2: International Publication No. 2010/028151
PTL 3: International Publication No. 2009/060995
PTL 4: International Publication No. 2006/014599
PTL 5: International Publication No. 2007/072889
PTL 6: Japanese Patent Application Laid-Open No. 2009-84256

Non Patent Literature

NPL 1: Inorganic Chemistry, 2012, vol. 51, No. 4, pp. 2263-2271

SUMMARY OF INVENTION

Solution to Problem

According to one embodiment of the present invention, there is provided an iridium complex, including a compound represented by the following general formula [1].

$$Ir(L_1)(L_2)(L_3) \quad [1]$$

In the general formula [1], $L_1$, $L_2$, and $L_3$ represent bidentate ligands different from one another.

A partial structure $IrL_1$ includes a partial structure represented by the following general formula [2].

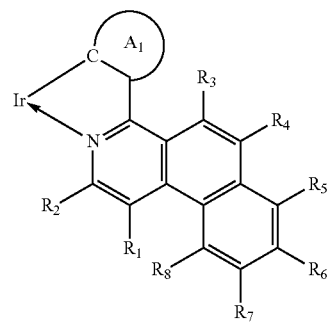

[2]

In the formula [2], a ring $A_1$ represents an aromatic ring or an aromatic heterocycle, and the ring $A_1$ may further have a substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

$R_1$ to $R_8$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group, and may be identical to or different from one another, and when any one of substituents represented by $R_1$ to $R_8$ is an alkyl group having 1 or more and 4 or less carbon atoms, an aralkyl group, an aryl group, a heterocyclic group, a substituted amino group, an alkoxy group, or an aryloxy group, the substituent may further have a substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

In the formula [1], a partial structure $IrL_2$ includes a partial structure represented by the following general formula [3].

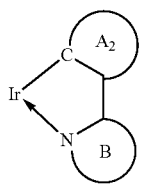

[3]

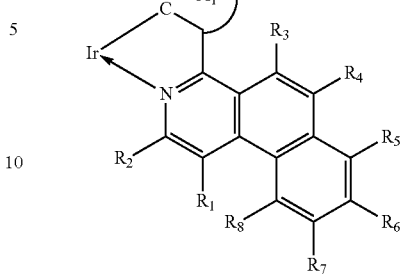

[2]

In the formula [3], a ring $A_2$ represents an aromatic ring or an aromatic heterocycle, and the ring $A_2$ may further have a substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

A ring B represents a nitrogen-containing aromatic heterocycle, and the ring B may further have a substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

$L_3$ represents a monovalent bidentate ligand having a first atom that forms a coordinate bond with iridium and is selected from N, O, S, and P, and a second atom that forms a coordinate bond with iridium and is selected from N, O, S, and P, and the first atom and the second atom may be identical to or different from each other.

Further features of the present invention will become apparent from the following description of exemplary embodiments with reference to the attached drawings.

BRIEF DESCRIPTION OF DRAWINGS

FIG. 1 is a schematic sectional view illustrating an example of a display apparatus including an organic light-emitting element and a TFT element to be connected to the organic light-emitting element.

DESCRIPTION OF EMBODIMENTS

No reference has been made to the sublimability and heat stability of the complex (complex 1) proposed in PTL 1, and hence whether or not its sublimation purification or vacuum deposition can be performed is unclear.

The present invention has been made to solve the problems and an object of the present invention is to provide an organic light-emitting element having high light-emitting efficiency and a long element lifetime.

(1) (Iridium Complex)

Hereinafter, an iridium complex of the present invention is described.

(1-1) Specific Structure of Iridium Complex

The iridium complex of the present invention is a compound represented by the following general formula [1].

Ir(L$_1$)(L$_2$)(L$_3$) [1]

In the general formula [1], $L_1$, $L_2$, and $L_3$ represent bidentate ligands different from one another. Here, a partial structure IrL$_1$ is specifically a partial structure represented by the following general formula [2].

In the general formula [2], a ring $A_1$ represents an aromatic ring or an aromatic heterocycle.

Examples of the aromatic ring represented by the ring $A_1$ include, but, of course, not limited to, a benzene ring, a naphthalene ring, a fluorene ring, a phenanthrene ring, an anthracene ring, a chrysene ring, a triphenylene ring, and a pyrene ring. Of those, a benzene ring, a naphthalene ring, a fluorene ring, or a phenanthrene ring is preferred from the viewpoint of controlling the color of the phosphorescence of the iridium complex to an orange color to a red color.

Examples of the aromatic heterocycle represented by the ring $A_1$ include, but, of course, not limited to, a thiophene ring, a furan ring, an imidazole ring, a pyridine ring, a benzothiophene ring, a benzofuran ring, a quinoline ring, a carbazole ring, a dibenzofuran ring, and a dibenzothiophene ring. Of those, a carbazole ring, a dibenzofuran ring, or a dibenzothiophene ring is preferred from the viewpoint of controlling the color of the phosphorescence of the iridium complex to an orange color to a red color.

It should be noted that in the present invention, the aromatic ring and aromatic heterocycle each represented by the ring $A_1$ may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenehtyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, a pyrenyl group, a dimethylphenyl group, or a difluorophenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, a dibenzothienyl group, or a dimethylpyridyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxyl group such as a phenoxy group; a halogen atom such as a fluorine, chlorine, bromine, or iodine atom; and a cyano group. Here, the alkyl group that the aromatic ring and aromatic heterocycle each represented by the ring $A_1$ may further have also includes an alkyl group in which a hydrogen atom in the substituent is substituted with a fluorine atom.

In the general formula [2], $R_1$ to $R_8$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group.

Examples of the alkyl group represented by any one of $R_1$ to $R_8$ include a methyl group, an ethyl group, an n-propyl group, an isopropyl group, an n-butyl group, a 1-methylpropyl group, a 2-methylpropyl group, and a tert-butyl group.

Examples of the aralkyl group represented by any one of $R_1$ to $R_8$ include a benzyl group and a phenethyl group.

Examples of the aryl group represented by any one of $R_1$ to $R_8$ include a phenyl group, a biphenyl group, a terphenyl group, a naphthyl group, a fluorenyl group, a phenanthrenyl group, an anthracenyl group, a chrysenyl group, a triphenylenyl group, and a pyrenyl group.

Examples of the heterocyclic group represented by any one of $R_1$ to $R_8$ include a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, and a dibenzothienyl group.

Examples of the substituted amino group represented by any one of $R_1$ to $R_8$ include a dimethylamino group, a diethylamino group, a dibenzylamino group, a diphenylamino group, and a ditolylamino group.

Examples of the alkoxy group represented by any one of $R_1$ to $R_8$ include a methoxy group, an ethoxy group, an isopropoxy group, and a tert-butoxy group.

An example of the aryloxy group represented by any one of $R_1$ to $R_8$ is a phenoxy group.

Examples of the halogen atom represented by any one of $R_1$ to $R_8$ include fluorine, chlorine, bromine, and iodine atoms.

Substituents represented by $R_1$ to $R_8$ are each preferably an alkyl group or a phenyl group. This is because an alkyl group and a phenyl group each exhibit an effect of weakening an intermolecular interaction between complex molecules such as π-π stacking. In addition, an intermolecular interaction when alkyl groups or phenyl groups are brought close to each other is weak, and hence an effect of strengthening the intermolecular interaction between the complex molecules is not exhibited. It should be noted that a phenyl group has a small ring plane and hence acts as an alienating group rather than causing the π-π stacking.

It should be noted that upon introduction of alkyl groups as the substituents represented by $R_1$ to $R_8$, the alkyl groups to be introduced are each preferably an alkyl group having 1 or more and 4 or less carbon atoms because the sublimability of the complex itself reduces when the number of carbon atoms is excessively large.

In the general formula [2], $R_1$ to $R_8$ may be identical to or different from one another.

It should be noted that when any one of the substituents represented by $R_1$ to $R_8$ is an alkyl group having 1 or more and 4 or less carbon atoms, an aralkyl group, an aryl group, a heterocyclic group, a substituted amino group, an alkoxy group, or an aryloxy group, the substituent may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, or a pyrenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, or a dibenzothienyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxy group such as a phenoxy group; a halogen atom such as a fluorine, chlorine, bromine, or iodine atom; and a cyano group. Here, the alkyl group that the substituents represented by $R_1$ to $R_8$ may further have also includes an alkyl group in which a hydrogen atom in the substituent is substituted with a fluorine atom.

The partial structure represented by the general formula [2] is preferably a partial structure represented by the following general formula [4].

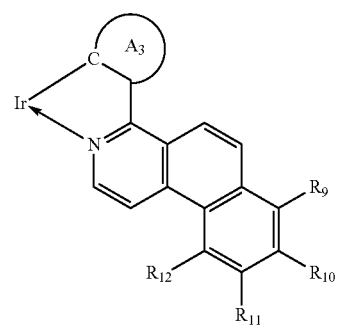

[4]

In the general formula [4], a ring $A_3$ is a ring structure selected from a benzene ring, a naphthalene ring, a fluorene ring, a phenanthrene ring, a carbazole ring, a dibenzofuran ring, and a dibenzothiophene ring.

It should be noted that the ring $A_3$ may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, or a pyrenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, or a dibenzothienyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxy group such as a phenoxy group; a halogen atom such as a fluorine, chlorine, bromine, or iodine atom; and a cyano group.

In the general formula [4], $R_9$ to $R_{12}$ each represent a hydrogen atom, an alkyl group having 1 or more and 4 or less carbon atoms, or a phenyl group, and may be identical to or different from one another.

Specific examples of the alkyl group having 1 or more and 4 or less carbon atoms and phenyl group each represented by any one of $R_9$ to $R_{12}$ are same as the specific examples of $R_1$ to $R_8$ in the general formula [2].

It should be noted that when any one of the substituents represented by $R_9$ to $R_{12}$ is an alkyl group having 1 or more and 4 or less carbon atoms or a phenyl group, the substituent may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, or a pyrenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, or a dibenzothienyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxy group such as a phenoxy group; a halogen atom such as a fluorine, chlorine, bromine, or iodine atom; and a cyano group.

The partial structure represented by the general formula [2] is more preferably a partial structure represented by the following general formula [8]. This is because an organic light-emitting element including, as a guest, an iridium complex having the partial structure represented by the following general formula [8] provides high light-emitting efficiency and a long element lifetime.

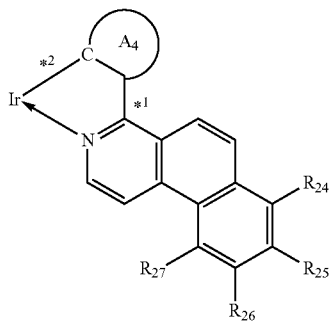

[8]

In the general formula [8], a ring $A_4$ represents any one of the partial structures represented by the following general formulae [9] to [13]. It should be noted that details about the partial structures represented by the following general formulae [9] to [13] are described later.

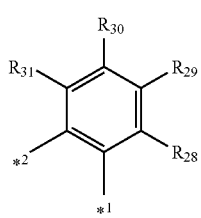

[9]

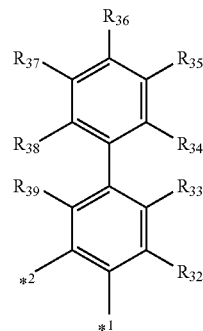

[10]

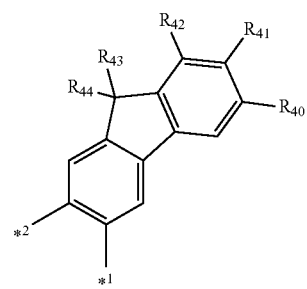

[11]

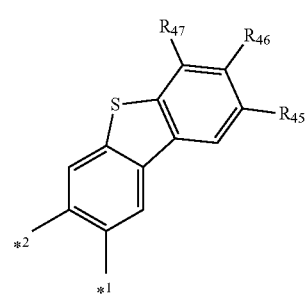

[12]

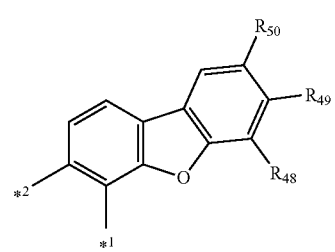

[13]

In the general formula [8], *1 represents a bond between the ring $A_4$ and a benzo[f]isoquinoline skeleton and *2 represents a bond between the ring $A_4$ and an Ir metal.

In the general formula [8], $R_{24}$ to $R_{27}$ each represent a hydrogen atom, an alkyl group having 1 or more and 4 or less carbon atoms, or a phenyl group.

Specific examples of the alkyl group having 1 or more and 4 or less carbon atoms and phenyl group represented by any one of $R_{24}$ to $R_{27}$ are same as the specific examples of $R_1$ to $R_8$ in the general formula [2]. In addition, substituents represented by $R_{24}$ to $R_{27}$ may be identical to or different from one another.

It should be noted that when any one of the substituents represented by $R_{24}$ to $R_{27}$ is an alkyl group having 1 or more and 4 or less carbon atoms or a phenyl group, the corresponding substituent may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, or a pyrenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, or a dibenzothienyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxy group such as a phenoxy group; a halogen atom such as a fluorine, chlorine, bromine, or iodine atom; and a cyano group.

Next, the partial structures represented by the general formulae [9] to [13] are described.

In the general formulae [9] to [13], $R_{28}$ to $R_{50}$ each represent an alkyl group having 1 or more and 4 or less carbon atoms, an aralkyl group, an aryl group, a heterocyclic group, a substituted amino group, an alkoxy group, an aryloxy group, a halogen atom, or a cyano group.

Specific examples of the alkyl group having 1 or more and 4 or less carbon atoms, aralkyl group, aryl group, heterocyclic group, substituted amino group, alkoxy group, aryloxy group, and halogen atom each represented by any one of $R_{28}$ to $R_{50}$ are same as the specific examples of $R_1$ to $R_8$ in the general formula [2]. In addition, substituents represented by $R_{28}$ to $R_{50}$ may be identical to or different from one another.

It should be noted that when any one of the substituents represented by $R_{28}$ to $R_{50}$ is an alkyl group having 1 or more and 4 or less carbon atoms, an aralkyl group, an aryl group, a heterocyclic group, a substituted amino group, an alkoxy group, or an aryloxy group, the corresponding substituent may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, or a pyrenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, or a dibenzothienyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxy group such as a phenoxy group; a halogen atom such as a fluorine, chlorine, bromine, or iodine atom; and a cyano group.

In the general formula [1], a partial structure IrL$_2$ is a partial structure represented by the following general formula [3].

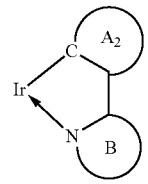

[3]

In the general formula [3], a ring $A_2$ represents an aromatic ring or an aromatic heterocycle. Specific examples of the aromatic ring represented by the ring $A_2$ are the same as the specific examples of the ring $A_1$ in the formula [2]. Of those, a benzene ring, a naphthalene ring, a fluorene ring, a phenanthrene ring, a carbazole ring, a dibenzofuran ring, or a dibenzothiophene ring is preferred because any such ring can form a stable complex with trivalent iridium.

In addition, specific examples of the aromatic heterocycle represented by the ring $A_2$ are the same as the specific examples of the ring $A_1$ in the formula [2]. The aromatic heterocycle is preferably a carbazole ring, a dibenzofuran ring, or a dibenzothiophene ring.

It should be noted that the ring $A_2$ may further have a substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group. Here, specific examples of the alkyl group having 1 or more and 4 or less carbon atoms, the aralkyl group, the aryl group, the heterocyclic group, the substituted amino group, the alkoxy group, the aryloxy group, and the halogen atom each serving as a substituent that the ring $A_2$ may further have are the same as the specific examples in the ring $A_1$ in the formula [2].

In the general formula [3], a ring B represents a nitrogen-containing aromatic heterocycle.

Examples of the nitrogen-containing aromatic heterocycle represented by the ring B include, but, of course, not limited to, a pyridine ring, a pyrimidine ring, a pyrazine ring, a triazine ring, a quinoline ring, an isoquinoline ring, a benzo[f]quinoline ring, a benzo[h]quinoline ring, a benzo[f]isoquinoline ring, a benzo[h]isoquinoline ring, an oxazole ring, a benzo[d]oxazole ring, a benzo[d]thiazole ring, an imidazole ring, and a pyrazole ring. Of those, a pyridine ring, a quinoline ring, a benzo[f]quinoline ring, a benzo[h]quinoline ring, a benzo[f]isoquinoline ring, a benzo[h]isoquinoline ring, an oxazole ring, a benzo[d]oxazole ring, a benzo[d]thiazole ring, or an imidazole ring is preferred because any such heterocycle can form a stable complex with trivalent iridium.

It should be noted that in the general formula [3], the ring B may further have a substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group. Here, specific examples of the alkyl group having 1 or more and 4 or less carbon atoms, the aralkyl group, the aryl group, the heterocyclic group, the substituted amino group, the alkoxy group, the aryloxy group, and the halogen atom each serving as a substituent that the ring B may further have are same as the specific examples in the ring $A_1$ in the formula [2]. It should be noted that upon introduction of the alkyl group as the substituent that the ring B may have, the alkyl group to be introduced is preferably an alkyl group having 1 or more and 4 or less carbon atoms because the sublimability of the complex itself reduces when the number of carbon atoms is excessively large.

The partial structure represented by the following general formula [3] is preferably a partial structure represented by the following general formula [5].

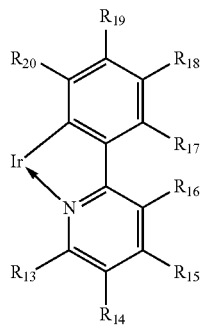

[5]

In the general formula [5], $R_{13}$ to $R_{20}$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group, and may be identical to or different from one another.

It should be noted that specific examples of the alkyl group having 1 or more and 4 or less carbon atoms, aralkyl group, aryl group, heterocyclic group, substituted amino group, alkoxy group, and aryloxy group represented by $R_{13}$ to $R_{20}$ are same as the specific examples of $R_1$ to $R_8$ in the general formula [2]. In addition, when any one of the substituents represented by $R_{13}$ to $R_{20}$ is an alkyl group having 1 or more and 4 or less carbon atoms, an aralkyl group, an aryl group, a heterocyclic group, a substituted amino group, an alkoxy group, or an aryloxy group, the substituent may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, or a pyrenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, or a dibenzothienyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxy group such as a phenoxy group; a halogen atom such as a fluorine, chlorine, bromine, or iodine atom; and a cyano group.

In the general formula [5], $R_{13}$ to $R_{20}$ each preferably represent a hydrogen atom, an alkyl group having 1 or more and 4 or less carbon atoms, or a phenyl group. It should be noted that when any one of the substituents represented by $R_{13}$ to $R_{20}$ is an alkyl group having 1 or more and 4 or less carbon atoms, or a phenyl group, the substituent may further have an alkyl group having 1 or more and 4 or less carbon atoms, an aralkyl group, an aryl group, a heterocyclic group, a substituted amino group, an alkoxy group, an aryloxy group, a halogen atom, or a cyano group.

In the present invention, the ligand $L_1$ and the ligand $L_2$ are different from each other and are not identical to each other.

In the general formula [1], $L_3$ represents a monovalent bidentate ligand having a first atom that forms a coordinate bond with iridium and is selected from N, O, S, and P, and a second atom that forms a coordinate bond with iridium and is selected from N, O, S, and P. In the present invention, the first atom and second atom in $L_3$ may be identical to or different from each other.

Examples of the ligand represented by $L_3$ include, but, of course, not limited to, β-diketonate, picolinate, 2-aminoethanethiolate, 2-aminobenzenethiolate, and 2-(diphenylphosphino)phenolate.

In the present invention, a partial structure $IrL_3$ is preferably a structure represented by the following general formula [6].

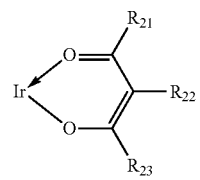

[6]

In the general formula [6], $R_{21}$ to $R_{23}$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group, and may be identical to or different from one another.

It should be noted that specific examples of the alkyl group having 1 or more and 4 or less carbon atoms, aralkyl group, aryl group, heterocyclic group, substituted amino group, alkoxy group, and aryloxy group represented by $R_{21}$ or $R_{22}$ are same as the specific examples of $R_1$ to $R_8$ in the general formula [2]. In addition, when any one of the substituents represented by $R_{21}$ to $R_{23}$ is an alkyl group having 1 or more and 4 or less carbon atoms, an aralkyl group, an aryl group, a heterocyclic group, a substituted amino group, an alkoxy group, or an aryloxy group, the substituent may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, or a pyrenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, or a dibenzothienyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group;

an aryloxy group such as a phenoxy group; a halogen atom such as a fluorine, chlorine, bromine, or iodine atom; and a cyano group.

In the general formula [6], $R_{21}$ to $R_{23}$ each preferably represent a hydrogen atom or an alkyl group having 1 or more and 4 or less carbon atoms. It should be noted that when any one of $R_{21}$ to $R_{23}$ represents an alkyl group having 1 or more and 4 or less carbon atoms, the corresponding substituent may further have an alkyl group having 1 or more and 4 or less carbon atoms, an aralkyl group, an aryl group, a heterocyclic group, a substituted amino group, an alkoxy group, an aryloxy group, a halogen atom, or a cyano group. $R_{21}$ to $R_{23}$ each more preferably represent a hydrogen atom or an alkyl group having 1 or more and 4 or less carbon atoms. When $R_{21}$ to $R_{23}$ each represent a hydrogen atom, its molecular weight reduces and hence the sublimability of the complex itself can be improved. In addition, when $R_{21}$ to $R_{23}$ each represent an alkyl group having 1 or more and 4 or less carbon atoms, an interaction between molecules of the complex reduces and hence the sublimability of the complex itself can be improved.

(1-2) Method of Synthesizing Iridium Complex

Next, a method of synthesizing the iridium complex of the present invention is described. The iridium complex of the present invention is synthesized by, for example, a synthesis scheme (synthesis scheme 1) shown below.

Synthesis Scheme

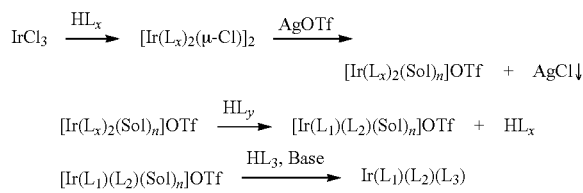

$L_x$ represents $L_1$ or $L_2$, Sol represents a solvent molecule, n represents an integer, when the solvent molecule is a monodentate ligand, n represents 2, when the solvent molecule is a ligand that is bidentate or more, n represents 1, when $L_x$ represents $L_1$, $L_y$ represents $L_2$, and when $L_x$ represents $L_2$, $L_y$ represents $L_1$.

A synthesis process in the synthesis scheme 1 is described below.

First, a triflate form of an iridium complex having two $L_1$'s or $L_2$'s is synthesized according to a method described in PTL 2.

Next, the triflate form of the iridium complex and a compound $HL_2$ or $HL_1$ including a ligand are heated in a solution. Thus, ligand exchange is performed. It should be noted that upon performance of a ligand exchange reaction, the concentration of the solution is properly adjusted before the reaction is performed because a form to which three luminous ligands coordinate is produced when the concentration is high. It should be noted that upon performance of the ligand exchange reaction, a reaction check is desirably performed as appropriate by taking out part of the solution and causing the solution to react with $HL_3$. In addition, while the reaction check is performed as appropriate, the heating is continued until the concentration of a product shows no change.

Next, the iridium complex of the present invention can be synthesized by adding $HL_3$ and a base to the reaction solution. It should be noted that the resultant may contain Ir $(L_1)_2$ $(L_3)$ or Ir $(L_2)_2$ $(L_3)$ as a by-product and hence the by-product needs to be appropriately removed by column purification.

Meanwhile, the iridium complex of the present invention can be synthesized according to a method described in NPL 1. The method is specifically a method of synthesizing the complex by a synthesis scheme (synthesis scheme 2) shown below.

Synthesis Scheme

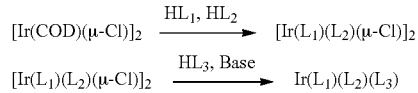

A synthesis process in the synthesis scheme 2 is described below.

First, $[Ir(COD)(\mu-Cl)]_2$ (COD: 1,5-cyclooctadiene), which is an iridium complex, is used as a starting raw material, and $HL_1$ and $HL_2$ are caused to react with the iridium complex simultaneously. Thus, the reaction product is obtained in the form of a mixture containing a chloro-crosslinked dimer ($[Ir(L_1)(L_2)(\mu-Cl)]_2$) having the ligands $L_1$ and $L_2$.

Next, the mixture and $HL_3$ are caused to react with each other under a basic condition. A crude product produced by the reaction is subjected to column purification to provide the iridium complex of the present invention.

Here, the employment of the production method according to the synthesis schemes 1 and 2 typically provides, as a main component, a complex in which nitrogen atoms in $L_1$ and $L_2$, and iridium are coaxially placed like N—Ir—N. At this time, a structural isomer is sometimes produced as a by-product but even a mixture containing the isomer as a by-product is used in some cases in terms of cost.

In addition, when the complex is obtained as a mixture of enantiomers, the mixture may be used without being treated or may be subjected to optical resolution depending on intended purposes.

(1-3) Action and Effect Exhibited by Iridium Complex

The iridium complex of the present invention is formed of trivalent iridium and three kinds of ligands ($L_1$, $L_2$, and $L_3$) that are not identical to one another in structure. In this case, the iridium complex of the present invention is a complex having no symmetry because all the three kinds of ligands are different from one another particularly from a structural viewpoint. Therefore, the iridium complex has low crystallinity in a solid state and an energy for bonding molecules of the complex is small. As a result, the iridium complex of the present invention has high sublimability. It should be noted that details about the sublimability of the complex are described later.

First, the three kinds of ligands of the iridium complex are described.

Of the three kinds of ligands, $L_1$ and $L_2$ each have a carbon atom that forms a covalent bond with iridium and a nitrogen atom that forms a coordinate bond with iridium. In addition, $L_1$ and $L_2$ each serve as a ligand that coordinates to iridium to form a five-membered ring formed of iridium and a partial skeleton N—C—C—C, thereby affecting the phosphorescence characteristics of the complex. That is, the ligands $L_1$ and $L_2$ are each a ligand called a luminous ligand. On the other hand, $L_3$ is called an auxiliary ligand because of its small contribution to the phosphorescence characteristics, though $L_3$ is a monovalent bidentate ligand as in $L_1$ and $L_2$.

First, $L_1$ as a luminous ligand is described. $L_1$ is a ligand having a benzo[f]quinoline skeleton as a basic skeleton and the ring $A_1$ that is an aromatic ring or an aromatic heterocycle. The selection of a predetermined aromatic ring or aromatic heterocycle as the ring $A_1$ causes the partial structure $IrL_1$ including $L_1$ to form a triplet energy level that generates phosphorescence having a wavelength equal to or longer than that of an orange color. In the present invention, the phosphorescence having a wavelength equal to or longer than that of an orange color refers to such light that the maximum peak wavelength of a phosphorescence spectrum is 580 nm or more.

Here, proper selection of the ring $A_1$ causes the partial structure $IrL_1$ to form a triplet energy level that generates phosphorescence whose color ranges from an orange color to a red color. In the present invention, the phosphorescence whose color ranges from an orange color to a red color refers to such light that the maximum peak wavelength of a phosphorescence spectrum is 580 nm or more and 650 nm or less. Phosphorescence having a wavelength in the region can be suitably applied to a display apparatus, a lighting apparatus, or an exposure light source for an image-forming apparatus of an electrophotographic system.

By the way, the benzo[f]quinoline skeleton in the ligand $L_1$ is liable to interact with a benzo[f]quinoline skeleton in an adjacent complex. That is, ring planes in the benzo[f]quinoline skeletons may overlap each other to cause π-π stacking. As a result, an energy for bonding molecules of the complex to each other increases to reduce the sublimability.

In order that the π-π stacking may be suppressed, the benzo[f]quinoline skeleton is preferably provided with a substituent as appropriate to inhibit the approach of the ring planes. In particular, when a substituent is introduced into a substituent bonded to a carbon atom distant from iridium out of the carbon atoms in the benzo[f]quinoline skeleton, specifically, any one of $R_5$ to $R_8$ in the general formula [2], an effect of inhibiting the approach of the ring planes is additionally increased.

Next, the ligand $L_2$ is described. $L_2$ is a luminous ligand as in $L_1$, and is a ligand formed of two kinds of ring structures, i.e., the ring $A_2$ and the ring B. The ring $A_2$ is appropriately selected from an aromatic ring and an aromatic heterocyclic group, and the ring B is appropriately selected from nitrogen-containing aromatic rings depending on desired purposes. Of those, a skeleton capable of forming a stable complex with trivalent iridium is preferred.

The iridium complex of the present invention generates only phosphorescence derived from a partial structure having the lower triplet energy level out of the partial structures $IrL_1$ and $IrL_2$. This is because energy transfer from the partial structure having the higher triplet energy level to the partial structure having the lower triplet energy level occurs. Which partial structure is caused to emit phosphorescence can be appropriately selected depending on desired purposes.

Here, when the luminescent color is changed from an orange color to a red color, molecular design is preferably performed so that phosphorescence may be generated from the partial structure ($IrL_1$) including the benzo[f]quinoline skeleton. This is because the phosphorescence quantum yield of the complex having the partial structure $IrL_1$ is high as described in PTL 3. On the other hand, when phosphorescence is extracted from the partial structure $IrL_2$, the number of heteroatoms in the basic skeleton of each of the ring $A_2$ and the ring B is preferably as small as possible in consideration of the chemical stability of the ligand $L_2$. This is because of the following reason: a carbon atom and a heteroatom are different from each other in electronegativity, and hence charge bias occurs in a bond between both the atoms and the decomposition of the bond by a chemical reaction is liable to occur. In addition, the molecular weight of the basic skeleton of each of the ring $A_2$ and the ring B is preferably as small as possible in consideration of the sublimability of the iridium complex of the present invention. Therefore, in consideration of the number of heteroatoms in the basic skeleton of each of the ring $A_2$ and the ring B, and the molecular weight of the basic skeleton, a preferred aspect of the partial structure $IrL_2$ is such a structure that the ring $A_2$ is a benzene ring and the ring B is a pyridine ring, specifically, the partial structure represented by the general formula [5].

Next, the ligand $L_3$ is described. The ligand $L_3$ is not particularly limited as long as the ligand forms a stable complex with trivalent iridium and does not largely reduce the emission quantum yield. The ligand is preferably a ligand that is formed of a skeleton having a smaller molecular weight than those of the luminous ligands ($L_1$ and $L_2$), and that improves the sublimability of the complex. The ligand $L_3$ that satisfies the requirements is preferably β-diketonate, more preferably a ligand constituting the partial structure represented by the general formula [6].

Next, the sublimability of the iridium complex is described.

In prior art, when a complex having the partial structure $IrL_1$ is obtained, a complex including one kind of luminous ligand represented by the following general formula [a], or a complex including at least one luminous ligand represented by the following general formula [b] and at least one auxiliary ligand is general.

$Ir(L_1)_3$ [a]

$Ir(L_1)_2(L_3)$ [b]

($L_1$ represented in each of the formula [a] and the formula [b], and $L_3$ represented in the formula [b] are the same as $L_1$ and $L_3$ in the general formula [1], respectively.)

Here, the iridium complex represented by the general formula [b] is improved in sublimability as compared to the iridium complex represented by the general formula [a] because the auxiliary ligand ($L_3$) is used. In view of the foregoing, both the iridium complex of the present invention and the iridium complex represented by the general formula [b] were compared from the viewpoints of sublimability and heat stability.

Here, the molecular weight, sublimation temperature ($T_{sub}$), decomposition temperature ($T_d$), and difference between the decomposition temperature and the sublimation temperature ($\Delta T = T_d - T_{sub}$) of each of the iridium complex of the present invention and the iridium complex represented by the general formula [b] are shown.

TABLE 1

| | Structure | Molecular weight | Sublimation temperature $T_{sub}/°C$ | Decomposition temperature $T_d/°C$ | $\Delta T/°C$ |
|---|---|---|---|---|---|
| Exemplified Compound Ir-113 | 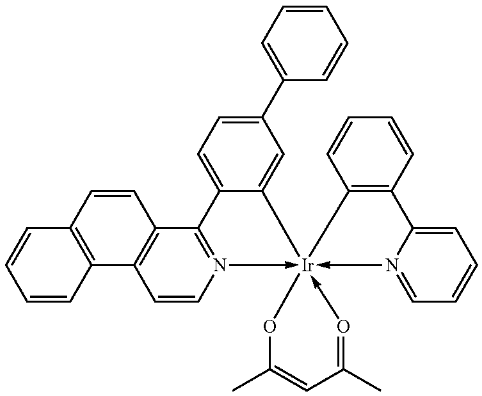 | 775.9 | 300 | 355 | 55 |
| Complex 2 | 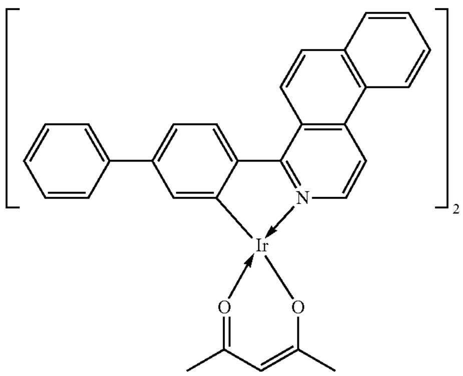 | 952.1 | 370 | 400 | 30 |
| Exemplified Compound Ir-106 | 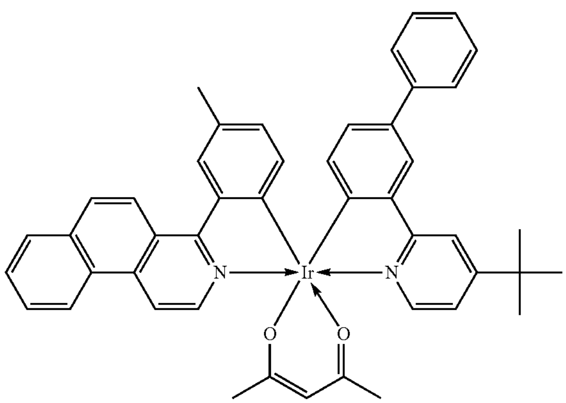 | 846.1 | 290 | 375 | 85 |
| Complex 3 | 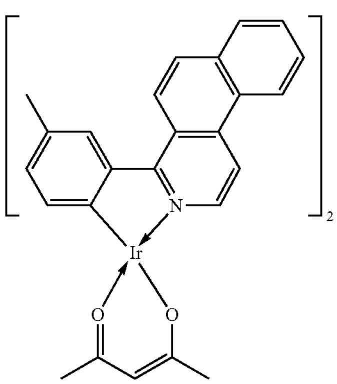 | 828.0 | 345 | 375 | 30 |

Here, the $T_d$ is an indicator of the heat stability of the complex itself and the $\Delta T$ ($=T_d-T_{sub}$) is an indicator of heat stability in a step involving sublimation. Therefore, the $\Delta T$ becomes more important than the $T_d$ is upon sublimation purification or vacuum deposition. This is because when the $\Delta T$ is small, thermal decomposition gradually progresses even at a temperature equal to or lower than the $T_d$ upon sublimation to produce impurities. In addition, a small $\Delta T$ is industrially disadvantageous because the range of regulation of a sublimation rate is small, i.e., step tolerance is small.

Table 1 shows that the $T_{sub}$ of Exemplified Compound Ir-113 is lower than that of Complex 2 by 70° C. and is hence largely improved in sublimability.

A first possible factor for the foregoing is a reduction in crystallinity. While Complex 2 has a $C_2$ symmetrical structure, Exemplified Compound Ir-113 is asymmetrical. Therefore, in Exemplified Compound Ir-113, π-π stacking caused by the approach of $L_1$'s in complex molecules adjacent to each other hardly occurs as compared to Complex 2.

A second possible factor therefor is the fact that the molecular weight of Exemplified Compound Ir-113 is smaller than the molecular weight of Complex 2 by 176.2. The molecular weight of Exemplified Compound Ir-113 was smaller than that of Complex 2, and hence its $T_d$ was lower than that of Complex 2 by 45° C., while its $\Delta T$ ($T_d-T_{sub}$) was larger than that of Complex 2 by 25° C. In other words, it can be said that Exemplified Compound Ir-113 is improved not only in sublimability but also in heat stability at the time of a sublimation operation.

On the other hand, the $T_{sub}$ of Exemplified Compound Ir-106 is lower than that of Complex 3 by 55° C. despite the fact that its molecular weight is larger than that of Complex 3 by 18.1. The foregoing means that an intermolecular interaction between complex molecules significantly reduced. A possible factor for the foregoing is the fact that an effect peculiar to the ligand $L_2$, i.e., a phenyl group and tert-butyl group introduced into 2-phenylpyridine as well as the asymmetry of the complex itself inhibit the intermolecular interaction between the complex molecules.

In addition, the $\Delta T$ ($T_d-T_{sub}$) of Exemplified Compound Ir-106 was larger than that of Complex 3 by 55° C. because values for the $T_d$'s of both the materials were the same. Accordingly, Exemplified Compound Ir-106 is a ligand largely improved in heat stability.

As described above, the iridium complex of the present invention is reduced in crystallinity and improved in sublimability because the complex has three kinds of ligands structurally different from one another to become an asymmetrical complex. Further, the degree of freedom in molecular design of the complex can be increased because the action and effect of the present invention are exhibited as long as the complex has a predetermined partial structure. Specifically, the complex can be additionally improved in sublimability and heat stability as compared to a conventional iridium complex by reducing its molecular weight or introducing a substituent.

Specific examples of the iridium complex of the present invention are shown below.

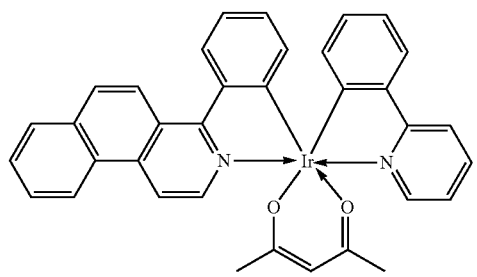

Ir-101

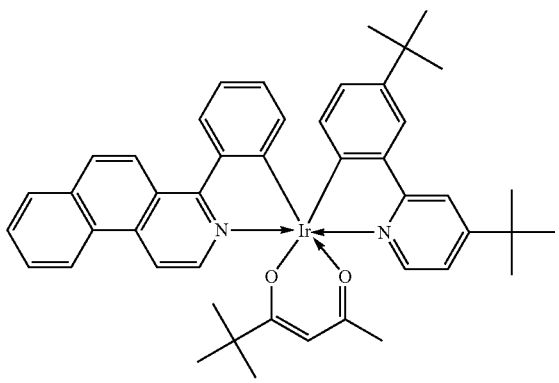

Ir-102

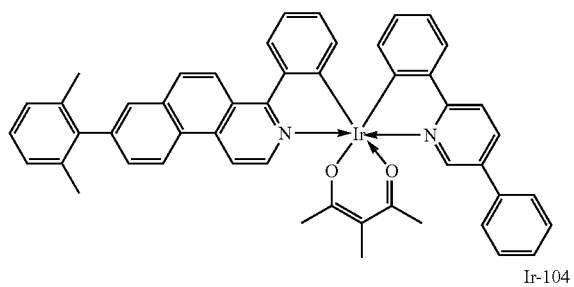

Ir-103

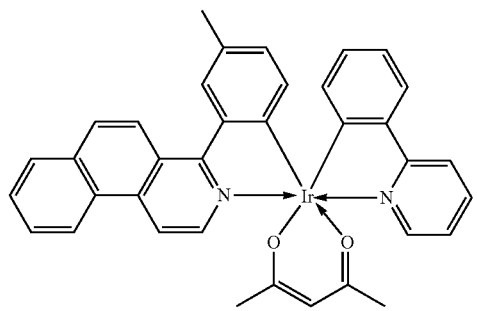

Ir-104

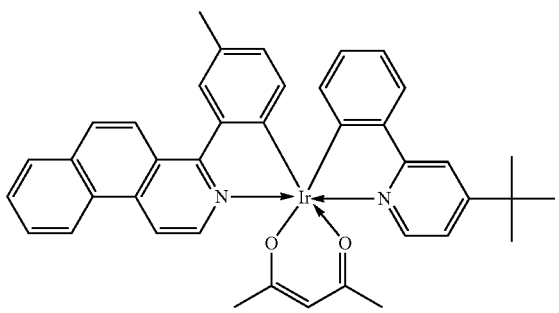

Ir-105

Ir-106
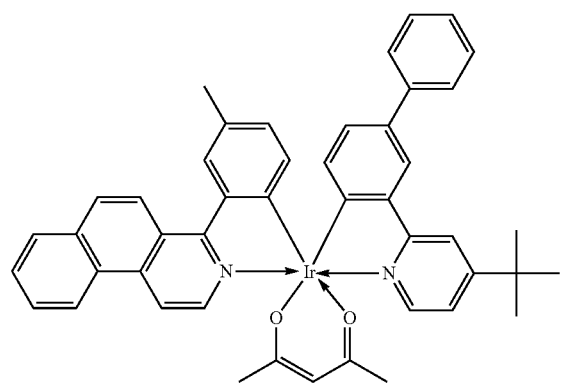
Ir-107
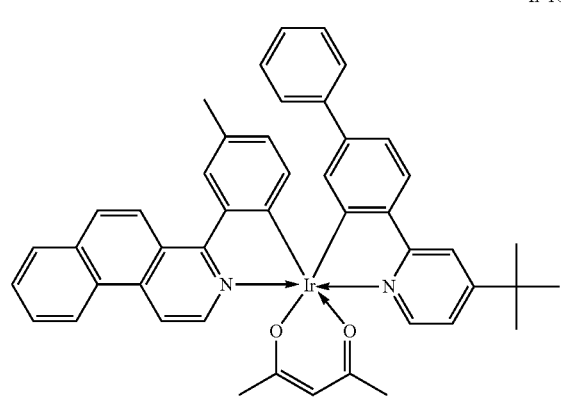
Ir-108
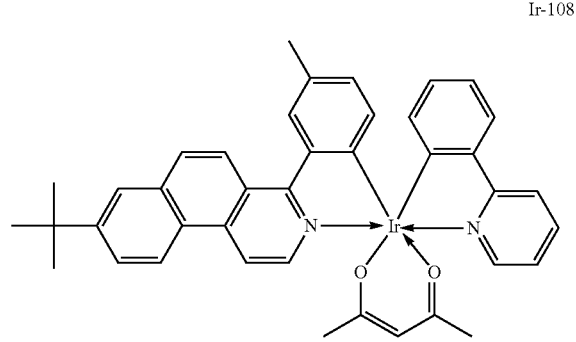
Ir-109
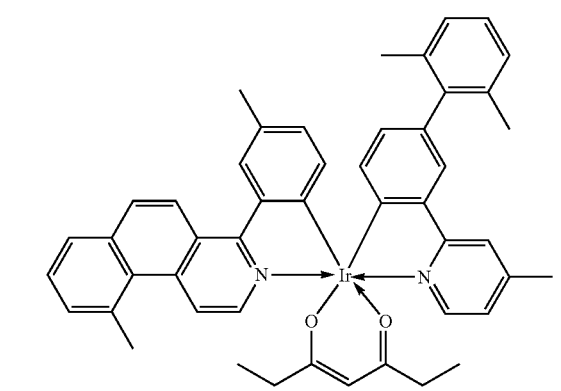
Ir-110
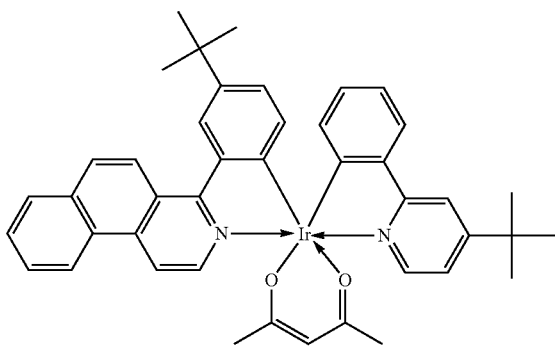
Ir-111
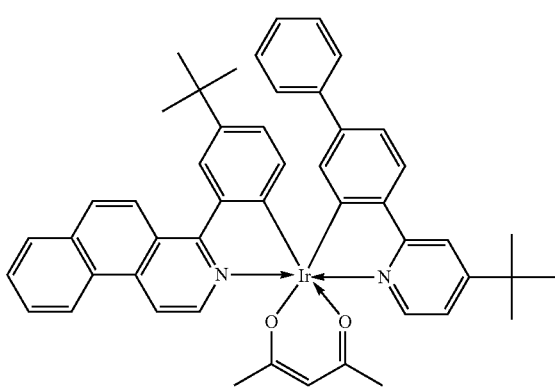
Ir-112
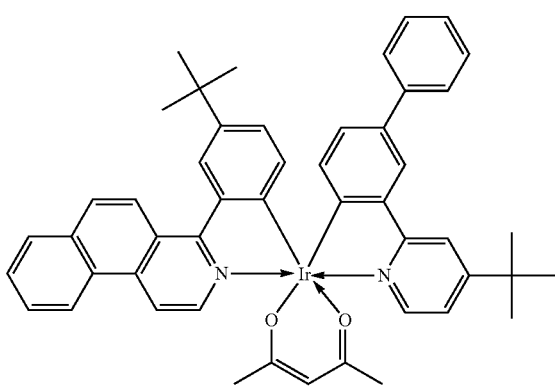
Ir-113
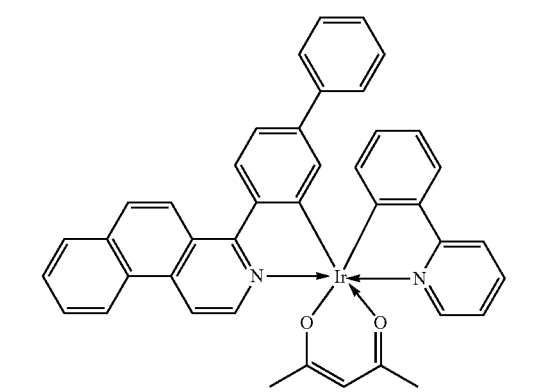

Ir-114
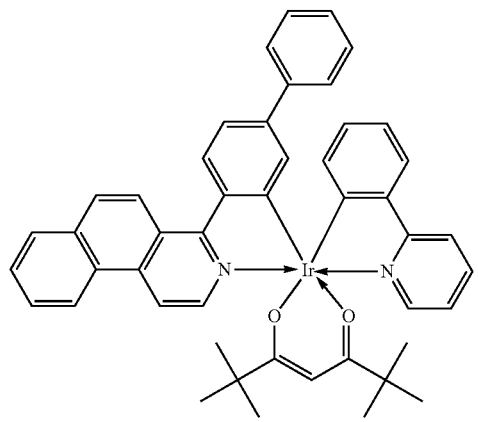
Ir-115
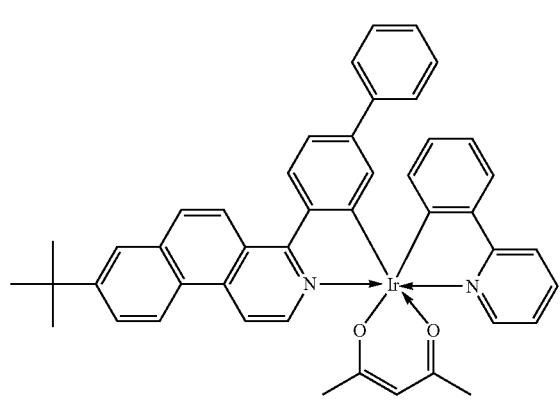
Ir-116
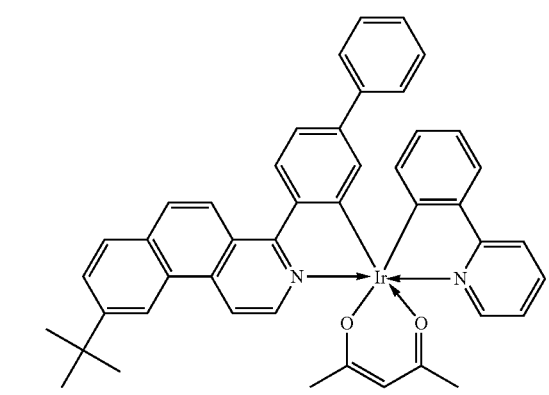
Ir-117
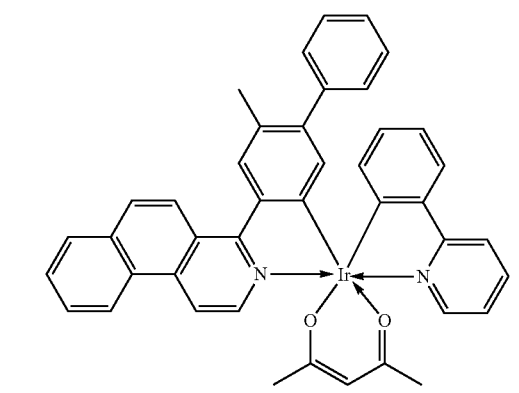
Ir-118
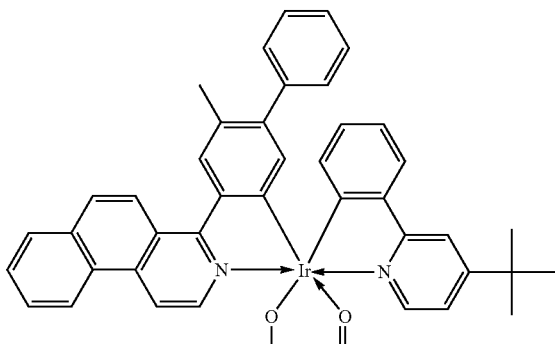
Ir-119
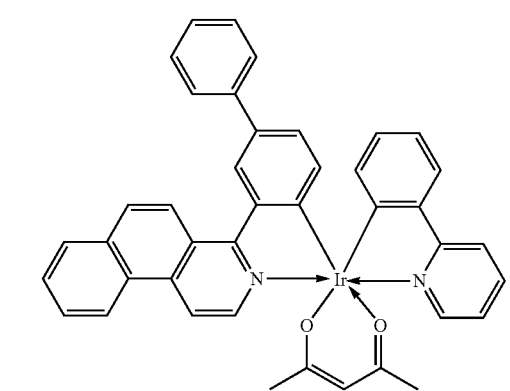
Ir-120
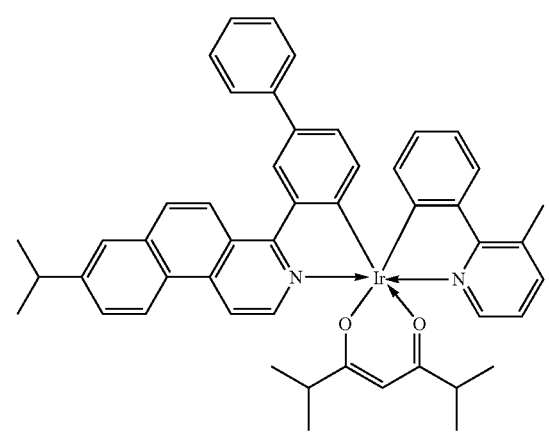
Ir-121
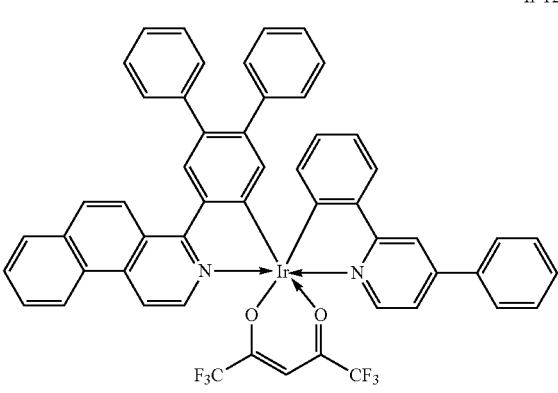

Ir-122
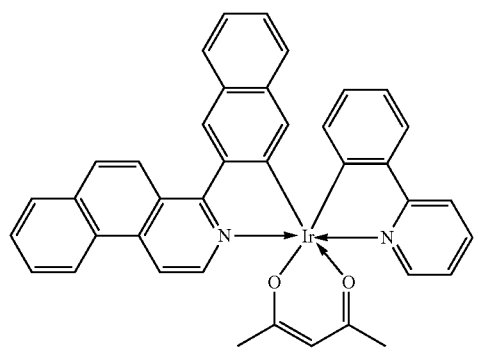
Ir-125
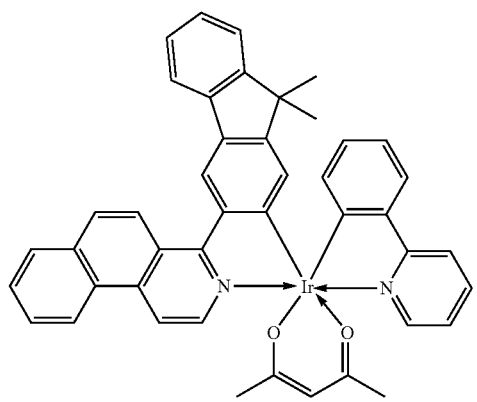
Ir-123
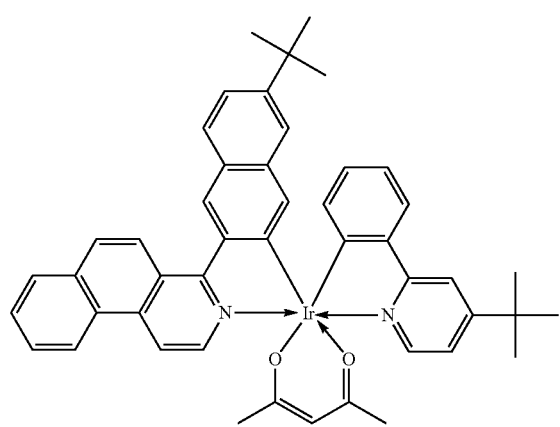
Ir-126
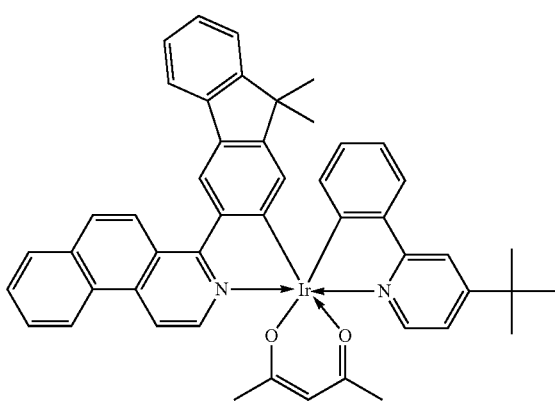
Ir-124
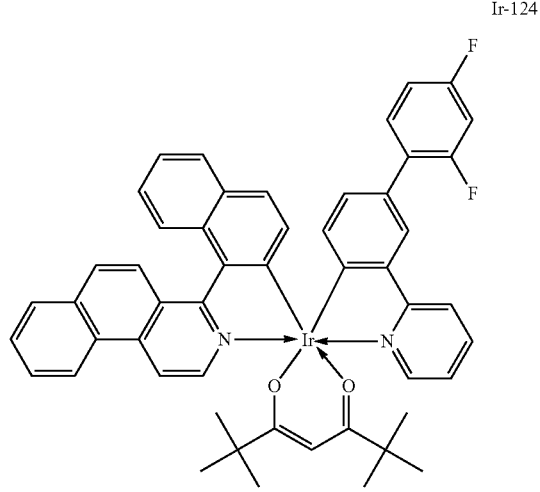
Ir-127
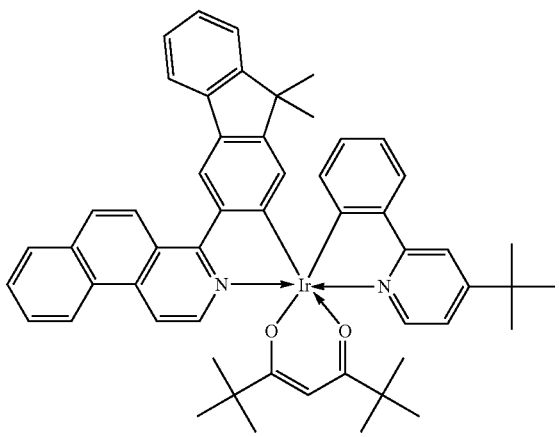

Ir-128
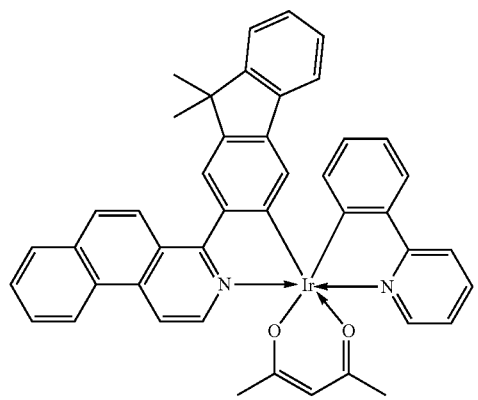
Ir-129
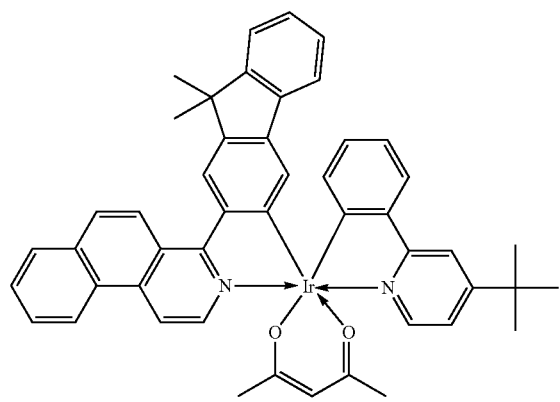
Ir-130
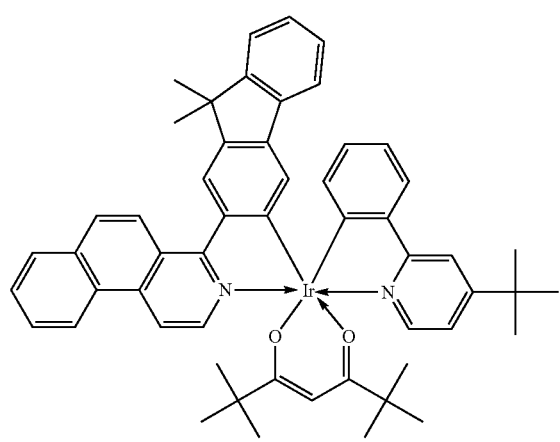
Ir-131
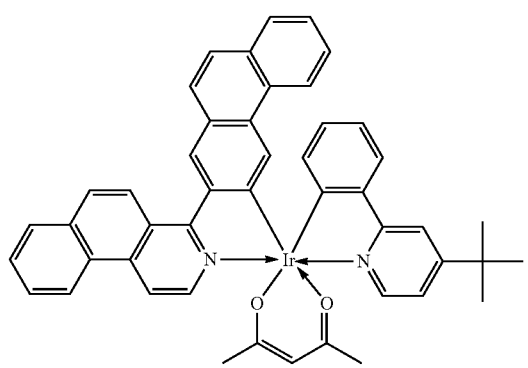
Ir-132
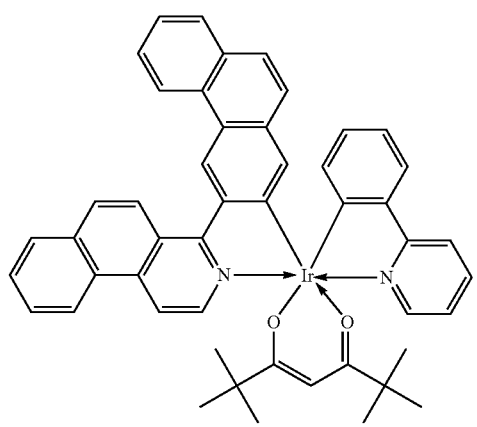
Ir-133
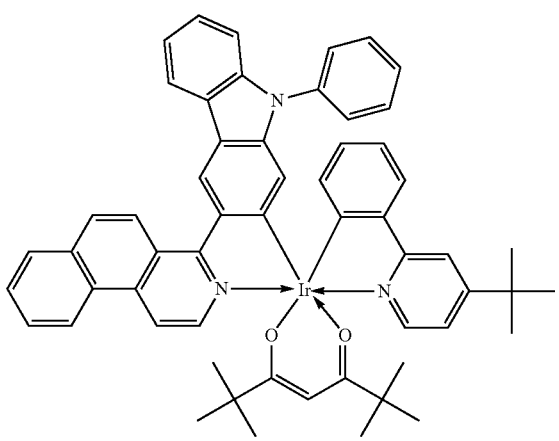

Ir-134
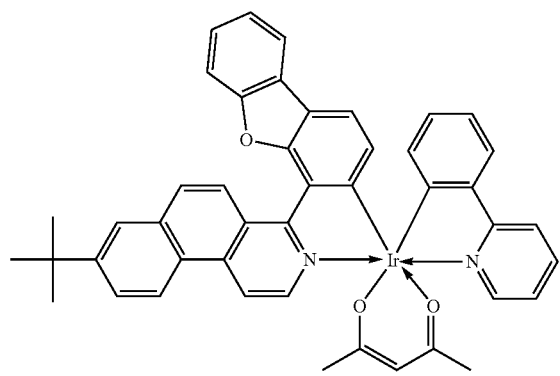
Ir-201
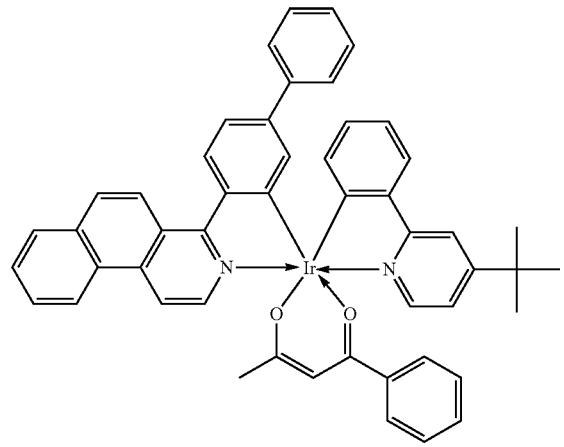
Ir-135
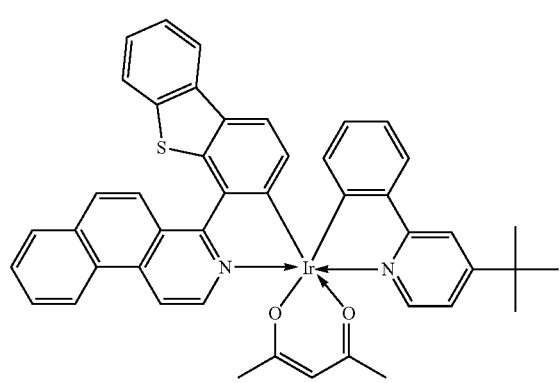
Ir-202
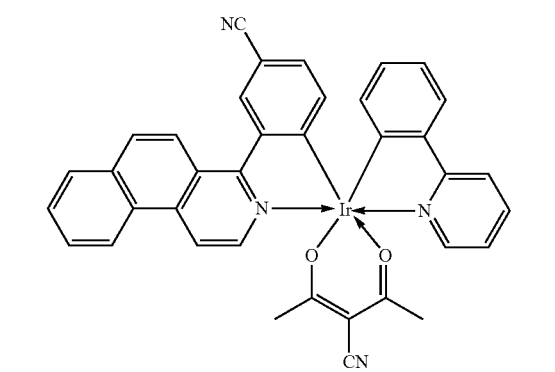
Ir-203
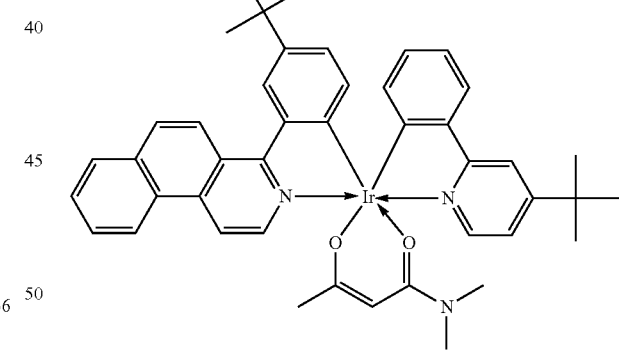
Ir-136
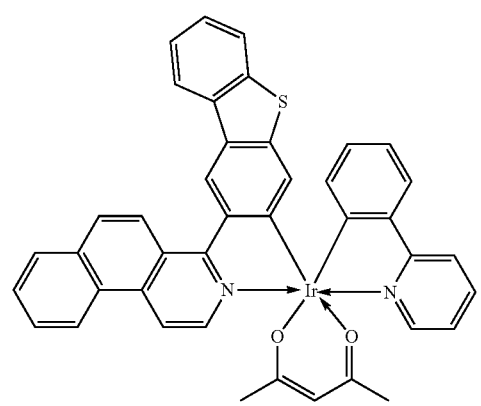
Ir-204

Ir-205
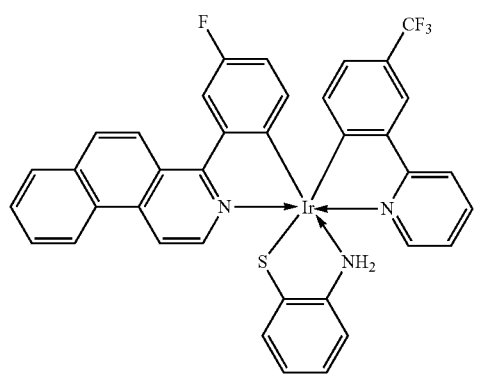
Ir-206
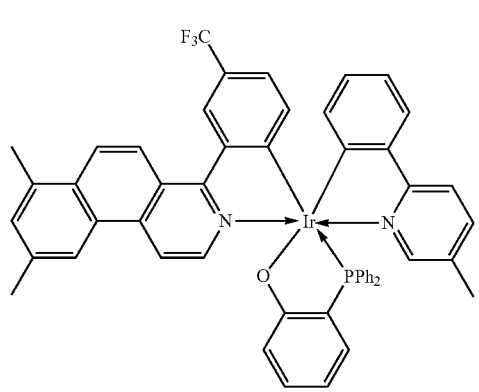
Ir-301
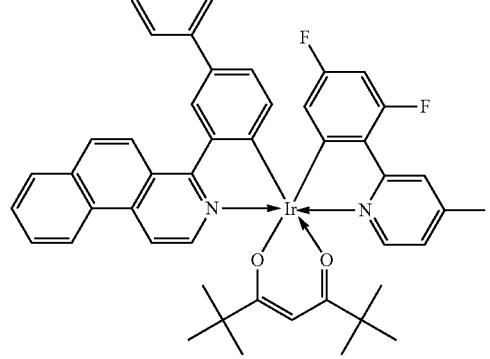
Ir-302
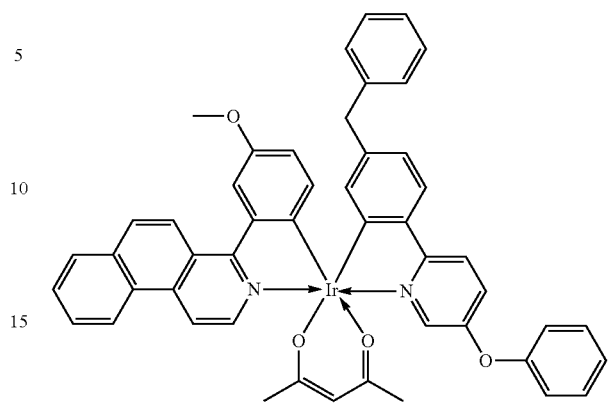
Ir-303
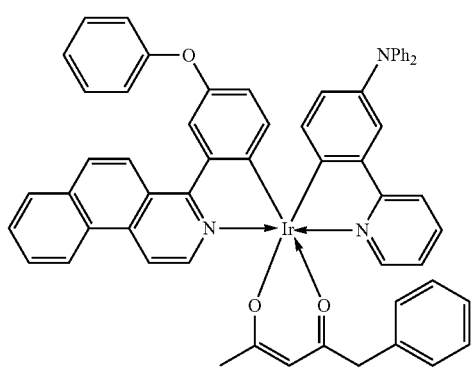
Ir-304
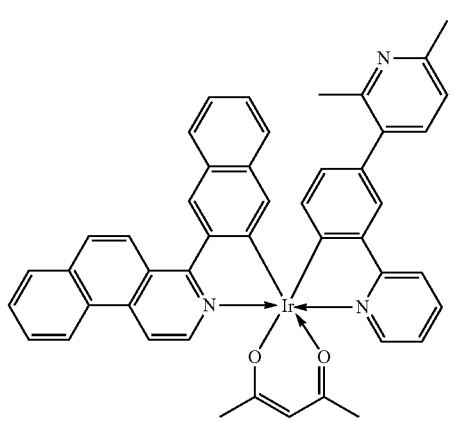
Ir-305
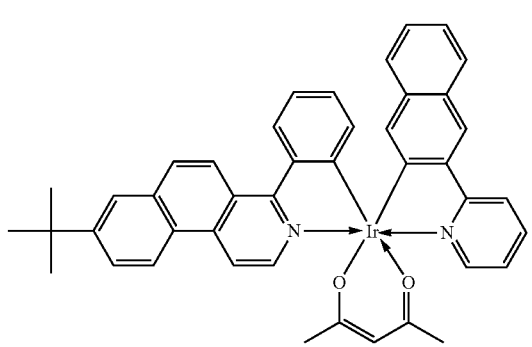

Ir-306
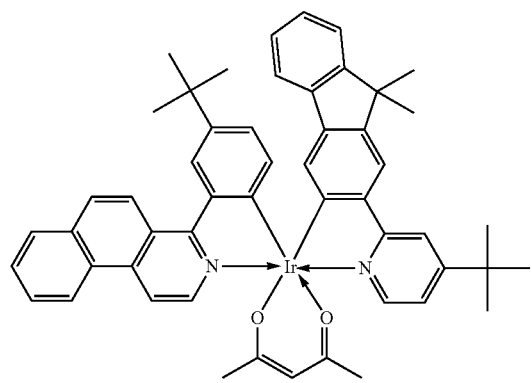
Ir-310
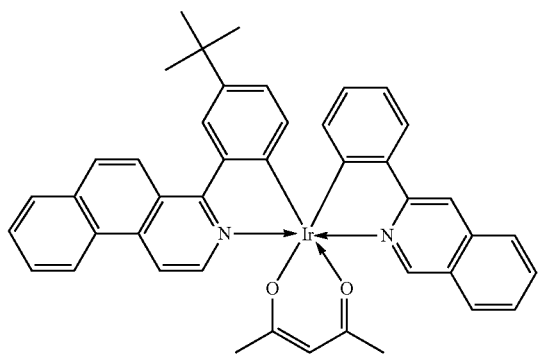
Ir-307
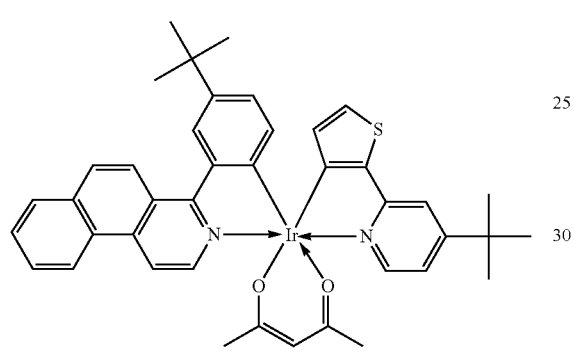
Ir-311
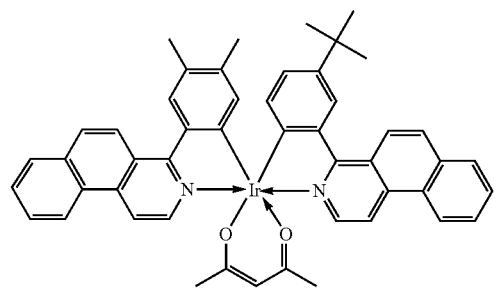
Ir-308
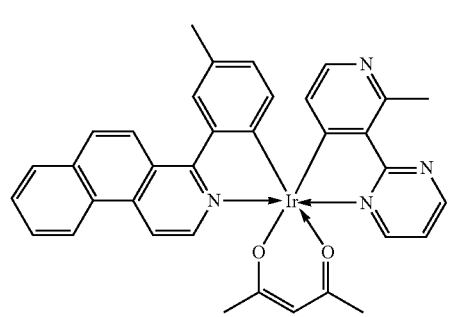
Ir-312
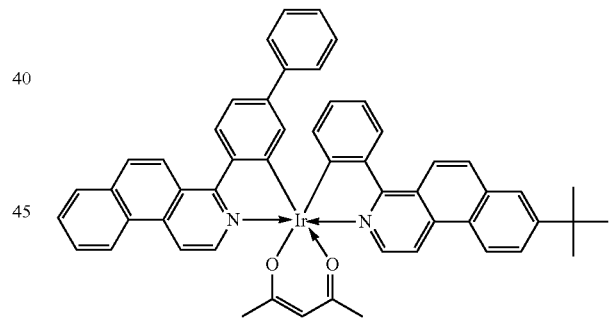
Ir-309
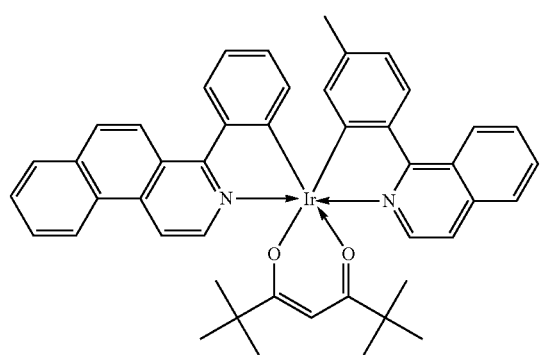
Ir-401
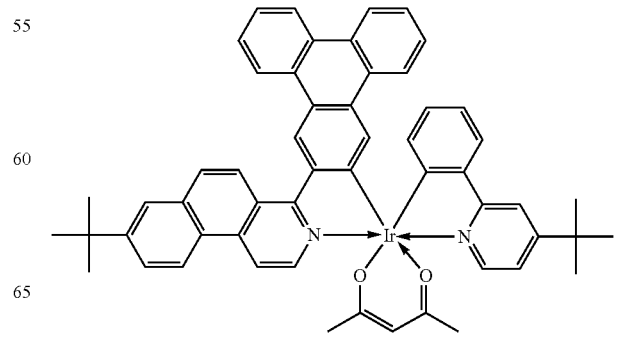

Ir-402

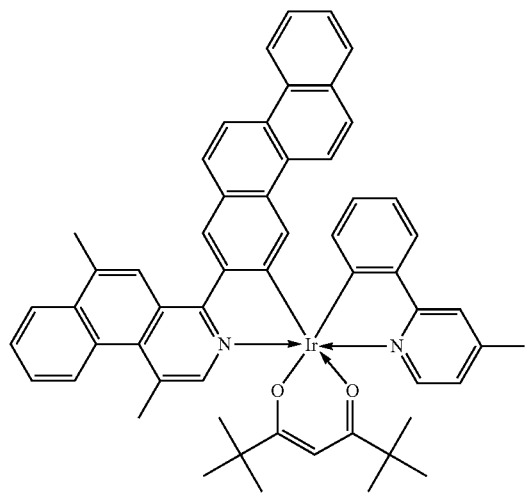

Ir-403

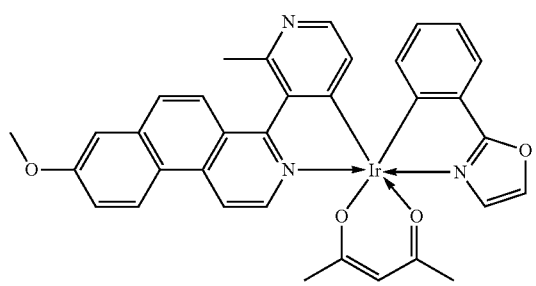

Ir-404

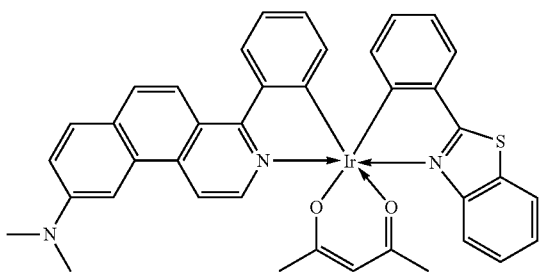

Ir-405

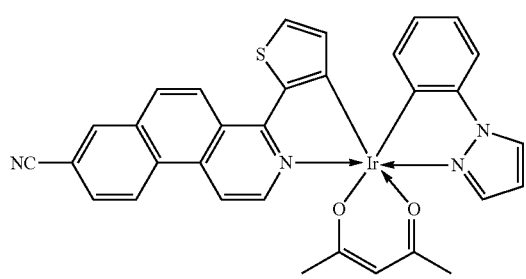

Ir-406

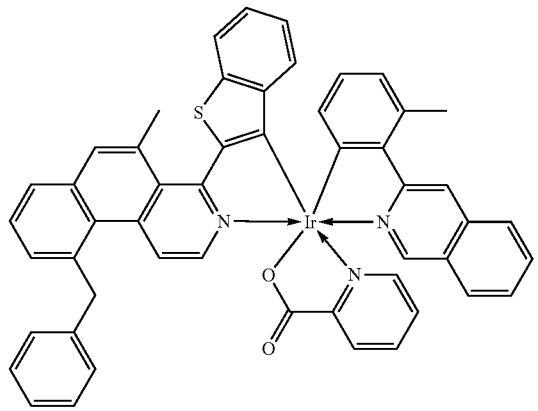

Of the exemplified iridium complexes, Ir-101 to Ir-136 each have a structure given below.

The partial structure including the ligand $L_1$ is the structure represented by the general formula [4].

The partial structure including the ligand $L_2$ is the structure represented by the general formula [5], and $R_{13}$ to $R_{20}$ in the formula [5] each represent a hydrogen atom, an alkyl group having 1 or more and 4 or less carbon atoms, or a phenyl group.

The partial structure including the ligand $L_3$ is the structure represented by the general formula [6], and $R_{21}$ to $R_{23}$ in the formula [6] each represent a hydrogen atom or an alkyl group having 1 or more and 4 or less carbon atoms.

Therefore, Ir-101 to Ir-136 are each particularly excellent in sublimability because preferred aspects of the three kinds of ligands to be incorporated into the iridium complex of the present invention are combined. In addition, the complexes each generate phosphorescence whose color ranges from an orange color to a red color resulting from the partial structure IrL$_1$.

Of the exemplified iridium complexes, Ir-201 to Ir-206 each use β-diketonate or any other bidentate ligand having a specific substituent as the ligand $L_3$. The phosphorescence characteristics of any such iridium complex such as an emission peak wavelength and the waveform of an emission spectrum can be appropriately regulated by changing $L_3$ as the auxiliary ligand.

Of the exemplified iridium complexes, Ir-301 to Ir-312 are each such that the ligand $L_2$ is the ligand represented by the general formula [3] or [5]. In the present invention, the ligand $L_2$ can be selected from a wider range of alternatives as long as its basic structure is represented by the general formula [3]. Here, the (energy level of the) HOMO or LUMO of any such iridium complex can be changed, or phosphorescence based mainly on the partial structure IrL$_2$ can be generated by appropriately selecting the ligand $L_2$.

Of the exemplified iridium complexes, Ir-401 to Ir-406 each have a structure given below. The partial structure including the ligand $L_1$ is the structure represented by the general formula [2]. The partial structure including the ligand $L_2$ is the structure represented by the general formula [3].

In addition, not only phosphorescence whose color ranges from an orange color to a red color but also phosphorescence having a longer wavelength can be generated by $L_1$ represented in each of Ir-401 to Ir-406. In addition, a complex having various physical properties can be designed by appropriately combining $L_1$ and $L_2$ represented in each of Ir-401 to Ir-406.

(2) Organic Light-Emitting Element

Next, an organic light-emitting element of the present invention is described.

(2-1) Element Construction

The organic light-emitting element of the present invention is a light-emitting element including at least: an anode and a cathode that are a pair of electrodes opposite to each other; and an organic compound layer placed between the pair of electrodes. In addition, the organic light-emitting element of the present invention includes, in the organic compound layer, the iridium complex of the present invention and a hydrocarbon compound represented by the following general formula [7].

Details about the hydrocarbon compound represented by the general formula [7] are described later.

The element construction of the organic light-emitting element of the present invention is exemplified by the following element constructions (A) to (E). It should be noted that in each of the element constructions, the organic compound layer necessarily includes an emission layer including a light-emitting material.

(A) (substrate/)anode/emission layer/cathode
(B) (substrate/)anode/hole transport layer/electron transport layer/cathode
(C) (substrate/)anode/hole transport layer/emission layer/electron transport layer/cathode
(D) (substrate/)anode/hole injection layer/hole transport layer/emission layer/electron transport layer/cathode
(E) (substrate/)anode/hole transport layer/emission layer/hole/exciton blocking layer/electron transport layer/cathode It should be noted that the element constructions (A) to (E) are only very basic element constructions for the organic light-emitting element and the present invention is not limited thereto. For example, the following various layer constructions can each be adopted: an insulating layer, an adhesion layer, or an interference layer is provided at an interface between an electrode and the organic compound layer; and the hole transport layer is constructed of two layers having different HOMOs (ionization potentials).

In the present invention, the aspect according to which light output from the emission layer is extracted (element form) may be the so-called bottom emission system in which the light is extracted from an electrode on a side closer to the substrate or may be the so-called top emission system in which the light is extracted from a side opposite to the substrate. In addition, a double-face extraction system (tandem system) in which the light is extracted from each of the side closer to the substrate and the side opposite to the substrate can be adopted.

In the organic light-emitting element of the present invention, the iridium complex of the present invention and the hydrocarbon compound represented by the general formula [7] are preferably incorporated into the emission layer out of the organic compound layer. In this case, the emission layer includes at least the iridium complex of the present invention and the hydrocarbon compound represented by the general formula [7]. The applications of the compounds to be incorporated into the emission layer in this case vary depending on their content concentrations in the emission layer. Specifically, the compounds are classified into a main component and a sub-component depending on their content concentrations in the emission layer.

The compound serving as the main component is a compound having the largest weight ratio (content concentration) out of the group of compounds to be incorporated into the emission layer and is a compound also called a host. In addition, the host is a compound present as a matrix around the light-emitting material in the emission layer, and is a compound mainly responsible for the transport of a carrier to the light-emitting material and the donation of an excitation energy to the light-emitting material.

In addition, the compound serving as the sub-component is a compound except the main component and can be called a guest (dopant), a light emission assist material, or a charge-injecting material depending on a function of the compound. The guest as one kind of sub-component is a compound (light-emitting material) responsible for main light emission in the emission layer. The light emission assist material as one kind of sub-component is a compound that assists the light emission of the guest and is a compound having a smaller weight ratio (content concentration) in the emission layer than that of the host. The light emission assist material is also called a second host by virtue of its function.

When the iridium complex of the present invention and the hydrocarbon compound represented by the general formula [7] are used as constituent materials for the emission layer in the organic light-emitting element of the present invention, the hydrocarbon compound represented by the general formula [7] serves as the host and the iridium complex of the present invention serves as the guest.

The concentration of the guest with respect to the host is 0.01 wt % or more and 50 wt % or less, preferably 0.1 wt % or more and 20 wt % or less, more preferably 1 wt % or more and 15 wt % or less with reference to the total amount of the constituent materials for the emission layer. It is because concentration quenching is to be suppressed that the concentration of the guest is set within the suitable range.

In addition, in the present invention, the host is incorporated at 50 wt % or more with reference to the total amount of the constituent materials for the emission layer. In addition, when a third component to be described later is incorporated into the organic compound layer (preferably the emission layer) separately from the host and the guest, the third component is incorporated at less than 50 wt % with reference to the total amount of the constituent materials for the emission layer.

The inventors of the present invention have made various studies, and have found that an organic light-emitting element using the iridium complex of the present invention as the guest for its emission layer and using the aromatic hydrocarbon compound represented by the general formula [7] as the host has high-efficiency and high-luminance optical output, and has extremely high durability.

(2-2) Regarding Host

Next, the hydrocarbon compound to be used as the host is described. The hydrocarbon compound to be used as the host is a hydrocarbon compound represented by the following general formula [7].

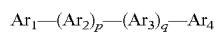

In the formula [7], p and q each represent 0 or 1, but any one of p and q represents 1.

In the formula [7], $Ar_1$ represents any one of the substituents represented in the following substituent group α1 (preferably the substituent group α2).

[Substituent group α1]
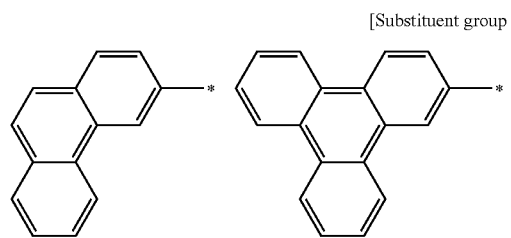
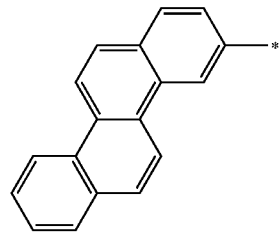
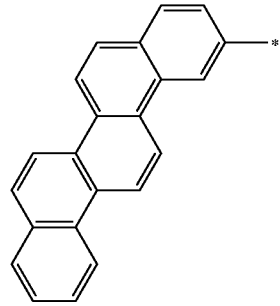
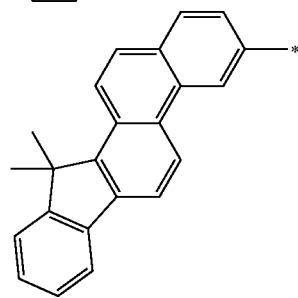
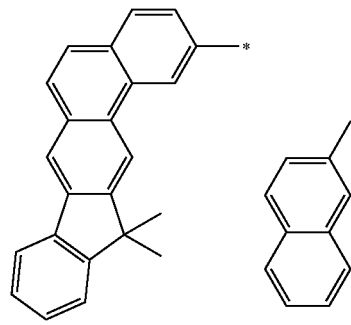
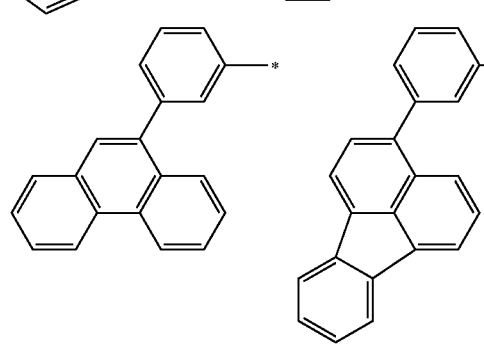
[Substituent group α2]
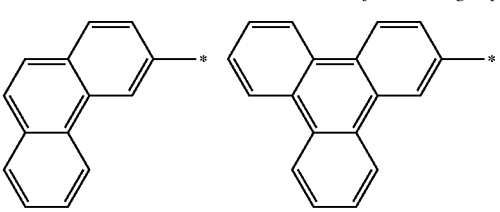
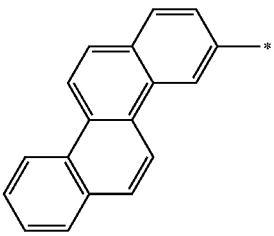
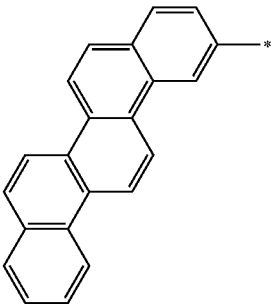
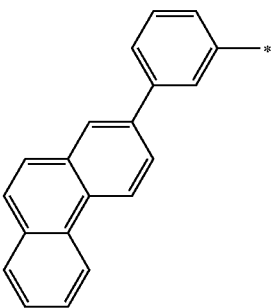
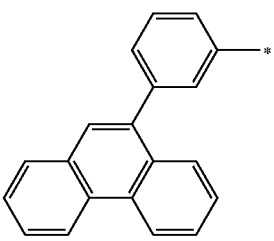
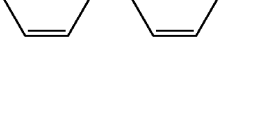
(* represents a bonding hand with an adjacent substituent.)
In the formula [7], $Ar_2$ and $Ar_3$ each represent any one of the substituents represented in the following substituent group β1 (preferably the substituent group β2). It should be noted that $Ar_2$ and $Ar_3$ may be identical to or different from each other.

[Substituent group β1]
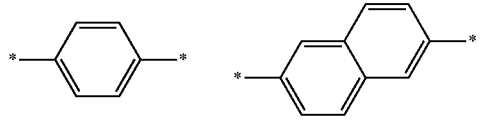
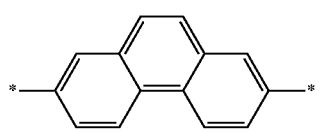
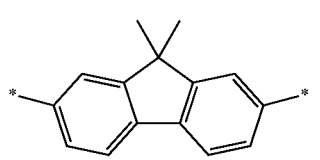
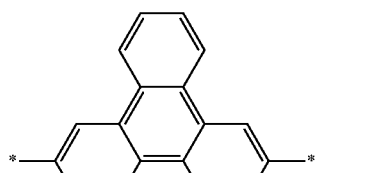
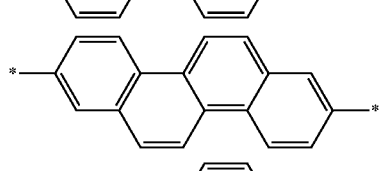
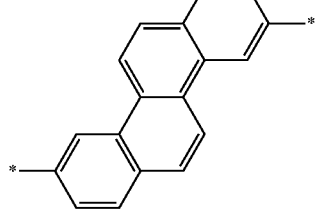
[Substituent group β2]
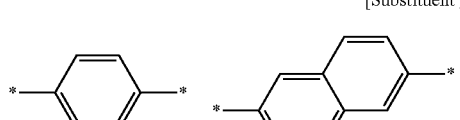
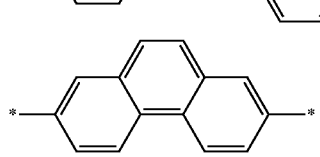
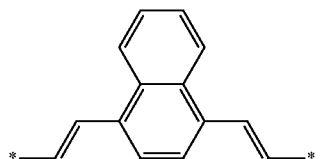
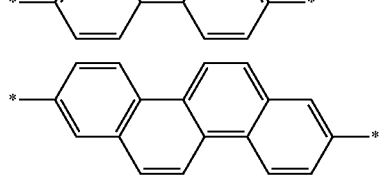
-continued
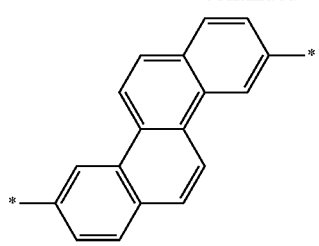
(* represents a bonding hand with an adjacent substituent.)
In the formula [7], $Ar_4$ represents any one of the substituents represented in the following substituent group γ1 (preferably the substituent group γ2).
[Substituent group γ1]
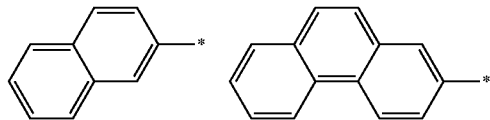
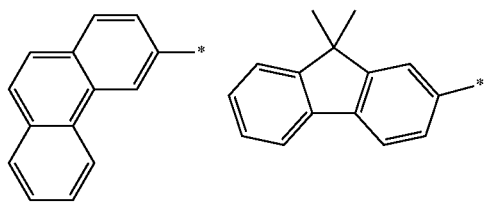
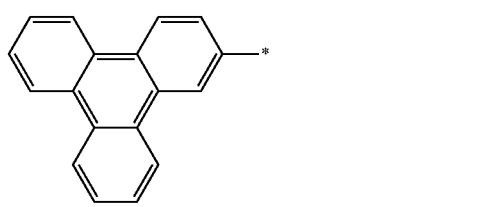
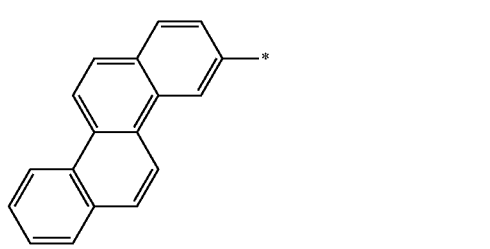
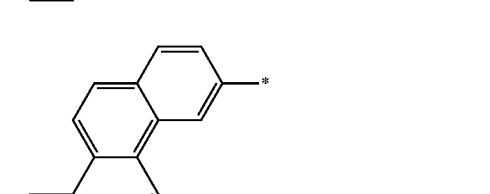

-continued

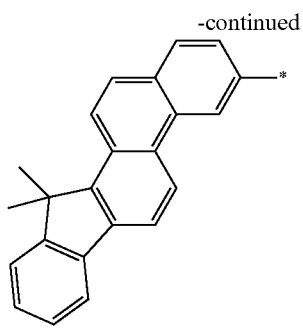
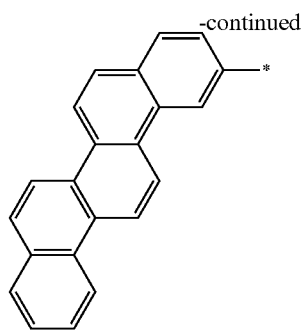
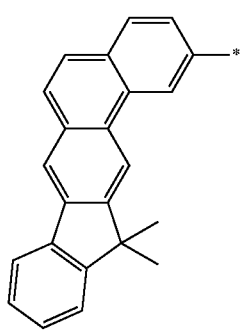
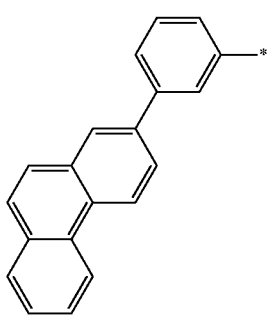
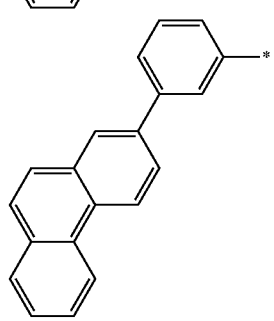
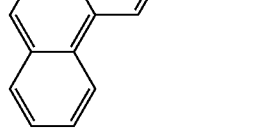
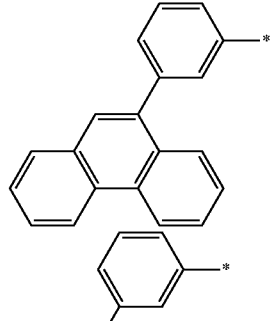
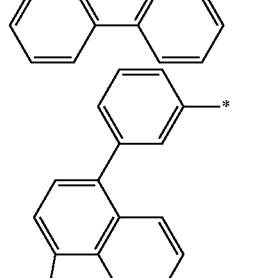
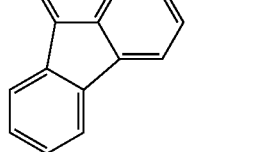

[Substituent group γ2]

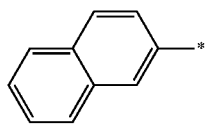
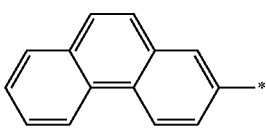

(* represents a bonding hand with an adjacent substituent.)

Although $Ar_1$ and $Ar_4$ may be identical to or different from each other, $Ar_1$ and $Ar_4$ preferably represent different substituents from the viewpoint of a reduction in symmetry.

In the present invention, the iridium complex of the present invention and the hydrocarbon compound represented by the general formula [7] are incorporated into the organic compound layer (preferably the emission layer). It should be noted that a material serving as the third component may also be incorporated into the organic compound layer together with the iridium complex and the hydrocarbon compound.

(2-3) Third Component

In the present invention, a compound serving as the third component is a material having the following feature (2a), (2b), or (2c):

(2a) a material having a larger (shallower) HOMO level than the HOMO level of the host;
(2b) a material having an LUMO level smaller in energy (deeper) than the LUMO level of the host; and (2c) a material having an HOMO level larger in energy than the HOMO level of the host and having an LUMO level smaller in energy than the LUMO level of the host.

The material having the feature (2a) facilitates the injection and transport of a hole into the emission layer by virtue of its shallow HOMO level. As a result, a reduction in driving voltage of the element is achieved and the light-emitting material can be suppressed from being excessively brought into an anion state, and hence the lifetime of the element is lengthened.

The material having the feature (2b) lengthens the lifetime of the element by the following reason. That is, the LUMO level of the host is shallower (larger in energy) than that of the light-emitting material, and hence the addition of the third component having a deeper LUMO level than the LUMO level of the host can suppress the light-emitting material from being excessively brought into an anion state. Therefore, the lifetime is lengthened.

The material having the feature (2c) can improve hole injection property and alleviate electron trapping by the light-emitting material. Accordingly, the lifetime is lengthened as a result of the foregoing.

Specific examples of the third component are described later.

(2-4) Action and Effect Exhibited by Host

The host to be incorporated into the organic light-emitting element is brought into a chemically unstable state such as a radical cation state, a radical anion state, an excited singlet state, or an excited triplet state. In addition, the host is exposed to a high-temperature state such as sublimation purification, vacuum deposition, or the heat generation of the organic light-emitting element itself. Therefore, the host to be incorporated as a constituent material for the organic light-emitting element is required to have high heat stability and high chemical stability.

In general, an aromatic hydrocarbon compound has higher heat stability and higher chemical stability than those of a compound containing a heteroatom. In addition, the aromatic hydrocarbon compound more easily forms a stable amorphous thin film having a high glass transition point than an aliphatic hydrocarbon compound does. Therefore, in the present invention, the aromatic hydrocarbon compound is suitably used as the host that is one of the constituent materials for the organic light-emitting element.

A compound constructed by appropriately combining multiple aromatic hydrocarbon compound skeletons is preferred as the aromatic hydrocarbon compound. This is because its physical properties can be easily adjusted by changing the combination of the skeletons.

The emission peak wavelength of the iridium complex of the present invention to be incorporated as the guest into the emission layer mainly falls within the range of 580 nm to 650 nm {1.9 eV to 2.1 eV in terms of the lowest triplet energy level $(T_1)$}. Therefore, the host material needs to have a higher $T_1$ energy than that of the guest material. Table 2 shows the $T_1$ energy, and difference ($\Delta S-T$) between the lowest excited singlet level $(S_1)$ energy and the $T_1$ energy, of an aromatic hydrocarbon compound skeleton.

TABLE 2

| | Structural formula | $T_1$/ eV | $\Delta S-T$/ eV |
|---|---|---|---|
| Benzene | | 3.66 | 1.11 |
| Naphthalene | | 2.63 | 1.37 |
| Phenanthrene | | 2.70 | 0.90 |
| Fluorene | | 2.94 | 1.19 |
| Triphenylene | | 2.90 | 0.72 |
| Chrysene | | 2.48 | 0.95 |
| Picene | | 2.49 | 0.81 |
| Indeno [2,1-a] phenanthrene | | 2.58 | 1.07 |
| Indeno [1,2-b] phenanthrene | | 2.61 | 1.07 |
| Fluoranthene | | 2.29 | 0.77 |
| Anthracene | | 1.84 | 1.45 |

| | Structural formula | $T_1$/eV | $\Delta$S-T/eV |
|---|---|---|---|
| Pyrene | 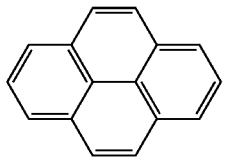 [SMILES: c1cc2ccc3cccc4ccc(c1)c2c34] | 2.10 | 1.24 |

The $T_1$ energy of the host needs to be made larger than at least 2.1 eV.

In order that the $T_1$ energy of the host may be made larger than at least 2.1 eV, the aromatic hydrocarbon compound as the host preferably has multiple aromatic hydrocarbon compound skeletons each independently selected from the group consisting of benzene, naphthalene, phenanthrene, fluorene, triphenylene, chrysene, fluoranthene, picene, indeno[2,1-a]phenanthrene having, only on $sp^3$ carbon, two alkyl groups each having 1 or more and 4 or less carbon atoms, and indeno[1,2-b]phenanthrene having, only on $sp^3$ carbon, two alkyl groups each having 1 or more and 4 or less carbon atoms.

It should be noted that out of the aromatic hydrocarbon compound skeletons, benzene, naphthalene, phenanthrene, triphenylene, chrysene, fluoranthene, and picene each need to be free of a substituent except a bond between the skeletons constituting the aromatic hydrocarbon compound.

Fluorene, indeno[2,1-a]phenanthrene, and indeno[1,2-b]phenanthrene each have an $sp^3$ carbon atom in its skeleton. A hydrogen atom bonded to the $sp^3$ carbon atom has higher acidity than that of a hydrogen atom bonded to an $sp^2$ carbon atom, that is, proton dissociation easily occurs. This is because an electron pair produced as a result of the proton dissociation conjugates with an aromatic ring to stabilize.

Therefore, in order that the chemical stability may be additionally improved, fluorene, indeno[2,1-a]phenanthrene, and indeno[1,2-b]phenanthrene each preferably have, on $sp^3$ carbon in its skeleton, two alkyl groups each having 1 or more and 4 or less carbon atoms.

Specific examples of the host that can be used as a constituent material for the organic light-emitting element of the present invention are shown below. However, the present invention is of course not limited thereto.

X-101

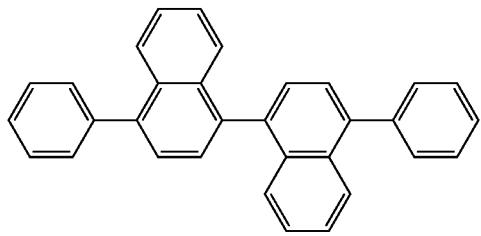

X-102

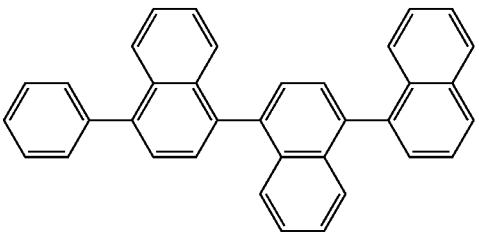

X-103

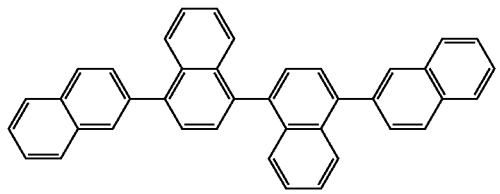

X-104

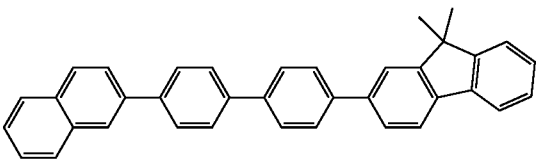

X-105

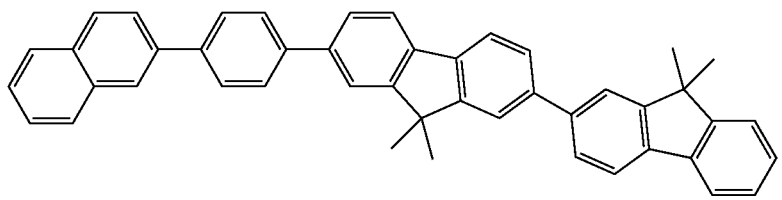

X-106

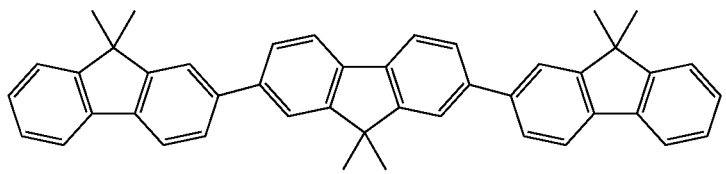

-continued
X-107
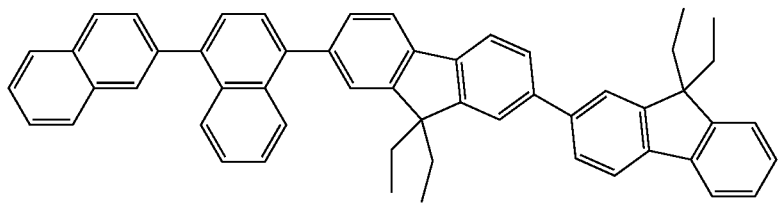
X-108
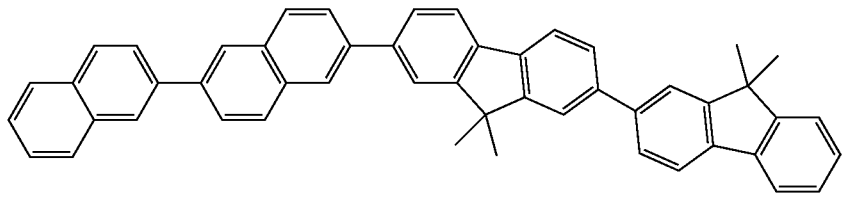
X-109
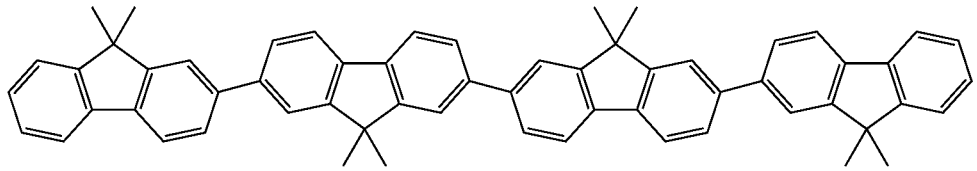
X-110
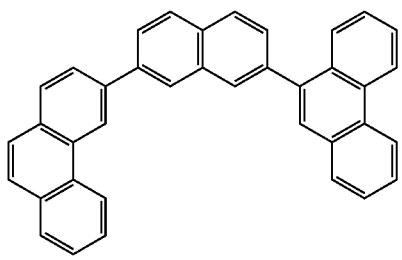
X-111
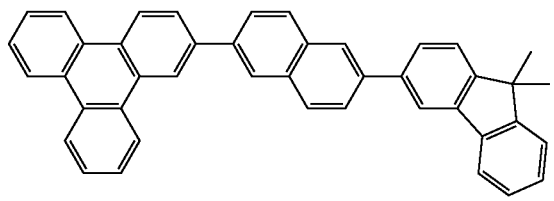
X-112
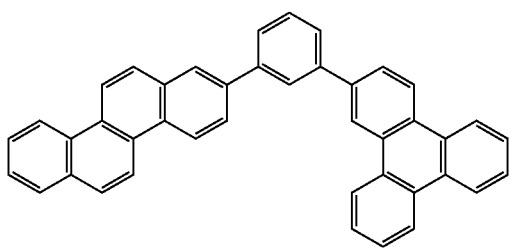
X-113
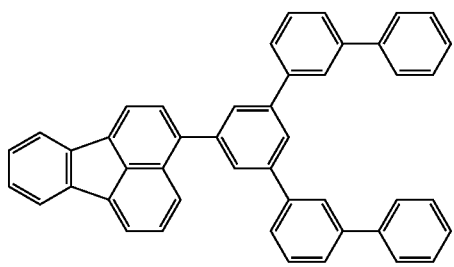
X-114
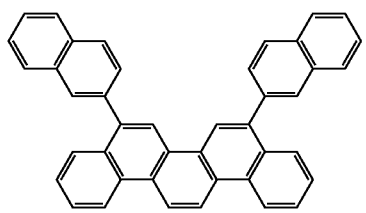
X-115
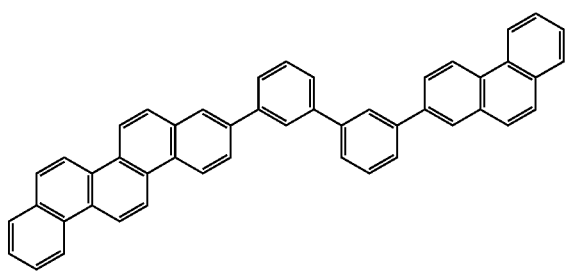

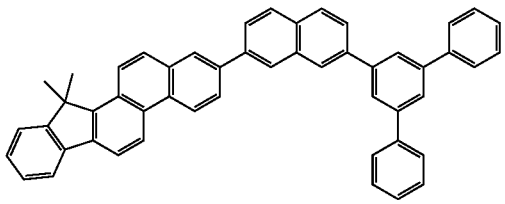

X-116

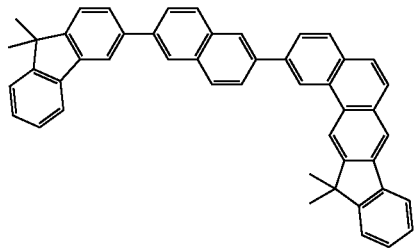

X-117

Next, a suitable aspect out of the hosts listed above is described. The inventors of the present invention have made extensive studies on the organic light-emitting element according to the present invention. As a result, the inventors have found the following two points as causes for reductions in efficiency and durability:
(i) the formation of a radical state by the guest that has trapped the charge of the host; and
(ii) the formation of an exciplex by the host and the guest.

In order that the causes (i) and (ii) may be avoided, it is effective to select, as the compound to be used as the host, a compound having a unit that forms a band gap and a unit that reduces an intermolecular interaction. More specifically, a compound having the structure represented by the general formula [7] is selected.

First, the unit that forms a band gap is described in detail by taking the hydrocarbon compound represented by the general formula [7] as a specific example. In the hydrocarbon compound represented by the general formula [7], the unit that forms a band gap refers to a linear partial structure shown below out of the entire structure represented by the general formula [7].

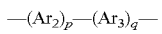

It should be noted that any other partial structure, specifically, part or the entirety of $Ar_1$ and $Ar_4$ can also constitute the unit that forms a band gap.

By the way, the band gap of the host needs to be properly designed in order that excessive transition of the guest to a radical state may be avoided. Here, although it is essential for the $T_1$ of the host to be higher than the $T_1$ of the guest, the lowest singlet energy level ($S_1$) and band gap of the host necessarily enlarge when the $T_1$ of the host is excessively high.

The foregoing is responsible for the promotion of the deterioration of the organic light-emitting element. A first reason therefor is that charge accumulation occurs at an interface between the host and a charge transport layer material. A second reason therefor is as follows: a difference in level difference between the highest occupied molecular orbital (HOMO) and the lowest unoccupied molecular orbital (LUMO) between the host and the guest enlarges, and hence the guest serves as a charge trap.

Here, the iridium complex of the present invention easily traps an electron probably because its LUMO orbital is spatially extended by virtue of the presence of a benzo[f]quinoline ring in its basic skeleton. Therefore, a host having a narrow band gap is preferably used so that the injection and transport of the electron may be smoothly performed.

In consideration of the $T_1$ of the guest and the $\Delta S$–$T$ value shown in Table 2, the band gap of the host is preferably 2.7 eV to 3.6 eV, more preferably 2.7 eV to 3.4 eV.

In order that the band gap of the host may be controlled to fall within the range, conjugation needs to be extended over the entire molecule. Therefore, $Ar_2$ and $Ar_3$ in the general formula [7] each preferably have a linear bonding mode as represented in the substituent group β1 (preferably the substituent group β2). That is, it is important that hydrogen atoms bonded to the peri-positions be absent. This is because of the following reason: when the hydrogen atoms bonded to the peri-positions are absent, the dihedral angle of an aromatic ring plane reduces and p orbitals are in parallel contact with each other, and hence a n-bond is partially formed to extend the conjugation.

For example, in the case where naphthalene rings are bonded, when an attempt is made to bond the naphthalene rings through a carbon atom at the 1-position or 4-position, hydrogen atoms bonded to carbon atoms at the 5-position and 8-position of a naphthalene ring correspond to the hydrogen atoms bonded to the peri-positions. In that case, steric repulsion occurs between any such hydrogen atom and a hydrogen atom of an adjacent naphthalene ring to enlarge the dihedral angle. As a result, the extent to which the p-orbitals overlap each other reduces, the conjugation does not extend, and the band gap increases. On the other hand, when the naphthalene rings are bonded through a carbon atom at the 2-position or 6-position, the steric repulsion hardly occurs because the hydrogen atoms bonded to the peri-positions are absent. Accordingly, the conjugation extends, whereby the band gap reduces.

In consideration of the foregoing, the hydrogen atoms bonded to the peri-positions are also preferably absent in a bond between $Ar_1$ and $Ar_2$, and a bond between $Ar_3$ and $Ar_4$.

By the way, when a partial structure having a fluorene skeleton is selected as each of $Ar_2$ and $Ar_3$, the 9-position of the fluorene skeleton is preferably substituted with two methyl groups. This is because an alkyl group having 2 or more and 4 or less carbon atoms leads to so large steric hindrance that the group inhibits charge transfer between a host molecule and another host molecule to cause an increase in driving voltage of the element and the reduction of its durability.

A material having a band gap suitable for outputting red phosphorescence is obtained by taking the conditions described above into consideration. In addition, the band gap is small, and hence the property by which charge is injected into the emission layer improves and the charge accumulation of the charge transport layer that leads to the deterioration can be avoided.

Next, the unit that reduces an interaction is described in detail. The unit that reduces an interaction refers to a moiety having a major axis in a direction different from the major axis direction of the unit that forms a band gap. In the hydrocarbon compound represented by the general formula [7], part or the entirety of $Ar_1$ and $Ar_4$ correspond to the unit.

When a planar and linear compound is used as the host, the formation of the host into a film serving as a constituent member for the organic light-emitting element results in strong close contact between the host and the guest. The LUMO orbital of the iridium complex of the present invention to be used as the guest in the present invention is extended. Accordingly, the guest may be liable to accept an electron from the host in close contact with the guest to be brought into a radical state. In addition, the host and the guest more easily form an exciplex as an intermolecular distance between the host and the guest shortens.

In view of the foregoing, the inventors of the present invention have found that a compound in which the major axis direction of a partial structure corresponding to $Ar_1$ and $Ar_4$, and a bonding direction to $Ar_2$ and $Ar_3$ (the major axis direction of each of $Ar_2$ and $Ar_3$) are directions different from each other is suitable as the host. That is, it is preferred that in the general formula [7], $Ar_1$ represent a partial structure represented in the substituent group α1 (preferably the substituent group α2) and $Ar_4$ represent a partial structure represented in the substituent group γ1 (preferably the substituent group γ2).

A compound whose entire structure is represented by the general formula [7] and in which the partial structures ($Ar_1$ to $Ar_4$) each correspond to any one belonging to the predetermined substituent group is used as the host. Thus, excessive transition of the guest to a radical state, and the formation of an exciplex between the host and the guest are alleviated. A possible reason for such effect is that the close contact between the host and the guest is suppressed by the twist of each of $Ar_1$ and $Ar_4$ at the terminals in a direction different from the major axis directions of $Ar_2$ and $Ar_3$.

Here, as long as at least one of $Ar_1$ and $Ar_4$ has a twist in the major axis direction, the excessive transition of the guest to a radical state and the formation of an exciplex can be suppressed. Therefore, for example, as long as a requirement concerning the major axis direction of a partial structure is satisfied for $Ar_1$, the major axis direction of $Ar_4$ may be identical to the major axis directions of $Ar_2$ and $Ar_3$. That is, as long as the requirement concerning the major axis direction of a partial structure is satisfied for $Ar_1$, $Ar_4$ may represent any one of a 2-fluorenyl group, 2-naphthyl group, and 2-phenanthryl group represented in the substituent group γ1 (and the substituent group γ2).

By the way, a carbon atom at each of the 13-position of an indeno[2,1-a]phenanthrene skeleton, the 12-position of an indeno[1,2-b]phenanthrene skeleton, and the 9-position of a fluorene skeleton, the skeletons being each selected as $Ar_1$ or $Ar_4$, is preferably substituted with two methyl groups. This is because an alkyl group having 2 or more and 4 or less carbon atoms causes a remarkable increase in driving voltage and a remarkable reduction in durability from the viewpoint of the entirety of the element performance, though the group exhibits a large suppressing effect on the close contact between both the materials, i.e., the host and the guest.

When the hydrocarbon compound represented by the general formula [7] is used as the host, $Ar_1$ and $Ar_4$ more preferably represent skeletons different from each other. This is because of the following reason: the symmetry of the entire molecule reduces as compared with a compound in which $Ar_1$ and $Ar_4$ represent the same skeleton, and hence the close contact between both the materials, i.e., the host and the guest can be additionally suppressed.

As described above, the two units ("the unit that forms a band gap" and "the unit that reduces an interaction") are preferably provided in the basic skeleton of the compound serving as the host. Thus, the excessive transition of the guest to a radical state, and the formation of an exciplex between the host and the guest can be avoided. Therefore, the efficiency and driving durability of the organic light-emitting element can be improved.

Meanwhile, the driving durability of the organic light-emitting element can be additionally improved by improving the chemical stability of the host represented by the general formula [7]. Here, the host represented by the general formula [7], which is an aromatic hydrocarbon compound and has high stability, is particularly preferably such that all of its carbon atoms are $sp^2$ carbon atoms.

This is because a double bond in which only an $sp^2$ carbon atom is involved is a stronger bond than a single bond. It should be noted that bonds bonding the respective skeletons $Ar_1$ to $Ar_4$ are each a single bond in form but the bond is more stable than an ordinary single bond. This is because of the following reason: molecular design is performed so that conjugation may be extended between skeletons, and hence a bond between the skeletons is provided with a double-bond character.

It should be noted that the carbon atom at the 9-position of the fluorene skeleton, the carbon atom at the 13-position of the indeno[2,1-a]phenanthrene skeleton, and the carbon atom at the 12-position of the indeno[1,2-b]phenanthrene skeleton, the carbon atoms being each substituted with two methyl groups, are each an $sp^3$ carbon atom. However, these skeletons each have relatively low stability because these $sp^3$ carbon atoms can form only single bonds. In addition, none of those $sp^3$ carbon atoms affects the conjugation length of the entire molecule.

In view of the foregoing, the substituent $Ar_1$ represented in the general formula [7] is particularly preferably selected from the substituent group α1 (preferably the substituent group α2). In addition, the substituents $Ar_2$ and $Ar_3$ represented in the general formula [7] are each particularly preferably selected from the substituent group β1 (preferably the substituent group β2). The substituent $Ar_4$ represented in the general formula [7] is particularly preferably selected from the substituent group γ1 (preferably the substituent group γ2).

Specific structural formulae of the hydrocarbon compound to be incorporated as the host into the organic light-emitting element of the present invention are exemplified below. However, the present invention is not limited thereto.

[Group A]
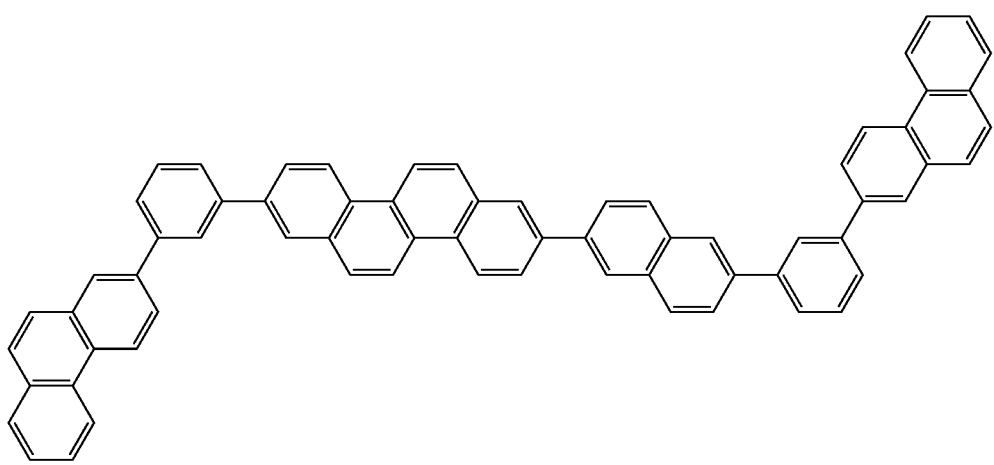
A-101
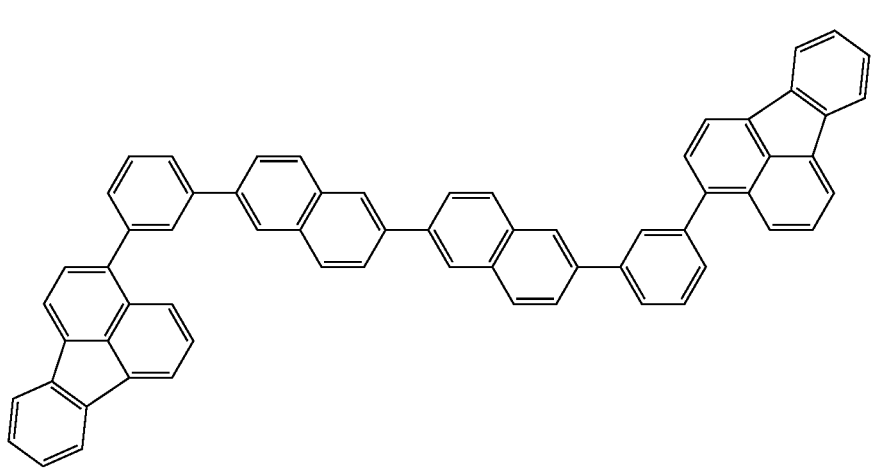
A-102
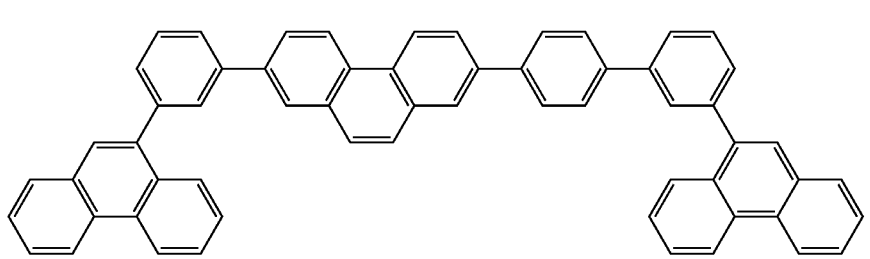
A-103
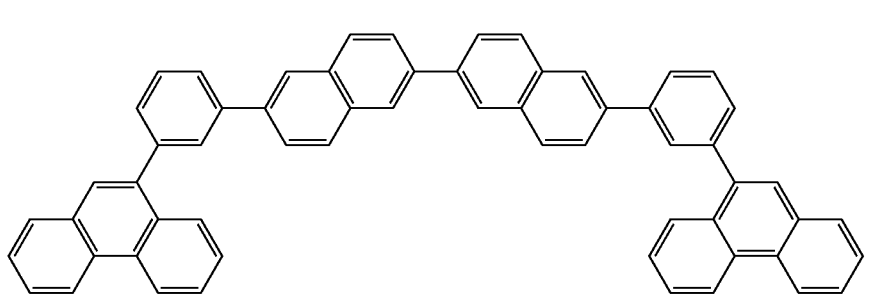
A-104

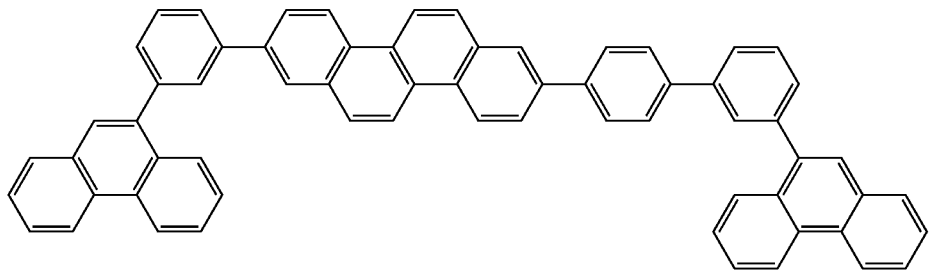
A-105
[Group B]
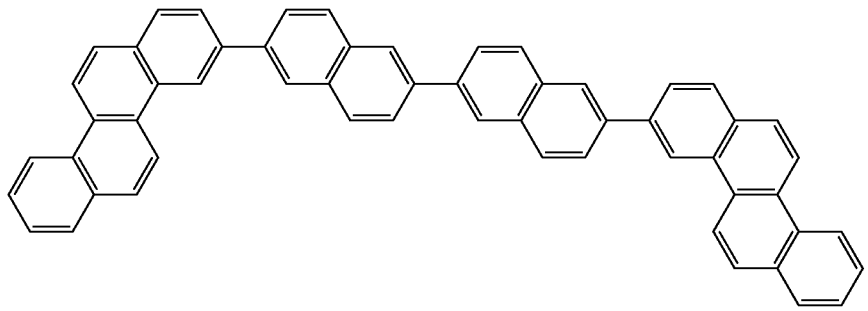
B-101
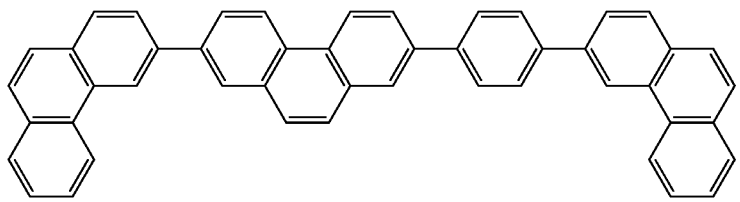
B-102
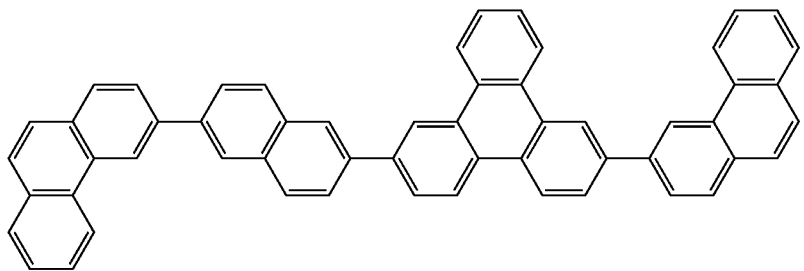
B-103
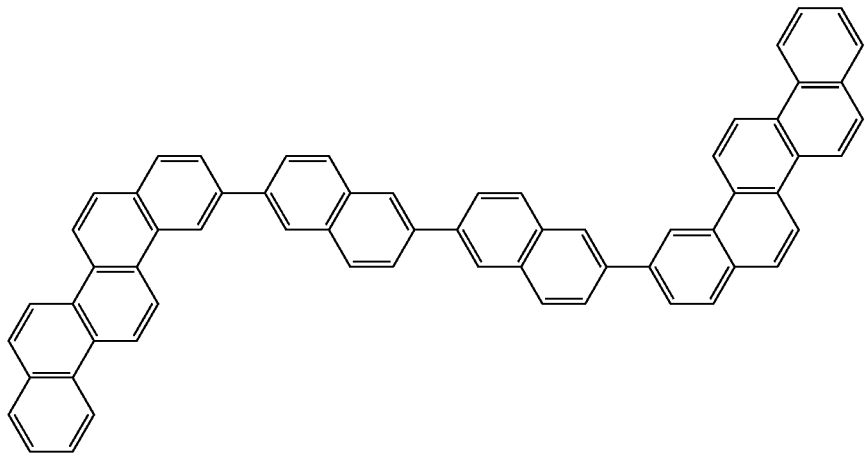
B-104

-continued
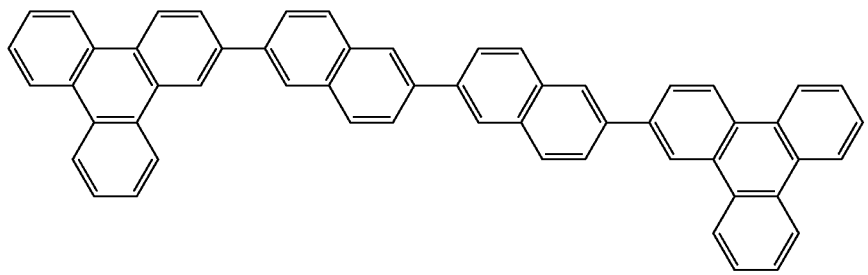
B-105
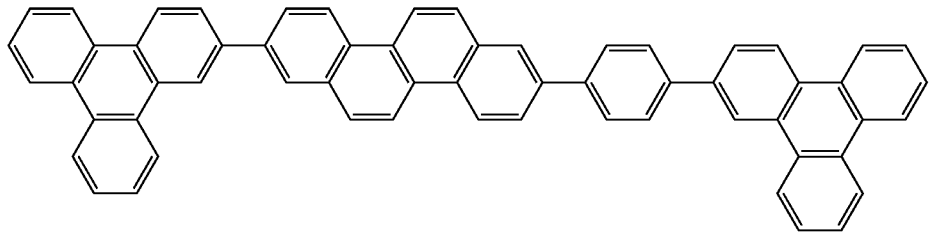
B-106
[Group C]
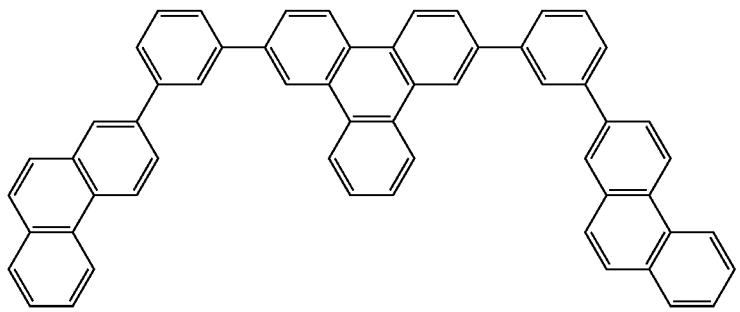
C-101
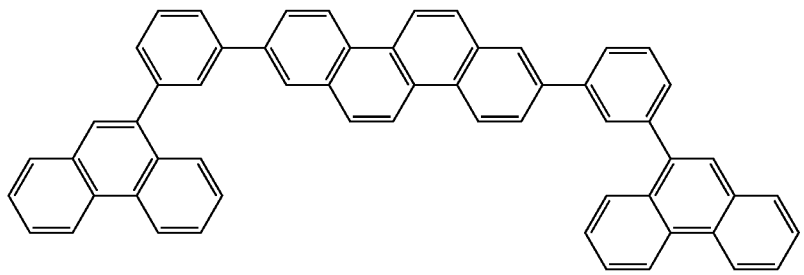
C-102
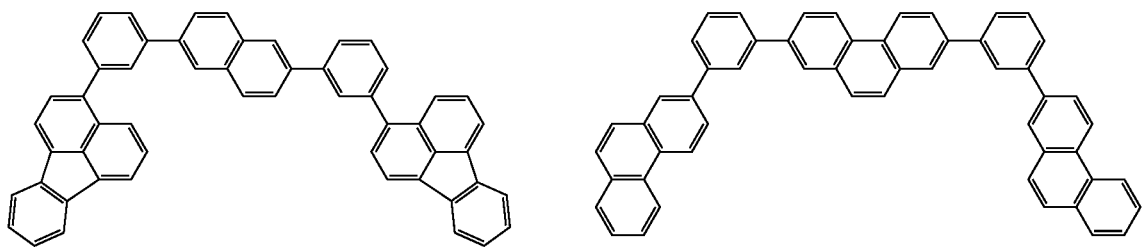
C-103      C-104

C-105
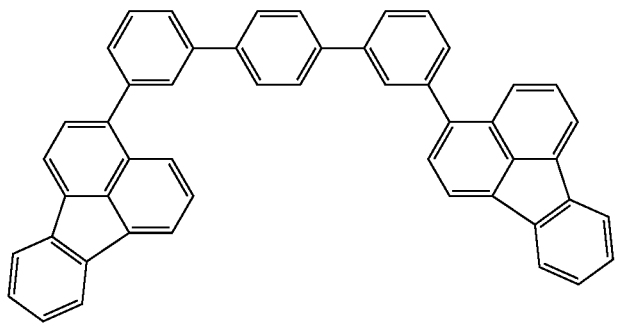
[Group D]
D-101
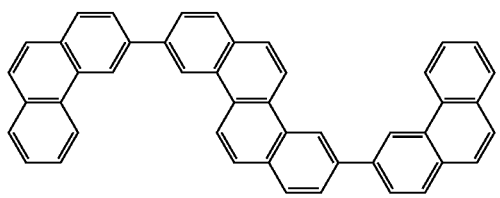
D-102
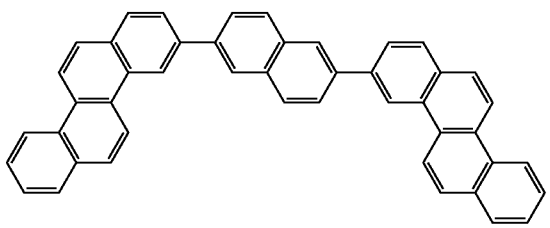
D-103
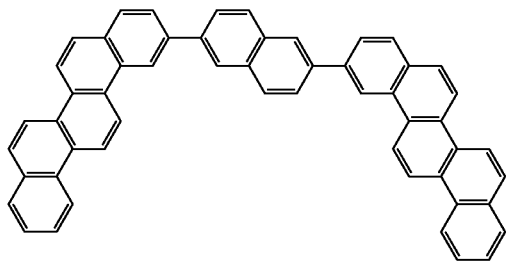
D-104
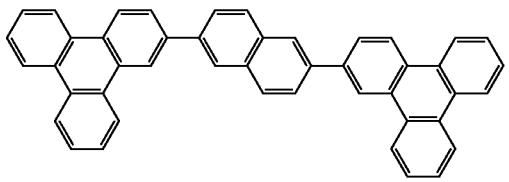
D-105
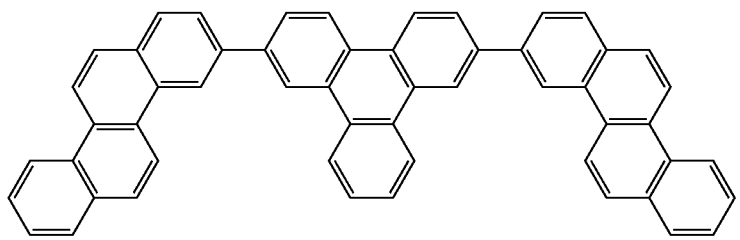
[Group E]
E-101
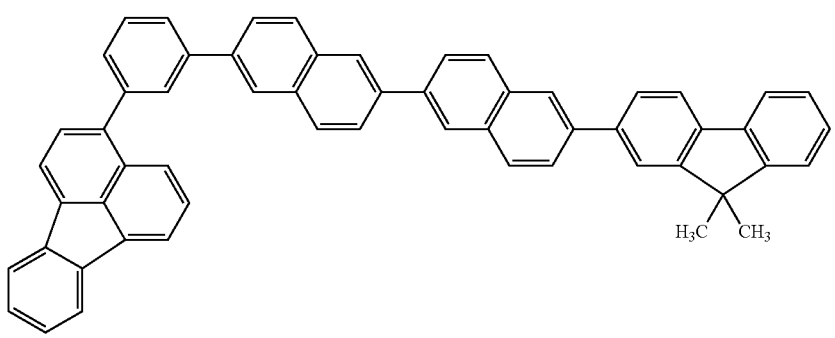

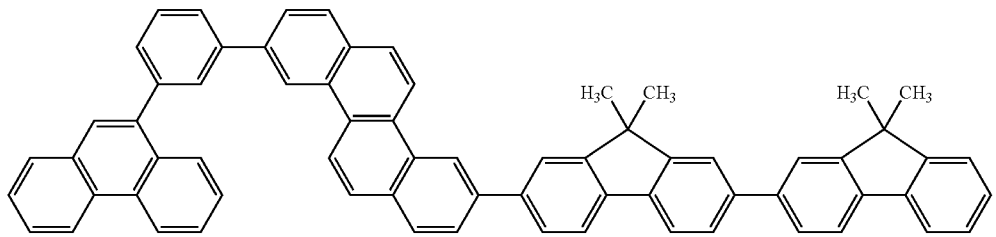
E-102
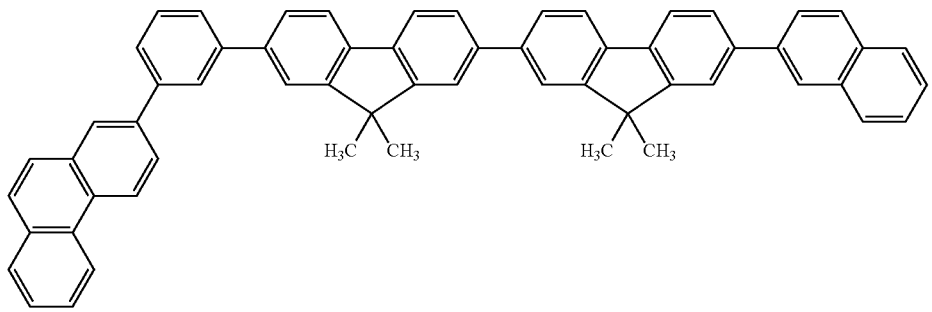
E-103
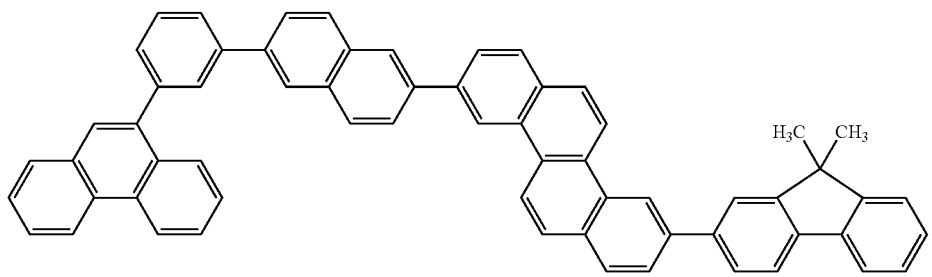
E-104
[Group F]
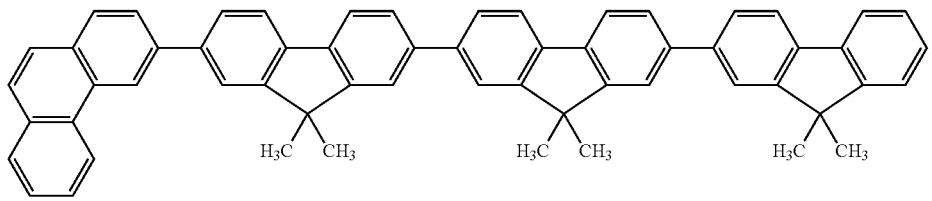
F-101
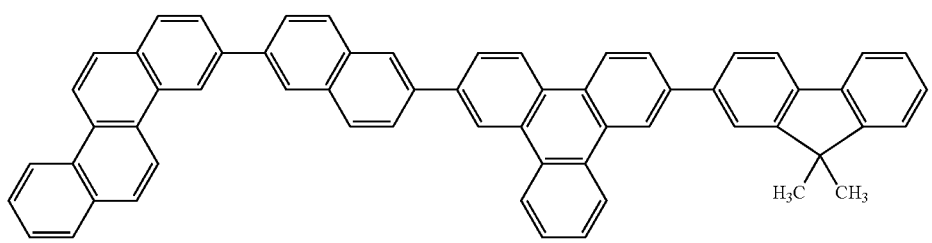
F-102

-continued
F-103
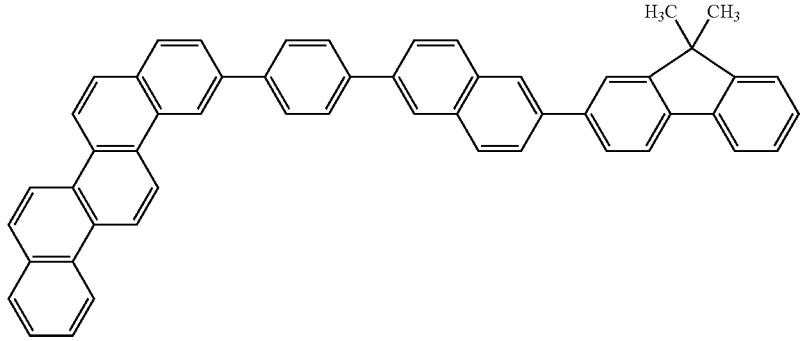
F-104
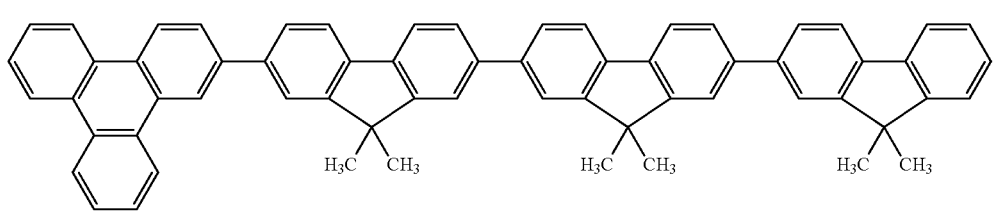
F-105
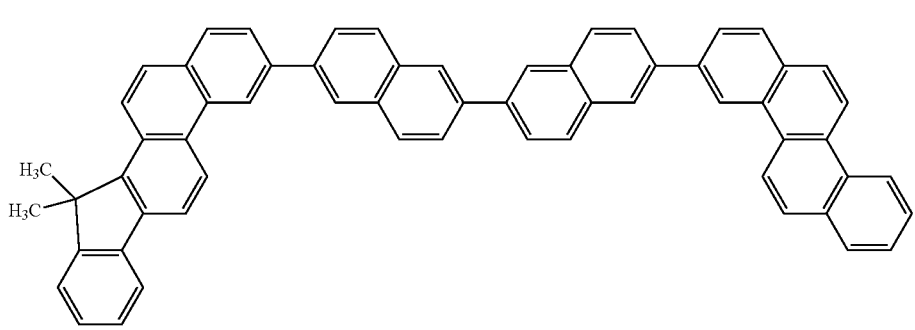
F-106
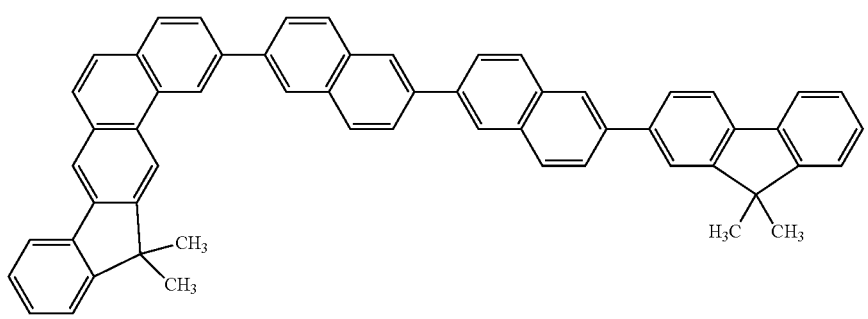
[Group G]
G-101
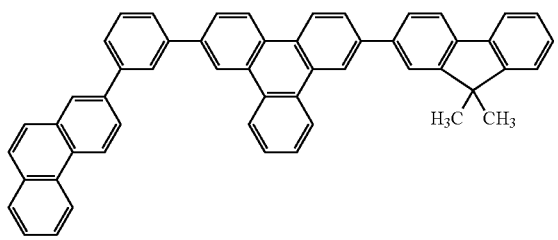
G-102

-continued
G-103
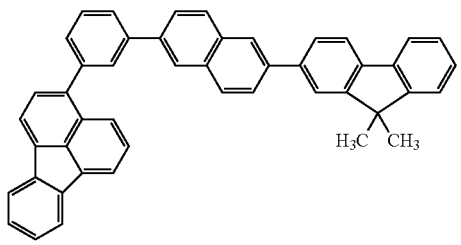
G-104
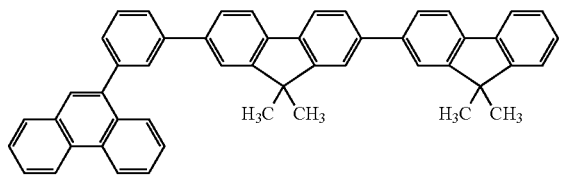
[Group H]
H-101
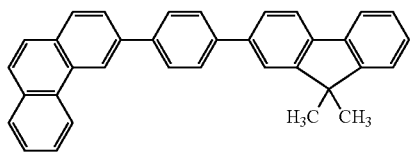
H-102
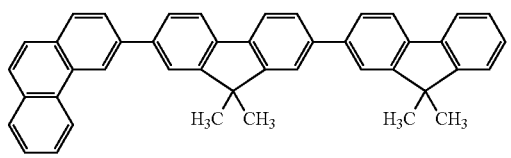
H-103
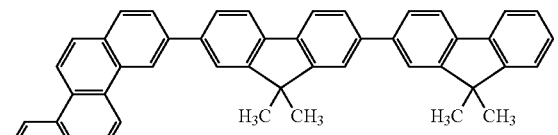
H-104
H-105
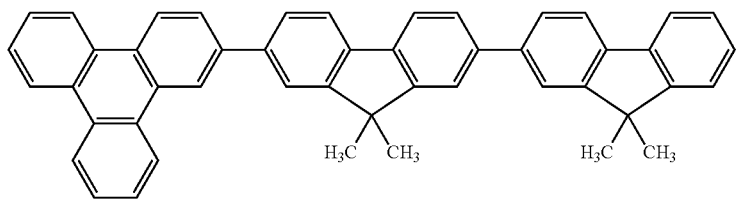
H-106
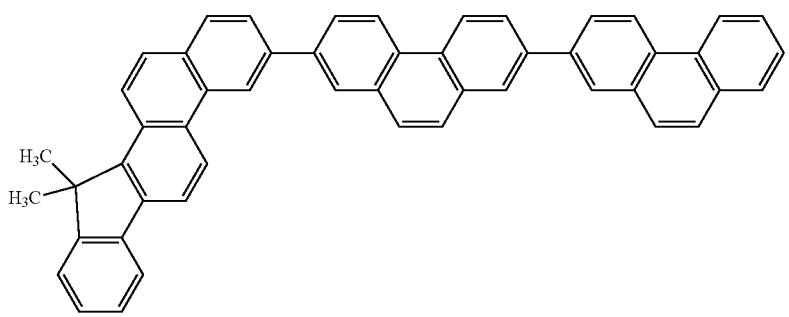
H-107
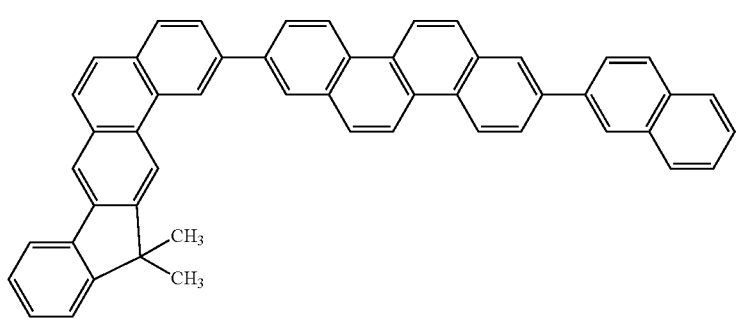

[Group I]
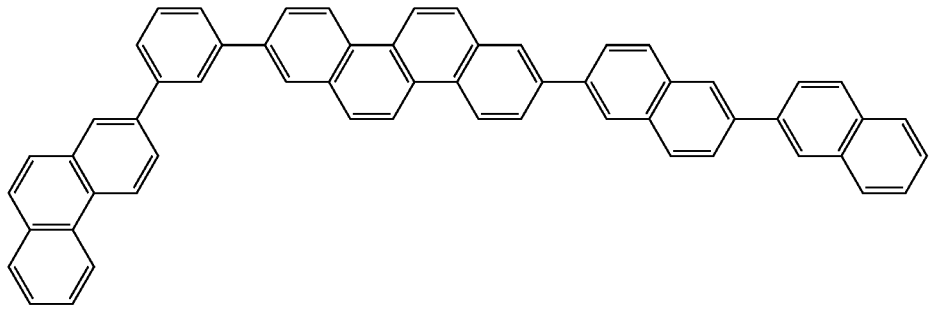
I-101
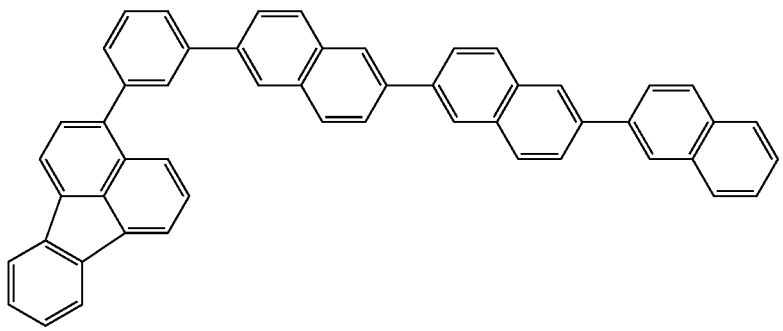
I-102
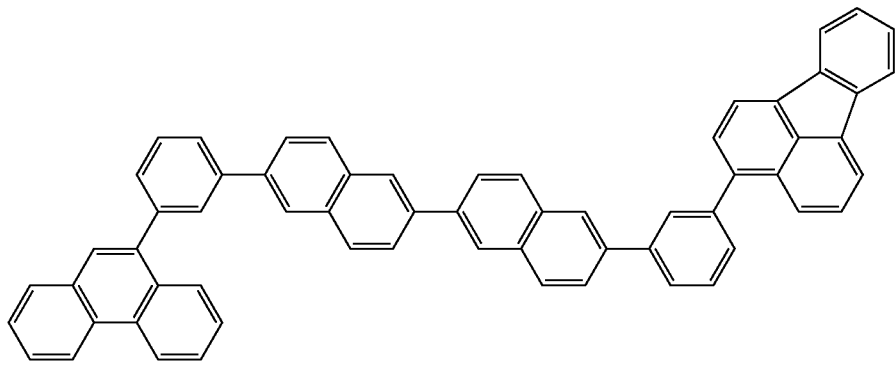
I-103
[Group J]
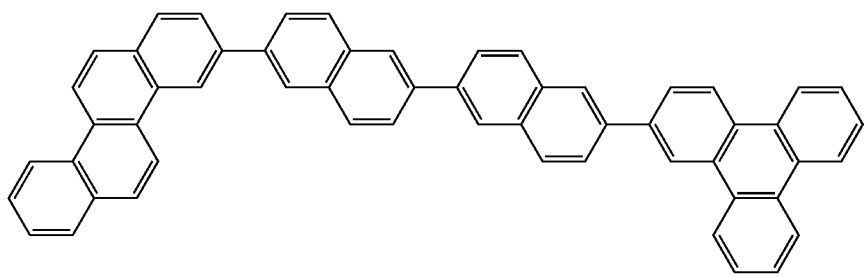
J-101
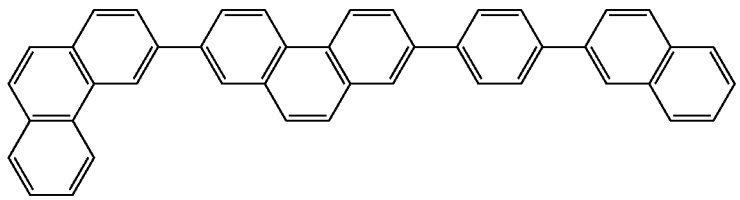
J-102

J-103
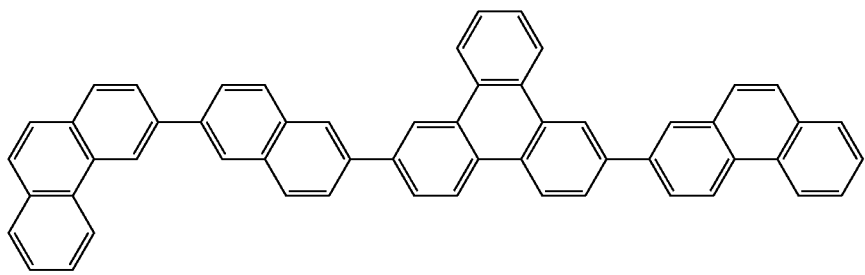
J-104
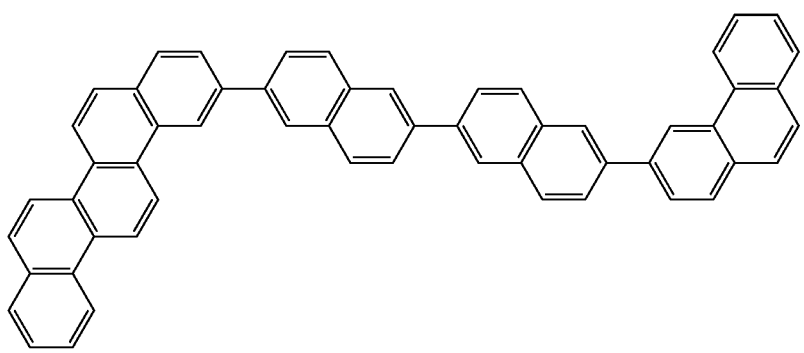
J-105
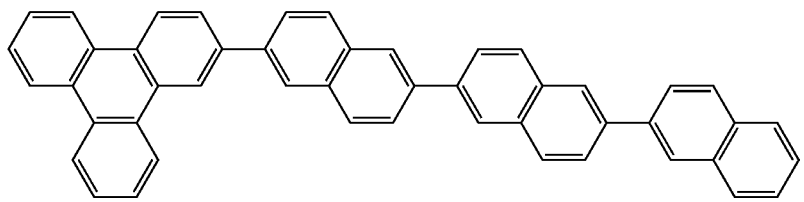
[Group K]
K-101
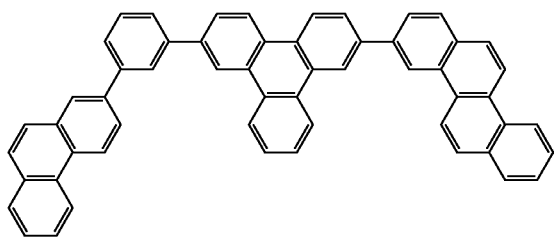
K-102
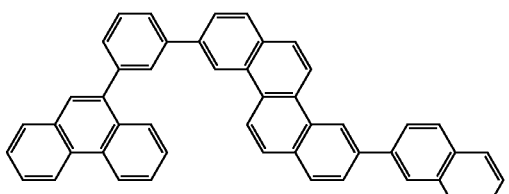
K-103
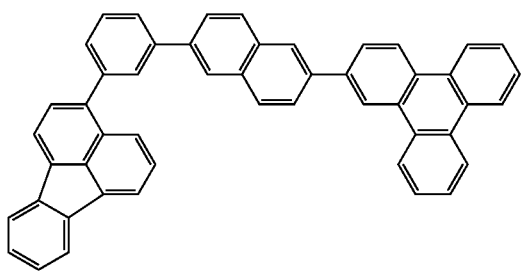
K-104
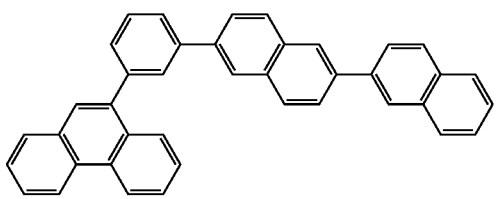

[Group L]

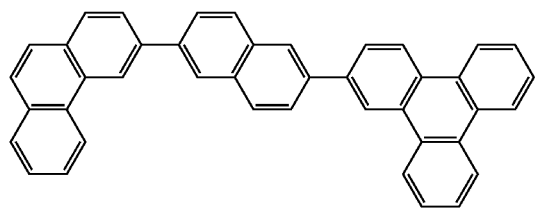
L-101

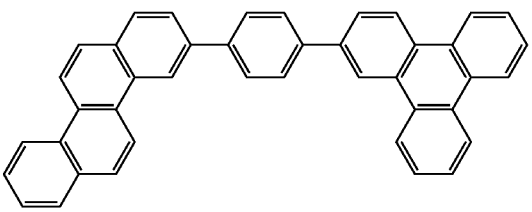
L-102

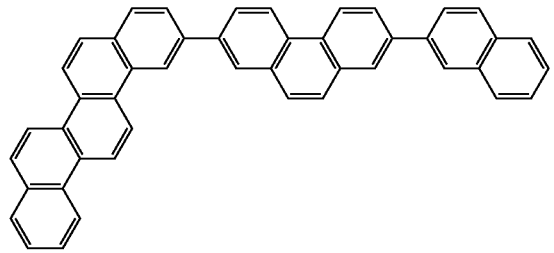
L-103

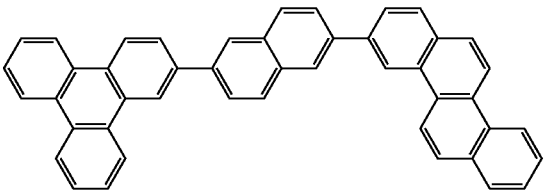
L-104

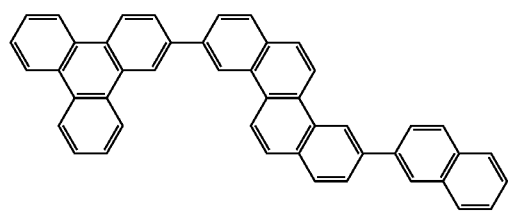
L-105

L-106

Each compound belonging to the group A has the following features (a1) to (a6):
(a1) the compound has a partial structure that forms a linear structure;
(a2) the compound has a partial structure having a major axis in a direction different from the major axis direction of the partial structure of the feature (a1);
(a3) the compound is a molecule formed only of a hydrocarbon;
(a4) the compound is a molecule formed only of an $sp^2$ carbon atom and a hydrogen atom;
(a5) p and q each represent 1; and
(a6) the compound contains a metaphenylene group.

Each compound belonging to the group A is resistant to deterioration because the compound is chemically stable and shows a small structural change by virtue of its features (a3) and (a4). In addition, each compound belonging to the group A has the feature (a6), and hence molecular orbitals are localized at $Ar_2$ and $Ar_3$, and $Ar_1$ (or $Ar_4$) becomes an unoccupied orbital. Accordingly, the extent to which the molecular orbitals overlap each other is small.

Each compound belonging to the group B has the following features (b1) to (b6):
(b1) the compound has a partial structure that forms a linear structure;
(b2) the compound has a partial structure having a major axis in a direction different from the major axis direction of the partial structure of the feature (b1);
(b3) the compound is a molecule formed only of a hydrocarbon;
(b4) the compound is a molecule formed only of an $sp^2$ carbon atom and a hydrogen atom;
(b5) p and q each represent 1; and
(b6) the compound contains a metaphenylene group.

As in each compound belonging to the group A, each compound belonging to the group B is resistant to deterioration because the compound is chemically stable and shows a small structural change by virtue of its features (b3) and (b4). In addition, each compound belonging to the group B has the feature (b6), and hence only the terminal of $Ar_1$ (or $Ar_4$) becomes an unoccupied orbital. Accordingly, its charge conductivity improves.

Each compound belonging to the group C has the following features (c1) to (c6):
(c1) the compound has a partial structure that forms a linear structure;
(c2) the compound has a partial structure having a major axis in a direction different from the major axis direction of the partial structure of the feature (c1);
(c3) the compound is a molecule formed only of a hydrocarbon;
(c4) the compound is a molecule formed only of an $sp^2$ carbon atom and a hydrogen atom;
(c5) p represents 0 and q represents 1; and
(c6) the compound contains a metaphenylene group.

Each compound belonging to the group C tends to have a smaller molecular weight (be lighter) because the number of its arylene groups is smaller than that of a compound in which p and q each represent 1. In addition, the number of rotation sites of a molecule thereof reduces because the number of the arylene groups is small. Therefore, its sublimability improves and the stability of the molecule improves. In addition, each compound belonging to the group C has the feature (c6), and hence molecular orbitals are localized at $Ar_2$ and $Ar_3$, and $Ar_1$ (or $Ar_4$) becomes an unoccupied orbital. Accordingly, the extent to which the molecular orbitals overlap each other is small.

Each compound belonging to the group D has the following features (d1) to (d6):
(d1) the compound has a partial structure that forms a linear structure;
(d2) the compound has a partial structure having a major axis in a direction different from the major axis direction of the partial structure of the feature (d1);
(d3) the compound is a molecule formed only of a hydrocarbon;
(d4) the compound is a molecule formed only of an $sp^2$ carbon atom and a hydrogen atom;
(d5) p represents 0 and q represents 1; and
(d6) the compound does not contain a metaphenylene group.

Each compound belonging to the group D tends to have a smaller molecular weight (be lighter) because the number of its arylene groups is smaller than that of a compound in which p and q each represent 1. In addition, the number of rotation sites of a molecule thereof reduces because the number of the arylene groups is small. Therefore, its sublimability improves and the stability of the molecule improves. In addition, each compound belonging to the group D has the feature (d6), and hence only the terminal of $Ar_1$ (or $Ar_4$) becomes an unoccupied orbital. Accordingly, its charge conductivity improves.

Each compound belonging to the group E has the following features (e1) to (e6):
(e1) the compound has a partial structure that forms a linear structure;
(e2) the compound has a partial structure having a major axis in a direction different from the major axis direction of the partial structure of the feature (e1);
(e3) $Ar_1$ and $Ar_4$ are different from each other;
(e4) the compound is a molecule formed only of a hydrocarbon;
(e5) p and q each represent 1; and
(e6) the compound contains a metaphenylene group.

Each compound belonging to the group E is a material in which aryl groups at left and right terminals are different from each other, and hence the extent to which the molecules of the material overlap each other reduces. In addition, each compound belonging to the group E contains $sp^3$ carbon in a molecule thereof in some cases, and in any such case, its HOMO may be raised and its hole injection property may improve. In addition, each compound belonging to the group E has the feature (b6), and hence molecular orbitals are localized at $Ar_2$ and $Ar_3$, and $Ar_1$ (or $Ar_4$) becomes an unoccupied orbital. Accordingly, the extent to which the molecular orbitals overlap each other is small.

Each compound belonging to the group F has the following features (f1) to (f6):
(f1) the compound has a partial structure that forms a linear structure;
(f2) the compound has a partial structure having a major axis in a direction different from the major axis direction of the partial structure of the feature (f1);
(f3) $Ar_1$ and $Ar_4$ are different from each other;
(f4) the compound is a molecule formed only of a hydrocarbon;
(f5) p and q each represent 1; and
(f6) the compound does not contain a metaphenylene group.

Each compound belonging to the group F is a material in which aryl groups at left and right terminals are different from each other, and hence the extent to which the molecules of the material overlap each other reduces. In addition, each compound belonging to the group F contains $sp^3$ carbon in a molecule thereof in some cases, and in any such case, its HOMO may be raised and its hole injection property may improve. Further, the compound belonging to the group F has the feature (f6), and hence only the terminal of $Ar_1$ (or $Ar_4$) becomes an unoccupied orbital. Accordingly, its charge conductivity improves.

Each compound belonging to the group G has the following features (g1) to (g6):
(g1) the compound has a partial structure that forms a linear structure;
(g2) the compound has a partial structure having a major axis in a direction different from the major axis direction of the partial structure of the feature (g1);
(g3) $Ar_1$ and $Ar_4$ are different from each other;
(g4) the compound is a molecule formed only of a hydrocarbon;
(g5) p represents 1 and q represents 0; and
(g6) the compound contains a metaphenylene group.

Each compound belonging to the group G tends to have a smaller molecular weight (be lighter) because the number of its arylene groups is smaller than that of a compound in which p and q each represent 1. Therefore, its sublimability improves and the stability of the molecule improves. In addition, each compound belonging to the group G is a material in which aryl groups at left and right terminals are different from each other, and hence the extent to which the molecules of the material overlap each other reduces. In addition, each compound belonging to the group G contains $sp^3$ carbon in a molecule thereof in some cases, and in any such case, its HOMO may be raised and its hole injection property may improve. Further, each compound belonging to the group G has the feature (g6), and hence molecular orbitals are localized at $Ar_2$ and $Ar_3$, and $Ar_1$ (or $Ar_4$) becomes an unoccupied orbital. Accordingly, the extent to which the molecular orbitals overlap each other is small.

Each compound belonging to the group H has the following features (h1) to (h6):
(h1) the compound has a partial structure that forms a linear structure;
(h2) the compound has a partial structure having a major axis in a direction different from the major axis direction of the partial structure of the feature (h1);
(h3) $Ar_1$ and $Ar_4$ are different from each other;
(h4) the compound is a molecule formed only of a hydrocarbon;
(h5) p represents 1 and q represents 0; and
(h6) the compound does not contain a metaphenylene group.

Each compound belonging to the group H tends to have a smaller molecular weight (be lighter) because the number of its arylene groups is smaller than that of a compound in which p and q each represent 1. Therefore, its sublimability improves and the stability of the molecule improves. In addition, each compound belonging to the group H is a material in which aryl groups at left and right terminals are different from each other, and hence the extent to which the molecules of the material overlap each other reduces. In addition, each compound belonging to the group H contains $sp^3$ carbon in a molecule thereof in some cases, and in any such case, its HOMO may be raised and its hole injection property may improve. Further, each compound belonging to the group H has the feature (h6), and hence only the terminal of $Ar_1$ (or $Ar_4$) becomes an unoccupied orbital. Accordingly, its charge conductivity improves.

Each compound belonging to the group I has the following features (i1) to (i7):

(i1) the compound has a partial structure that forms a linear structure;
(i2) the compound has a partial structure having a major axis in a direction different from the major axis direction of the partial structure of the feature (i1);
(i3) $Ar_1$ and $Ar_4$ are different from each other;
(i4) the compound is a molecule formed only of a hydrocarbon;
(i5) the compound is a molecule formed only of an $sp^2$ carbon atom and a hydrogen atom;
(i6) p and q each represent 1; and
(i7) the compound contains a metaphenylene group.

Each compound belonging to the group I shows small structural changes in a radical state and an excited state, and is hence stable. In addition, aryl groups at left and right terminals are different from each other, and hence the extent to which the molecules of the material overlap each other reduces. In addition, each compound belonging to the group I has the feature (i7), and hence molecular orbitals are localized at $Ar_2$ and $Ar_3$, and $Ar_1$ (or $Ar_4$) becomes an unoccupied orbital. Accordingly, the extent to which the molecular orbitals overlap each other is small.

Each compound belonging to the group J has the following features (j1) to (j7):
(j1) the compound has a partial structure that forms a linear structure;
(j2) the compound has a partial structure having a major axis in a direction different from the major axis direction of the partial structure of the feature (j1);
(j3) $Ar_1$ and $Ar_4$ are different from each other;
(j4) the compound is a molecule formed only of a hydrocarbon;
(j5) the compound is a molecule formed only of an $sp^2$ carbon atom and a hydrogen atom;
(j6) p and q each represent 1; and
(j7) the compound does not contain a metaphenylene group.

As in each compound belonging to the group I, each compound belonging to the group J shows small structural changes in a radical state and an excited state, and is hence stable. In addition, aryl groups at left and right terminals are different from each other, and hence the extent to which the molecules of the material overlap each other reduces. In addition, each compound belonging to the group J has the feature (j7), and hence only the terminal of $Ar_1$ (or $Ar_4$) becomes an unoccupied orbital. Accordingly, its charge conductivity improves.

Each compound belonging to the group K has the following features (k1) to (k7):
(k1) the compound has a partial structure that forms a linear structure;
(k2) the compound has a partial structure having a major axis in a direction different from the major axis direction of the partial structure of the feature (k1);
(k3) $Ar_1$ and $Ar_4$ are different from each other;
(k4) the compound is a molecule formed only of a hydrocarbon;
(k5) the compound is a molecule formed only of an $sp^2$ carbon atom and a hydrogen atom;
(k6) p represents 1 and q represents 0; and
(k7) the compound contains a metaphenylene group.

Each compound belonging to the group K tends to have a smaller molecular weight (be lighter) because the number of its arylene groups is smaller than that of a compound in which p and q each represent 1. In addition, the number of rotation sites of a molecule thereof reduces because the number of the arylene groups is small. Therefore, its sublimability improves and the stability of the molecule improves. In addition, each compound belonging to the group K has the feature (k7), and hence molecular orbitals are localized at $Ar_2$ and $Ar_3$, and $Ar_1$ (or $Ar_4$) becomes an unoccupied orbital. Accordingly, the extent to which the molecular orbitals overlap each other is small.

Each compound belonging to the group L has the following features (l1) to (l7):
(l1) the compound has a partial structure that forms a linear structure;
(l2) the compound has a partial structure having a major axis in a direction different from the major axis direction of the partial structure of the feature (l1);
(l3) $Ar_1$ and $Ar_4$ are different from each other;
(l4) the compound is a molecule formed only of a hydrocarbon;
(l5) the compound is a molecule formed only of an $sp^2$ carbon atom and a hydrogen atom;
(l6) p represents 1 and q represents 0; and
(l7) the compound does not contain a metaphenylene group.

Each compound belonging to the group L tends to have a smaller molecular weight (be lighter) because the number of its arylene groups is smaller than that of a compound in which p and q each represent 1. In addition, the number of rotation sites of a molecule thereof reduces because the number of the arylene groups is small. Therefore, its sublimability improves and the stability of the molecule improves. In addition, each compound belonging to the group L has the feature (l7), and hence only the terminal of $Ar_1$ (or $Ar_4$) becomes an unoccupied orbital. Accordingly, its charge conductivity improves.

(8) Specific Examples of Third Component

Specific structural formulae of the third component that can be incorporated into the organic light-emitting element of the present invention are exemplified below. However, the present invention is not limited thereto.

[Group M]

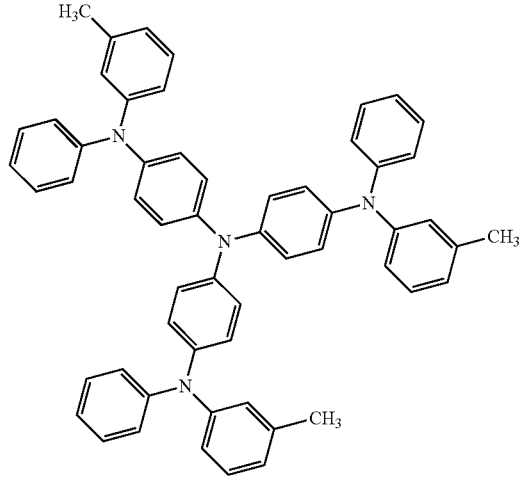

M-101

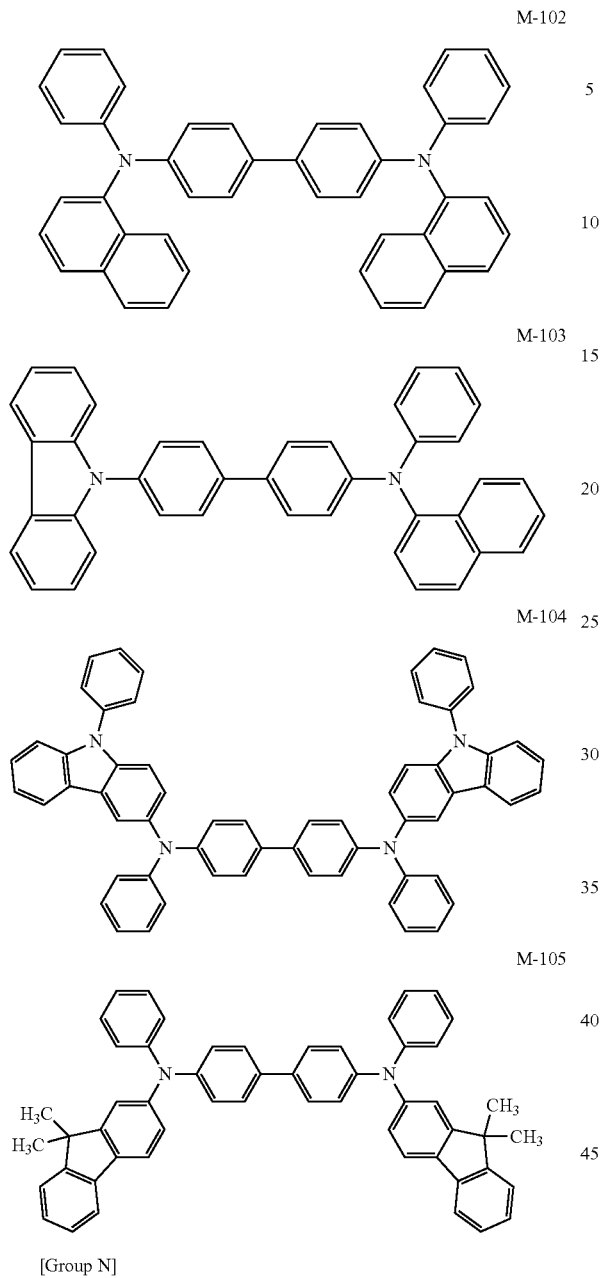
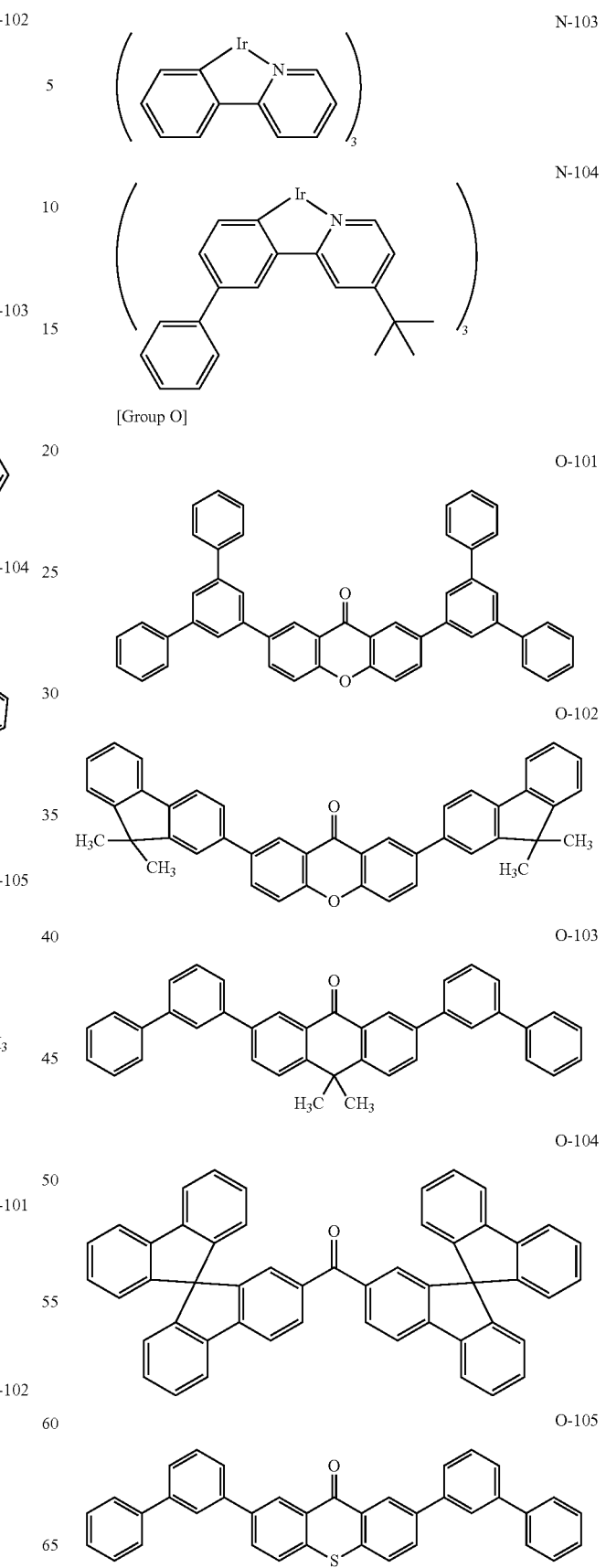

O-106

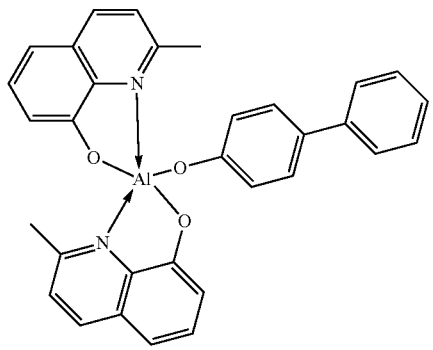

O-107

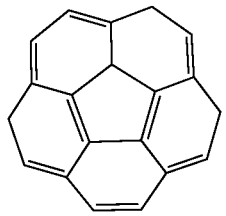

[Group P]

P-101

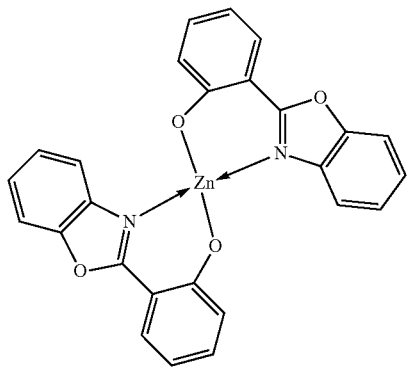

P-102

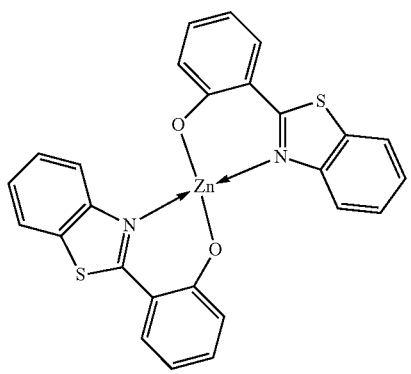

P-103

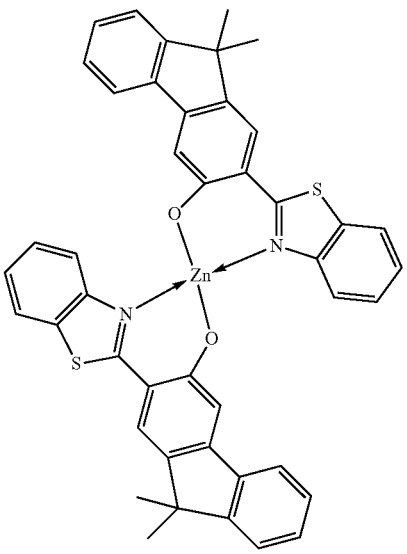

P-104

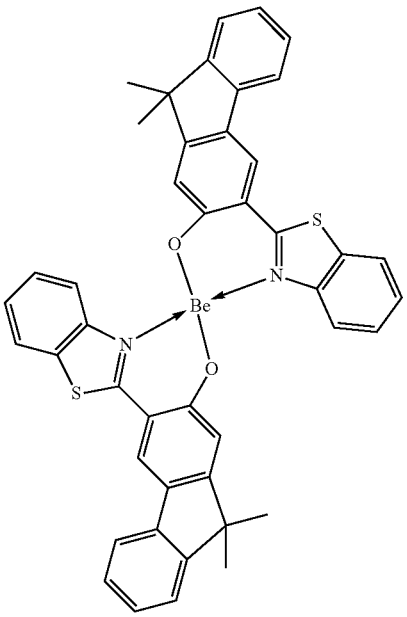

Each compound belonging to the group M is an amine-containing compound and has a high hole injection/transport ability.

Each compound belonging to the group N is a metal complex (iridium complex) and is a compound having a smaller ΔS–T value than that of the hydrocarbon compound as the host. Accordingly, the incorporation of the compound as the third component can reduce the band gap and hence improves a charge transport ability. Further, each compound belonging to the group L is a metal complex containing a heavy metal (iridium) and has a long retention time of the triplet excited state ($T_1$). Accordingly, the compound can efficiently transfer an energy obtained from the host to the light-emitting material.

The compounds belonging to the group O are a group of compounds each having the feature (2b). In addition, the compounds belonging to the group P are a group of compounds each having the feature (2c).

As described above, in the organic light-emitting element of the present invention, the organic compound layer (preferably the emission layer) contains at least the iridium complex of the present invention and the hydrocarbon compound represented by the general formula [7]. It should be noted that in the present invention, conventionally known low-molecular weight and high-molecular weight materials can each be used as required in addition to those compounds. More specifically, a hole-injectable/transportable material, a host, a light emission assist material, an electron-injectable/transportable material, or the like can be used together with the iridium complex and the hydrocarbon compound.

Examples of those materials are listed below.

The hole-injectable/transportable material is preferably a material having a high hole mobility so that the injection of a hole from the anode may be facilitated and the injected hole can be transported to the emission layer. In addition, the material is preferably a material having a high glass transition point for preventing the deterioration of film quality such as crystallization in the organic light-emitting element. Examples of the low-molecular weight and high-molecular weight materials each having hole-injecting/transporting performance include a triarylamine derivative, an arylcarbazole derivative, a phenylenediamine derivative, a stilbene derivative, a phthalocyanine derivative, a porphyrin derivative, poly(vinyl carbazole), poly(thiophene), and other conductive polymers. Further, the hole-injectable/transportable material is suitably used for the electron blocking layer as well.

Specific examples of a compound to be used as the hole-injectable/transportable material are shown below. However, the compound is of course not limited thereto.

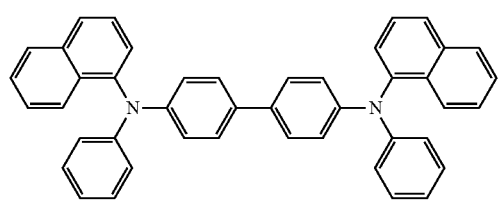

HT1

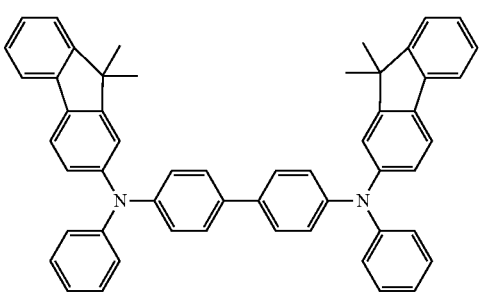

HT2

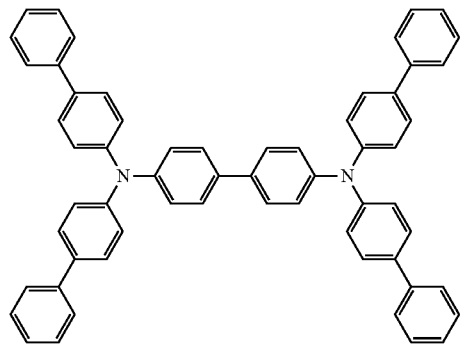

HT3

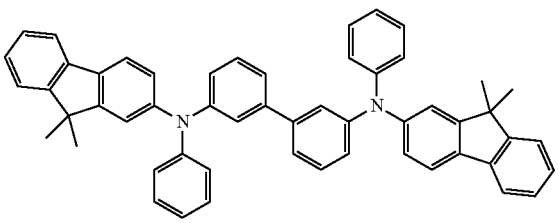

HT4

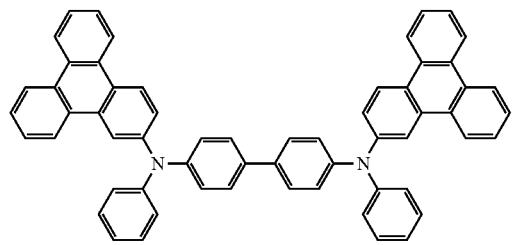

HT5

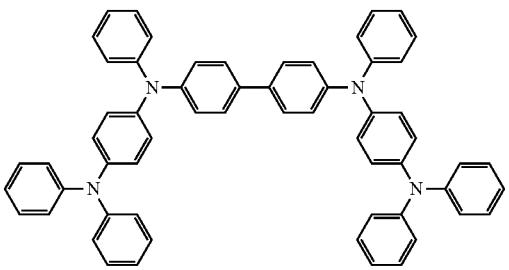

HT6

-continued
HT7
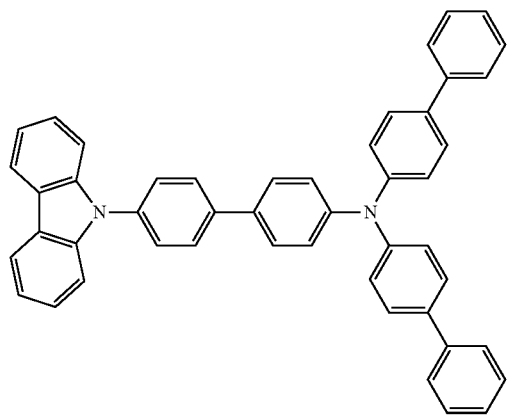
HT8
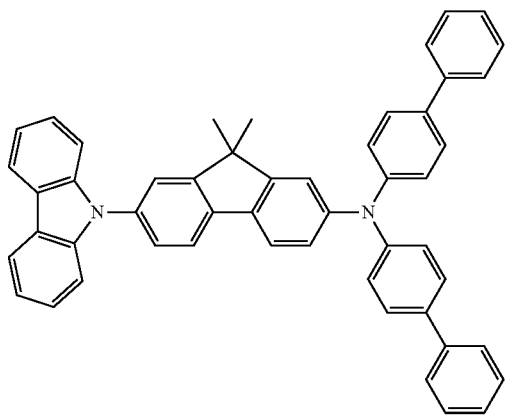
HT9
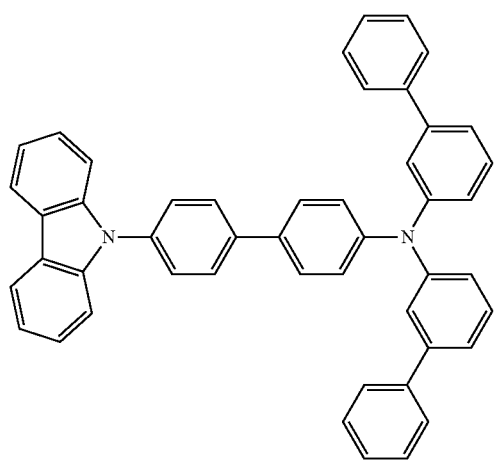
HT10
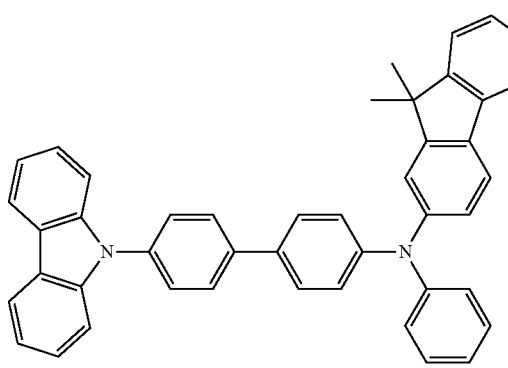
HT11
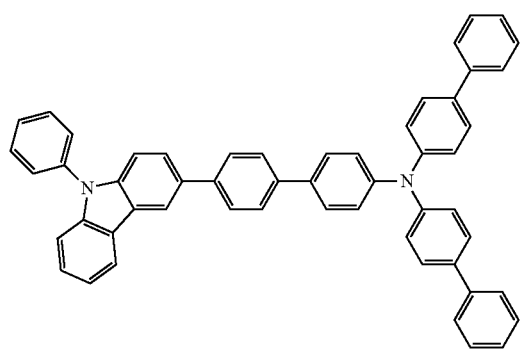
HT12
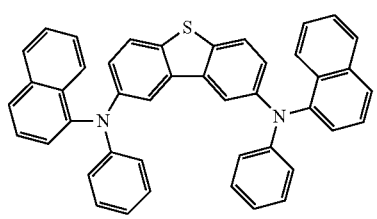

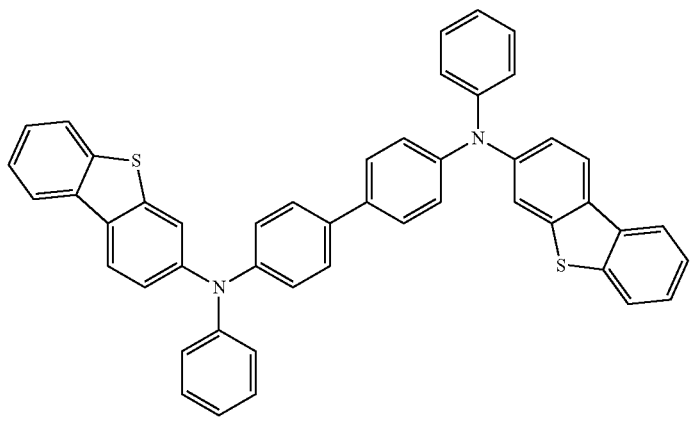

HT13

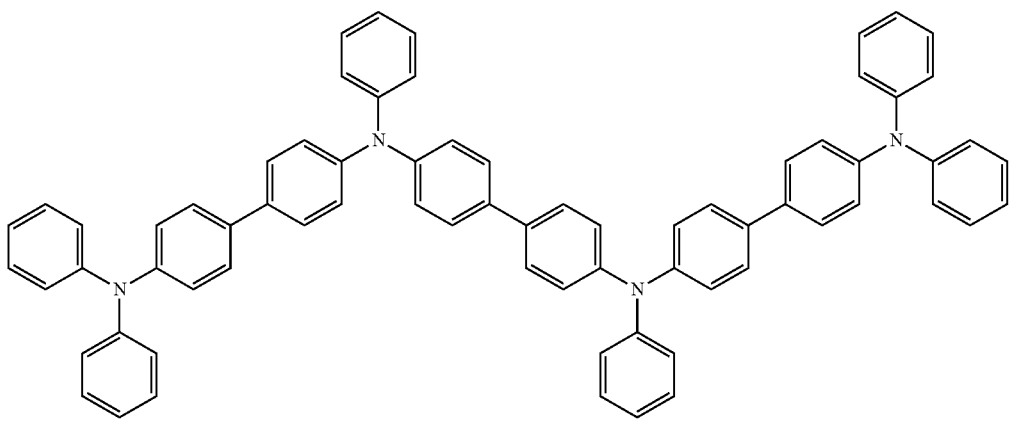

HT14

Examples of the light-emitting material mainly involved in a light-emitting function include: condensed ring compounds (such as a fluorene derivative, a naphthalene derivative, a pyrene derivative, a perylene derivative, a tetracene derivative, an anthracene derivative, and rubrene); a quinacridone derivative; a coumarin derivative; a stilbene derivative; an organic aluminum complex such as tris(8-quinolinolato)aluminum; a platinum complex; a rhenium complex; a copper complex; a europium complex; a ruthenium complex; and polymer derivatives such as a poly(phenylene vinylene) derivative, a poly(fluorene) derivative, and a poly(phenylene) derivative in addition to the iridium complex of the present invention or a derivative thereof.

Specific examples of a compound to be used as the light-emitting material are shown below. However, the compound is of course not limited thereto.

BD1

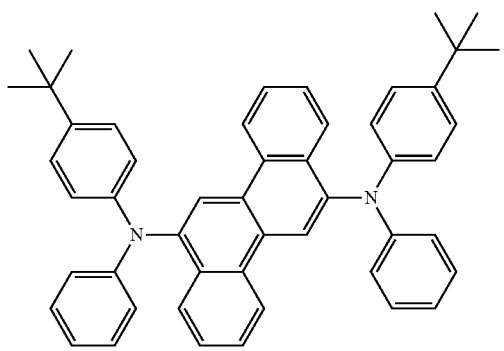

BD2

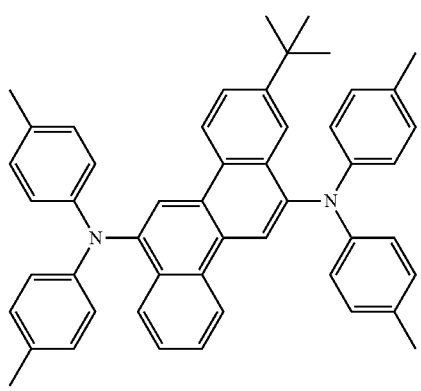

BD3

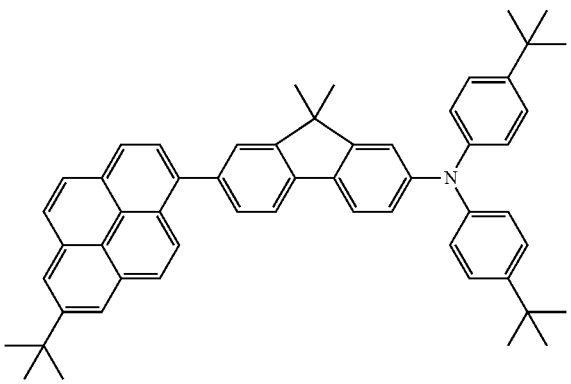

-continued
BD4
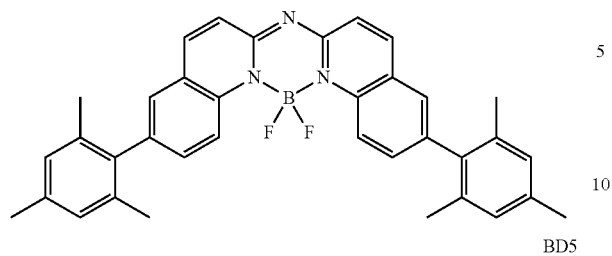
BD5
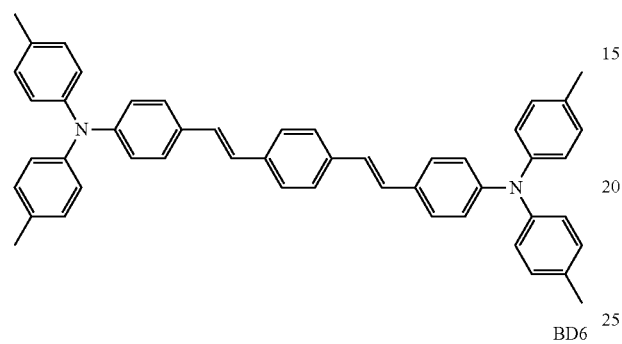
BD6
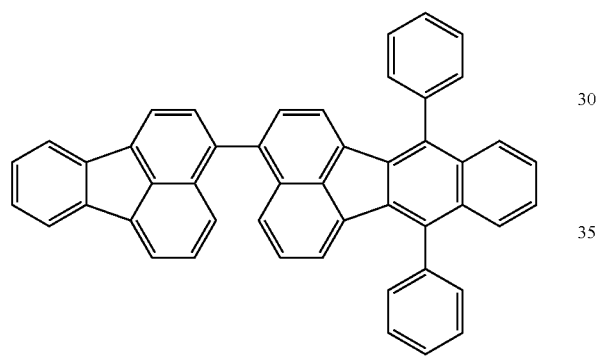
BD7
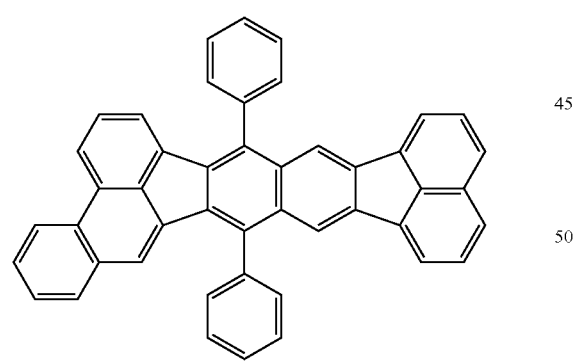
BD8
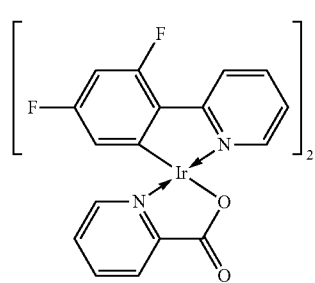
-continued
GD1
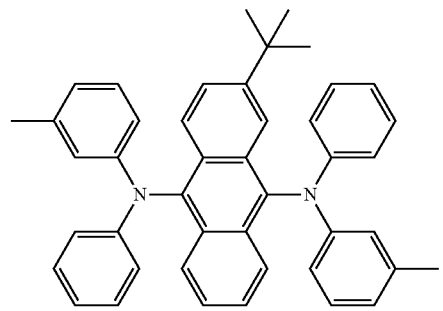
GD2
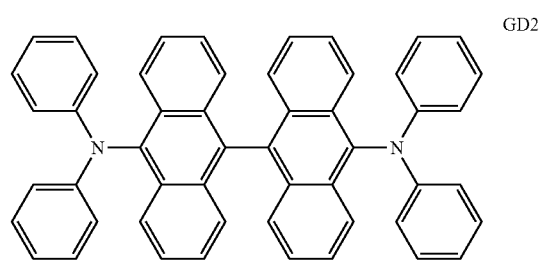
GD3
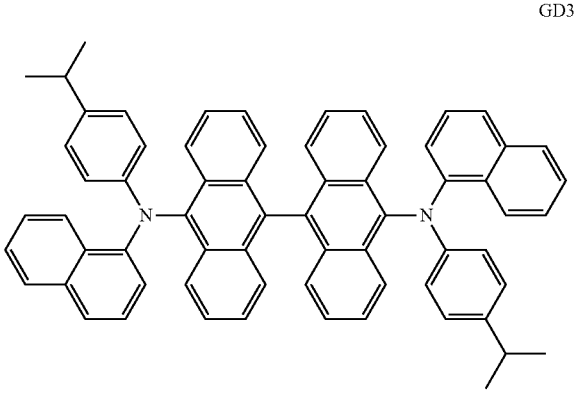
GD4
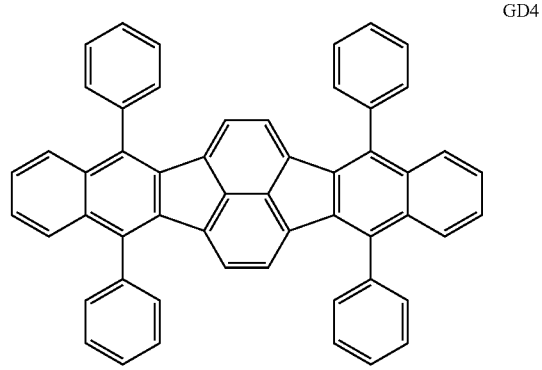

GD5
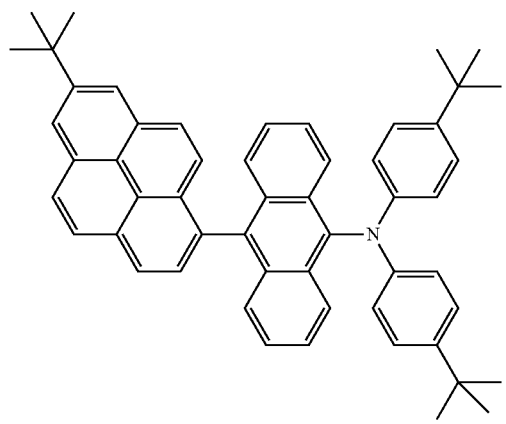
GD6
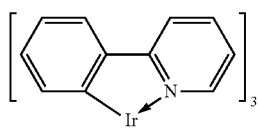
GD7
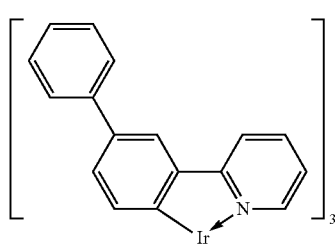
GD8
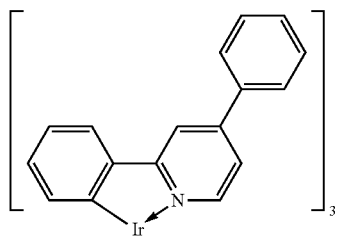
RD1
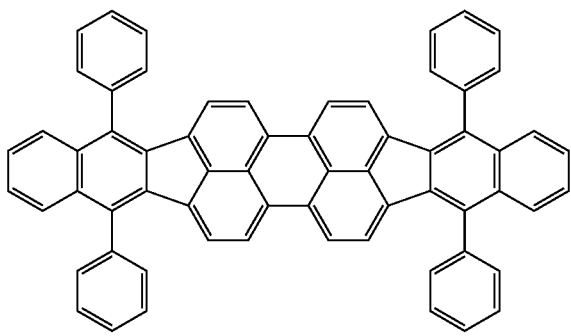
RD2
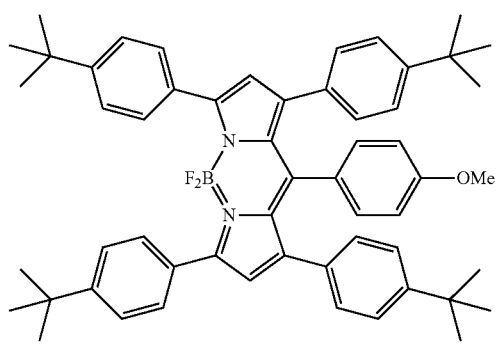
RD3
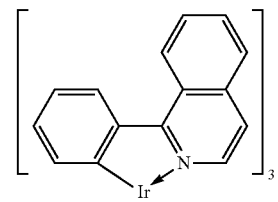
RD4
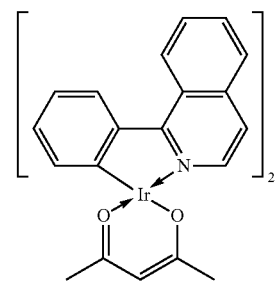
RD5
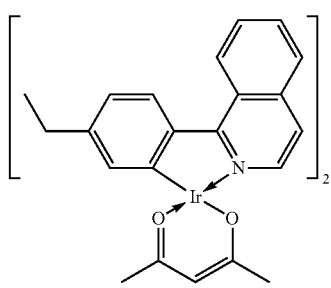

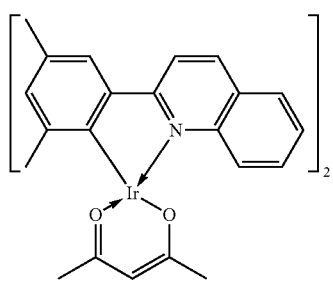

RD6

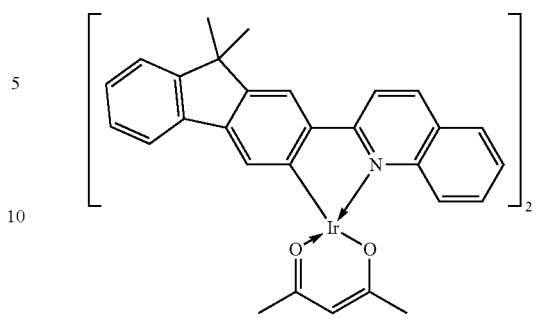

RD8

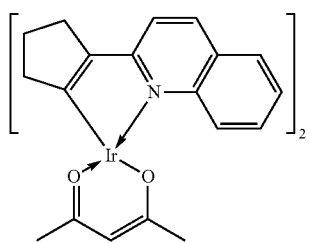

RD7

Examples of the host or assist material to be incorporated into the emission layer include: an aromatic hydrocarbon compound or a derivative thereof; a carbazole derivative; a dibenzofuran derivative; a dibenzothiophene derivative; an organic aluminum complex such as tris(8-quinolinolato) aluminum; and an organic beryllium complex in addition to the hydrocarbon compound represented by the general formula [5].

Specific examples of a compound to be used as the host or assist material to be incorporated into the emission layer are shown below. However, the compound is of course not limited thereto.

EM1

EM2

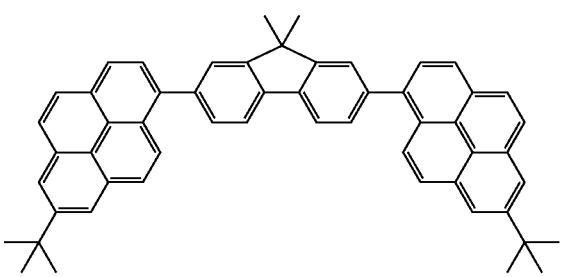

EM3

EM4

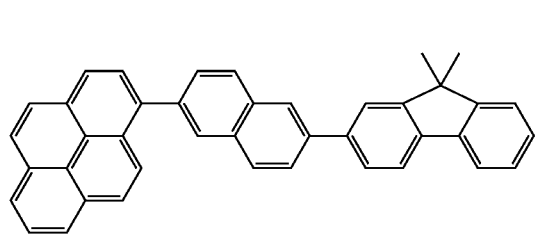
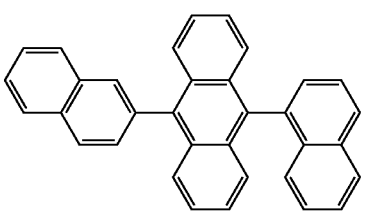

EM5

EM6

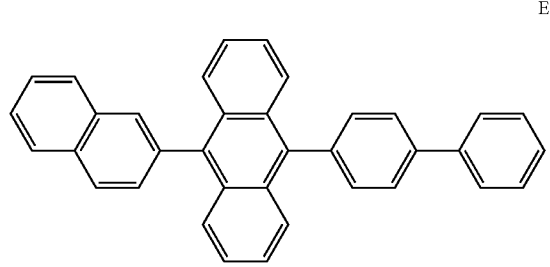
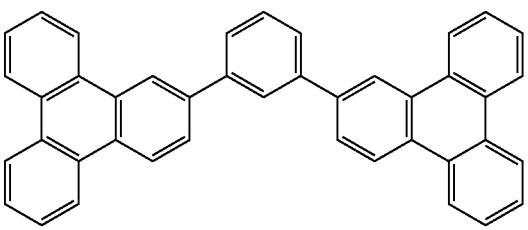

EM7
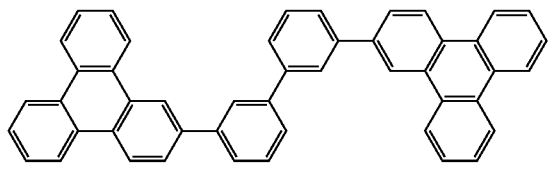
EM8
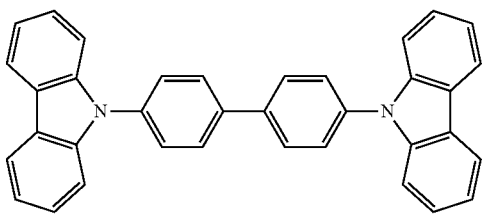
EM9
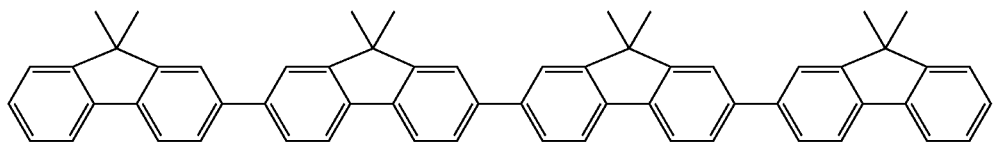
EM10
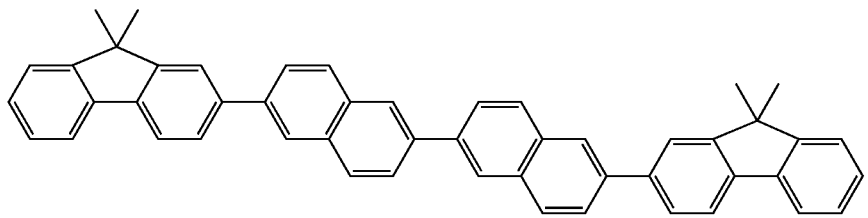
EM11
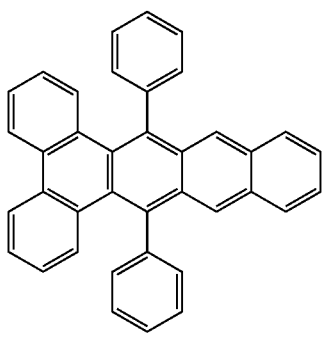
EM12
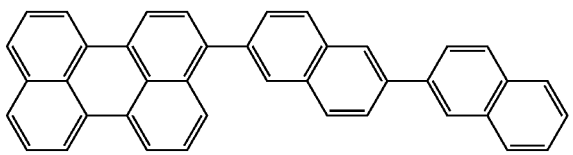
EM13
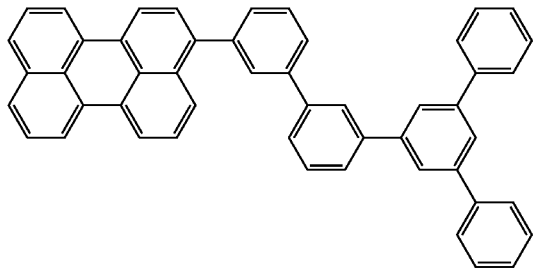
EM14
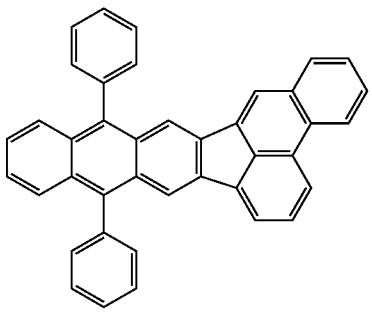
EM15
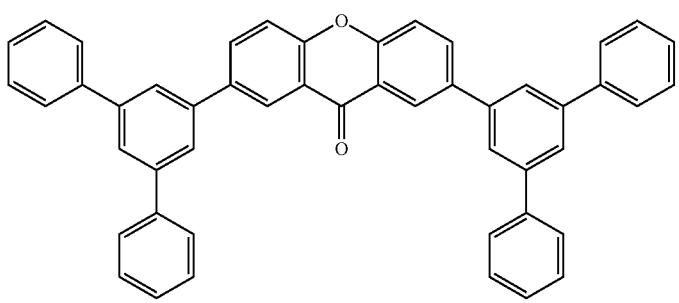

-continued

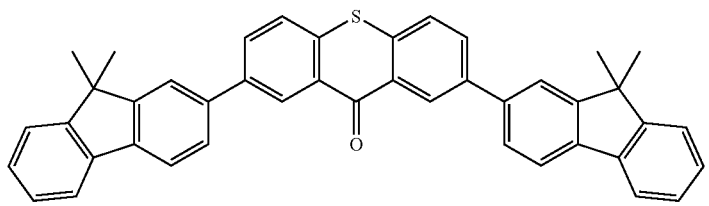
EM16

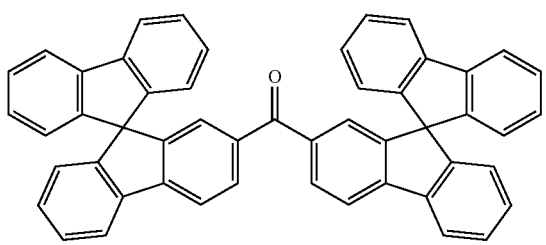
EM17

The electron-injectable/transportable material can be arbitrarily selected from materials that allow electrons to be easily injected from the cathode and can transport the injected electrons to the emission layer in consideration of, for example, the balance with the hole mobility of the hole-transportable material. Examples of the material having electron-injecting performance and electron-transporting performance include an oxadiazole derivative, an oxazole derivative, a pyrazine derivative, a triazole derivative, a triazine derivative, a quinoline derivative, a quinoxaline derivative, a phenanthroline derivative, and an organic aluminum complex. Further, the electron-injectable/transportable material is suitably used for the hole blocking layer as well.

Specific examples of a compound to be used as the electron-injectable/transportable material are shown below. However, the compound is of course not limited thereto.

-continued

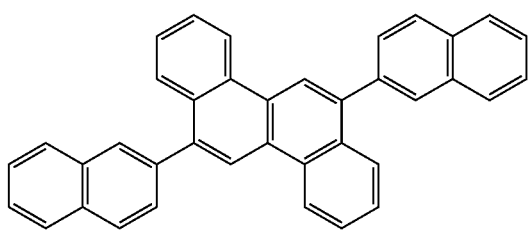
ET3

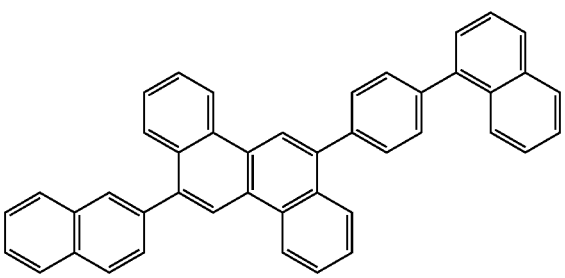
ET4

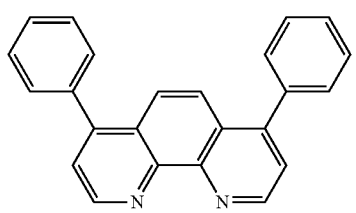
ET1

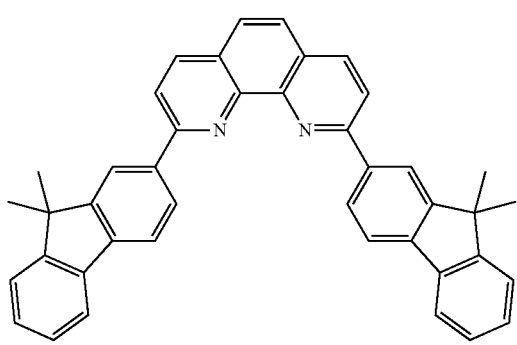
ET2

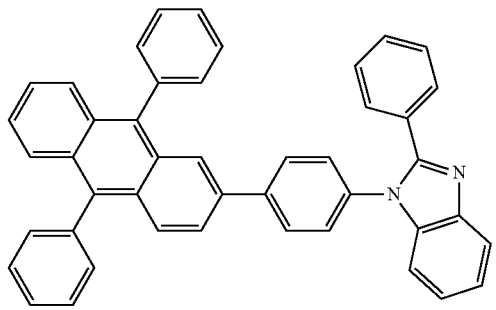
ET5

ET6

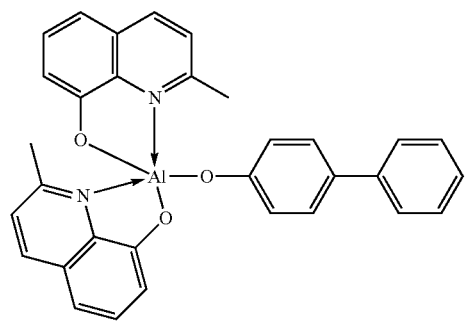

ET7

ET8

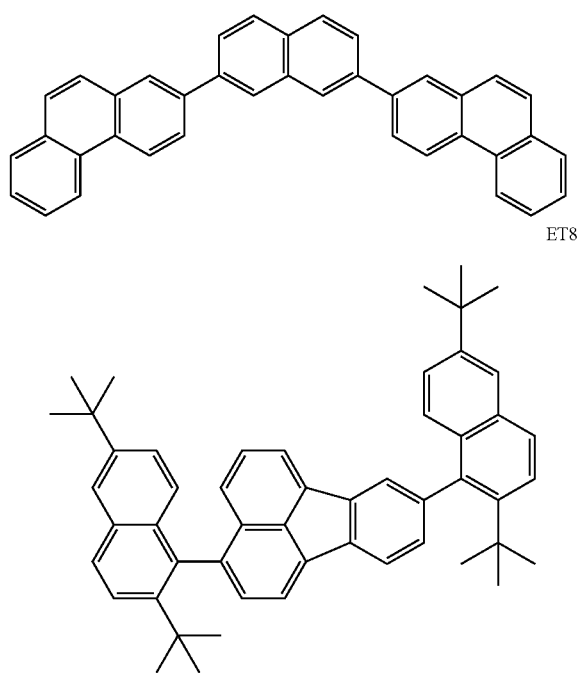

In addition, a mixture obtained by mixing the electron-injectable/transportable material and a compound of an alkali metal or an alkaline earth metal may be used as the electron-injectable/transportable material. Examples of the metal compound to be mixed with the electron-injectable/transportable material include LiF, KF, $Cs_2CO_3$, and CsF.

A constituent material for the anode desirably has as large a work function as possible. For example, there can be used: metal simple substances such as gold, platinum, silver, copper, nickel, palladium, cobalt, selenium, vanadium, and tungsten or alloys obtained by combining these metal simple substances; metal oxides such as tin oxide, zinc oxide, indium oxide, indium tin oxide (ITO), and indium zinc oxide; and conductive polymers such as polyaniline, polypyrrole, and polythiophene.

One kind of those electrode substances may be used alone, or two or more kinds thereof may be used in combination. In addition, the anode may be of a single-layer construction or may be of a multilayer construction.

On the other hand, a constituent material for the cathode desirably has as small a work function as possible. Examples thereof include: alkali metals such as lithium; alkaline earth metals such as calcium; and metal simple substances such as aluminum, titanium, manganese, silver, lead, and chromium. Alternatively, alloys obtained by combining those metal simple substances can be used. For example, a magnesium-silver alloy, an aluminum-lithium alloy, or an aluminum-magnesium alloy can be used. A metal oxide such as indium tin oxide (ITO) can also be utilized. One kind of those electrode substances may be used alone, or two or more kinds thereof may be used in combination. In addition, the cathode may be of a single-layer construction or may be of a multilayer construction.

The organic compound layer (such as the hole injection layer, the hole transport layer, the electron blocking layer, the emission layer, the hole blocking layer, the electron transport layer, or the electron injection layer) for forming the organic light-emitting element of the present invention is formed by the following method.

A dry process such as a vacuum vapor deposition method, an ionized vapor deposition method, sputtering, or a plasma process can be used for the formation of the organic compound layer for forming the organic light-emitting element of the present invention. In addition, a wet process involving dissolving the constituent materials in an appropriate solvent and forming a layer by a known application method (such as spin coating, dipping, a casting method, an LB method, or an ink jet method) can be used instead of the dry process.

Here, when the layer is formed by the vacuum vapor deposition method, the solution application method, or the like, the layer hardly undergoes crystallization or the like and is excellent in stability over time. In addition, when the layer is formed by the application method, the film can be formed by using the constituent materials in combination with an appropriate binder resin.

Examples of the binder resin include, but not limited to, a polyvinyl carbazole resin, a polycarbonate resin, a polyester resin, an ABS resin, an acrylic resin, a polyimide resin, a phenol resin, an epoxy resin, a silicone resin, and a urea resin.

In addition, one kind of those binder resins may be used alone as a homopolymer or a copolymer, or two or more kinds thereof may be used as a mixture. Further, a known additive such as a plasticizer, an antioxidant, or a UV absorber may be used in combination as required.

(8) Application of Organic Light-Emitting Element of the Present Invention

The organic light-emitting element of the present invention can be used as a constituent member for a display apparatus or lighting apparatus. In addition, the element finds use in applications such as an exposure light source for an image-forming apparatus of an electrophotographic system, a backlight for a liquid crystal display apparatus, and a light-emitting apparatus including a white light source and a color filter. Examples of the color filter include filters that transmit light beams having three colors, i.e., red, green, and blue colors.

A display apparatus of the present invention includes the organic light-emitting element of the present invention in its display portion. It should be noted that the display portion includes multiple pixels.

In addition, the pixels each have the organic light-emitting element of the present invention and a transistor as an example of an active element (switching element) or amplifying element for controlling emission luminance, and the anode or cathode of the organic light-emitting element and the drain electrode or source electrode of the transistor are electrically connected to each other. Here, the display apparatus can be used as an image display apparatus for a PC or the like. The transistor is, for example, a TFT element and the TFT element is, for example, an element formed of a transparent oxide semiconductor and is provided on the insulating surface of a substrate.

The display apparatus may be an information processing apparatus that includes an image input portion for inputting image information from, for example, an area CCD, a linear CCD, or a memory card, and displays an input image on its display portion.

In addition, the display portion of an imaging apparatus or inkjet printer may have a touch panel function. The drive system of the touch panel function is not particularly limited.

In addition, the display apparatus may be used in the display portion of a multifunction printer.

A lighting apparatus is an apparatus for lighting, for example, the inside of a room. The lighting apparatus may emit light having any one of the following colors: a white color (having a color temperature of 4,200 K), a daylight color (having a color temperature of 5,000 K), and colors ranging from blue to red colors.

A lighting apparatus of the present invention includes the organic light-emitting element of the present invention and an inverter circuit connected to the organic light-emitting element. It should be noted that the lighting apparatus may further include a color filter.

An image-forming apparatus of the present invention is an image-forming apparatus including: a photosensitive member; a charging unit for charging the surface of the photosensitive member; an exposing unit for exposing the photosensitive member to form an electrostatic latent image; and a developing unit for developing the electrostatic latent image formed on the surface of the photosensitive member. Here, the exposing unit to be provided in the image-forming apparatus includes the organic light-emitting element of the present invention.

In addition, the organic light-emitting element of the present invention can be used as a constituent member for an exposing apparatus for exposing a photosensitive member. An exposing apparatus including a plurality of the organic light-emitting elements of the present invention is, for example, an exposing apparatus in which the organic light-emitting elements of the present invention are placed to form a line along a predetermined direction.

Next, the display apparatus of the present invention is described with reference to the drawing. FIG. 1 is a schematic sectional view illustrating an example of a display apparatus including an organic light-emitting element and a TFT element connected to the organic light-emitting element. It should be noted that the organic light-emitting element of the present invention is used as the organic light-emitting element constituting a display apparatus 1 of FIG. 1.

The display apparatus 1 of FIG. 1 includes a substrate 11 made of glass or the like and a moisture-proof film 12 for protecting a TFT element or organic compound layer, the film being provided on the substrate. In addition, a metal gate electrode 13 is represented by reference numeral 13, a gate insulating film 14 is represented by reference numeral 14, and a semiconductor layer is represented by reference numeral 15.

A TFT element 18 includes the semiconductor layer 15, a drain electrode 16, and a source electrode 17. An insulating film 19 is provided on the TFT element 18. An anode 21 constituting the organic light-emitting element and the source electrode 17 are connected to each other through a contact hole 20.

It should be noted that a system for the electrical connection between the electrode (anode or cathode) in the organic light-emitting element and the electrode (source electrode or drain electrode) in the TFT is not limited to the aspect illustrated in FIG. 1. In other words, one of the anode and the cathode, and one of the source electrode and drain electrode of the TFT element have only to be electrically connected to each other.

Although multiple organic compound layers are illustrated like one layer in the display apparatus 1 of FIG. 1, an organic compound layer 22 may be multiple layers. A first protective layer 24 and second protective layer 25 for suppressing the deterioration of the organic light-emitting element are provided on a cathode 23.

When the display apparatus 1 of FIG. 1 is a display apparatus that emits white light, an emission layer in the organic compound layer 22 in FIG. 1 may be a layer obtained by mixing a red light-emitting material, a green light-emitting material, and a blue light-emitting material. In addition, the layer may be a laminated emission layer obtained by laminating a layer formed of the red light-emitting material, a layer formed of the green light-emitting material, and a layer formed of the blue light-emitting material. Further, alternatively, the following aspect is permitted: the layer formed of the red light-emitting material, the layer formed of the green light-emitting material, and the layer formed of the blue light-emitting material are, for example, arranged side by side to form domains in one emission layer.

Although the transistor is used as a switching element in the display apparatus 1 of FIG. 1, an MIM element may be used instead of the transistor as the switching element.

In addition, the transistor to be used in the display apparatus 1 of FIG. 1 is not limited to a transistor using a monocrystalline silicon wafer and may be a thin-film transistor including an active layer on the insulating surface of a substrate. A thin-film transistor using monocrystalline silicon as the active layer, a thin-film transistor using non-monocrystalline silicon such as amorphous silicon or microcrystalline silicon as the active layer, or a thin-film transistor using a non-monocrystalline oxide semiconductor such as an indium zinc oxide or an indium gallium zinc oxide as the active layer is also permitted. It should be noted that the thin-film transistor is also called a TFT element.

The transistor in the display apparatus 1 of FIG. 1 may be formed in a substrate such as an Si substrate. Here, the phrase "formed in a substrate" means that the transistor is produced by processing the substrate itself such as an Si substrate. In other words, the presence of the transistor in the substrate can be regarded as follows: the substrate and the transistor are integrally formed.

Whether the transistor is provided in the substrate is selected depending on definition. In the case of, for example, a definition of about a QVGA per inch, the organic light-emitting element is preferably provided in the Si substrate.

As described above, the driving of the display apparatus using the organic light-emitting element of the present invention enables display that has good image quality and is stable over a long time period.

EXAMPLES

Hereinafter, the present invention is described by way of Examples. It should be noted that the present invention is not limited thereto.

Example 1

Synthesis of Exemplified Compound Ir-113

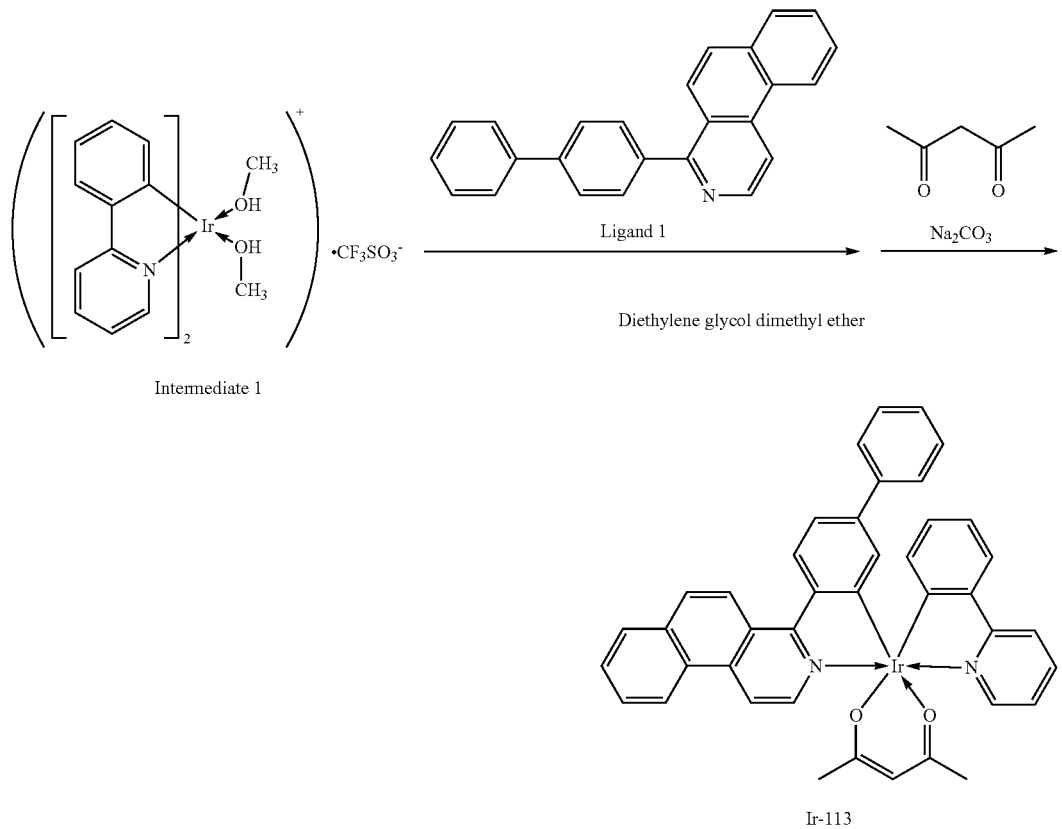

Intermediate 1

Ir-113

(1) Synthesis of Intermediate 1 and Ligand 1

Intermediate 1 was synthesized according to a method described in PTL 2. In addition, Ligand 1 was synthesized according to a method described in PTL 3.

(2) Synthesis of Exemplified Compound Ir-113

The following reagents and solvent were loaded in a 100-ml recovery flask.

Intermediate 1: 0.864 g (1.21 mmol)
Ligand 1: 0.802 g (2.42 mmol)
Diethylene glycol dimethyl ether: 50 ml Next, the reaction solution was heated to 160° C. under nitrogen. After that, the reaction solution was stirred at the temperature (160° C.) for 6 hours. At this time, the color of the reaction solution changed from a yellow color to a dark red color. Next, the temperature of the reaction solution was reduced to 120° C. and then the following reagents were added.

Acetylacetone (manufactured by Tokyo Chemical Industry Co., Ltd.): 0.606 g (6.05 mmol)
Sodium carbonate: 0.641 g (6.05 mmol)

Next, the reaction solution was heated to 120° C. under nitrogen. After that, the reaction solution was stirred at the temperature (120° C.) for 2 hours. Next, water was added to a viscous body, which had been produced by removing the solvent of the reaction solution by distillation under reduced pressure, to precipitate a solid. Next, the solid was filtered and then vacuum-dried, followed by purification with a neutral alumina gel column (toluene:ethyl acetate=10:1). Thus, 0.160 g of Exemplified Compound Ir-113 was obtained (yield: 17%).

Matrix-assisted laser desorption/ionization time-of-flight mass spectrometry (MALDI-TOF MS, Autoflex LRF manufactured by Bruker) confirmed that the compound had an $M^+$ of 776.2.

Further, the structure of the compound was identified by $^1$H-NMR measurement.

$^1$H-NMR {$(CD_3)_2S=O$, 500 MHz} δ (ppm): 8.98-8.96 (1H, m), 8.86 (1H, d), 8.73 (1H, d), 8.60 (1H, d), 8.51 (1H, d), 8.26 (1H, d), 8.20-8.17 (3H, m), 7.99 (1H, t), 7.89-7.85 (2H, m), 7.70 (1H, d), 7.45 (1H, t), 7.36-7.33 (2H, m), 7.28-7.24 (3H, m), 7.20 (1H, dd), 6.74 (1H, t), 6.54 (1H, t), 6.48 (1H, d), 5.99 (1H, d), 5.30 (1H, s), 1.77 (3H, s), 1.70 (3H, s)

The phosphorescence spectrum of a dilute toluene solution ($1\times10^{-5}$ M) of Exemplified Compound Ir-113 was measured with an F-4500 manufactured by Hitachi, Ltd. It should be noted that the measurement was performed under the following conditions: the measurement was performed under a nitrogen atmosphere at room temperature and an excitation wavelength was set to 450 nm. As a result of the measurement, the peak wavelength of the phosphorescence spectrum was 609 nm.

The vacuum thermogravimetric analysis of Exemplified Compound Ir-113 was performed with a TG-DTA 2410SA manufactured by Bruker AXS and then its sublimation temperature ($T_{sub}$) was determined by the following procedure. First, the thermogravimetric change of the sample was measured under a vacuum of $1\times10^{-3}$ Pa. Next, the resultant measured result was substituted into the following calculation equation (i) to determine a change in saturated vapor pressure P [Pa] with temperature:

$$P = m/\{4.38 \times 10^{-3} \cdot (M/T)^{1/2}\} \quad \text{(i)}$$

(m: an evaporation rate per unit area [kg/m$^2$·s], M: the molecular weight of the complex, T: the temperature of an evaporation surface [K]).

It should be noted that m is determined from the following equation (ii):

$$m = (1/U) \cdot (d\Delta W/dt) \quad \text{(ii)}$$

(U: the area of a sample dish [m$^2$], d$\Delta$W/dt: the first derivation of a thermogravimetric curve with respect to time).

Here, a weight change rate within 20 seconds {(amount of weight change)/(20 seconds)} was used as the d$\Delta$W/dt. In addition, a temperature after a lapse of 20 seconds was used as the temperature T.

A saturated vapor pressure curve is obtained by plotting the P obtained by the calculation against the T. In the saturated vapor pressure curve, the P starts to increase immediately after the initiation of the sublimation of the complex. Here, the temperature at which the P exceeded 5×10$^{-4}$ Pa was defined as the T$_{sub}$. As a result, the T$_{sub}$ in Exemplified Compound Ir-113 was 300° C.

The atmospheric thermogravimetric/differential thermal analysis of Exemplified Compound Ir-113 was performed with a TG-DTA 2000SA manufactured by Bruker AXS. In the resultant differential thermal curve, the temperature at which an exothermic peak started to appear was defined as the decomposition temperature (T$_d$). It should be noted that a weight reduction simultaneously occurred at the T$_d$ and hence the reaction was confirmed to be a decomposition reaction. As a result, in Exemplified Compound Ir-113, the T$_d$ was 355° C.

Example 2

Synthesis of Exemplified Compound Ir-114

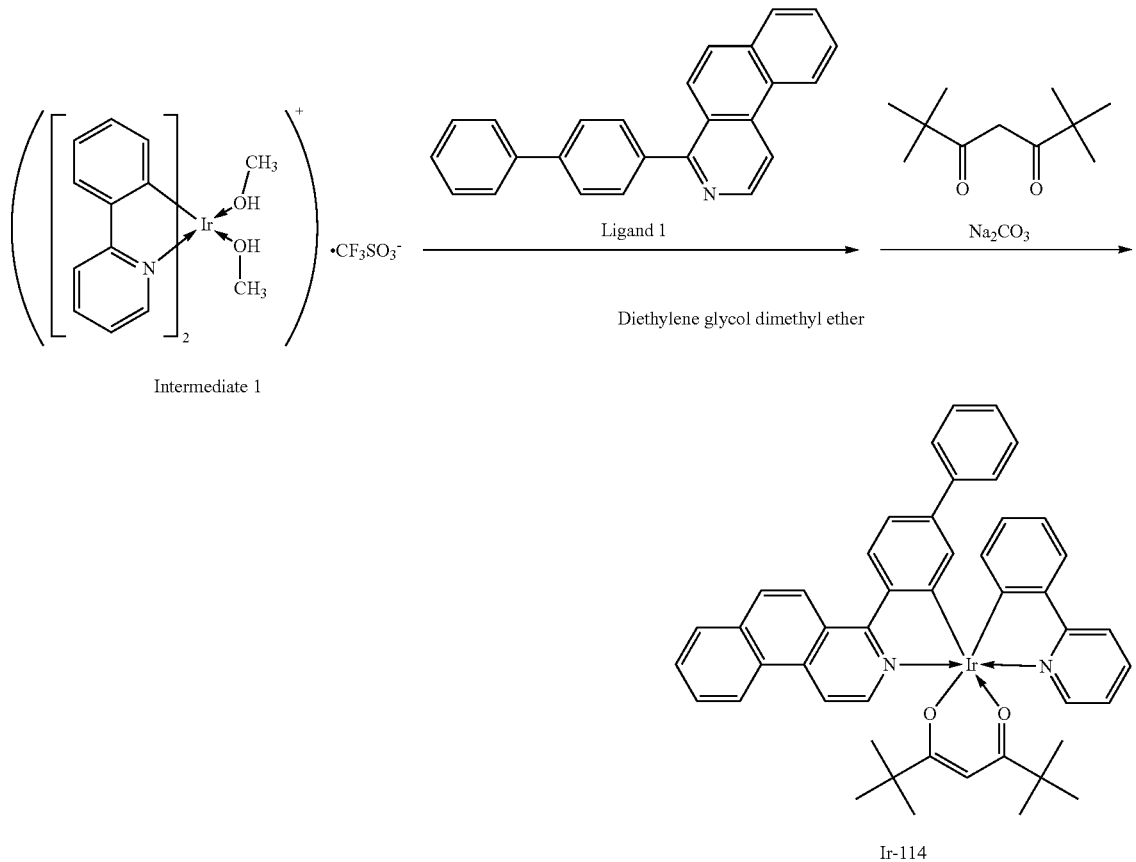

Exemplified Compound Ir-114 was obtained by the same method as that of Example 1 except that in the section (2) of Example 1, dipivaloylmethane (manufactured by Tokyo Chemical Industry Co., Ltd.) was used instead of acetylacetone.

MALDI-TOF MS confirmed that the compound had an M$^+$ of 860.3.

Further, the structure of the compound was identified by $^1$H-NMR measurement.

$^1$H-NMR {(CD$_3$)$_2$S=O, 500 MHz} δ (ppm): 8.99-8.97 (1H, m), 8.86 (1H, d), 8.70 (1H, d), 8.50 (1H, d), 8.37 (1H, d), 8.26 (1H, d), 8.19-8.15 (3H, m), 7.96 (1H, t), 7.86-7.83 (2H, m), 7.73 (1H, d), 7.40 (1H, t), 7.36-7.28 (4H, m), 7.25 (1H, t), 7.20 (1H, dd), 6.75 (1H, t), 6.58-6.55 (2H, m), 6.20 (1H, d), 5.50 (1H, s), 0.89 (9H, s), 0.77 (9H, s)

In addition, the phosphorescence spectrum of Exemplified Compound Ir-114 in a dilute toluene solution state was measured in the same manner as in Example 1. As a result, its peak wavelength was 612 nm. Further, the T$_{sub}$ of Exemplified Compound Ir-114 was determined in the same manner as in Example 1. As a result, the T$_{sub}$ was 270° C.

Example 3

Synthesis of Exemplified Compound Ir-125

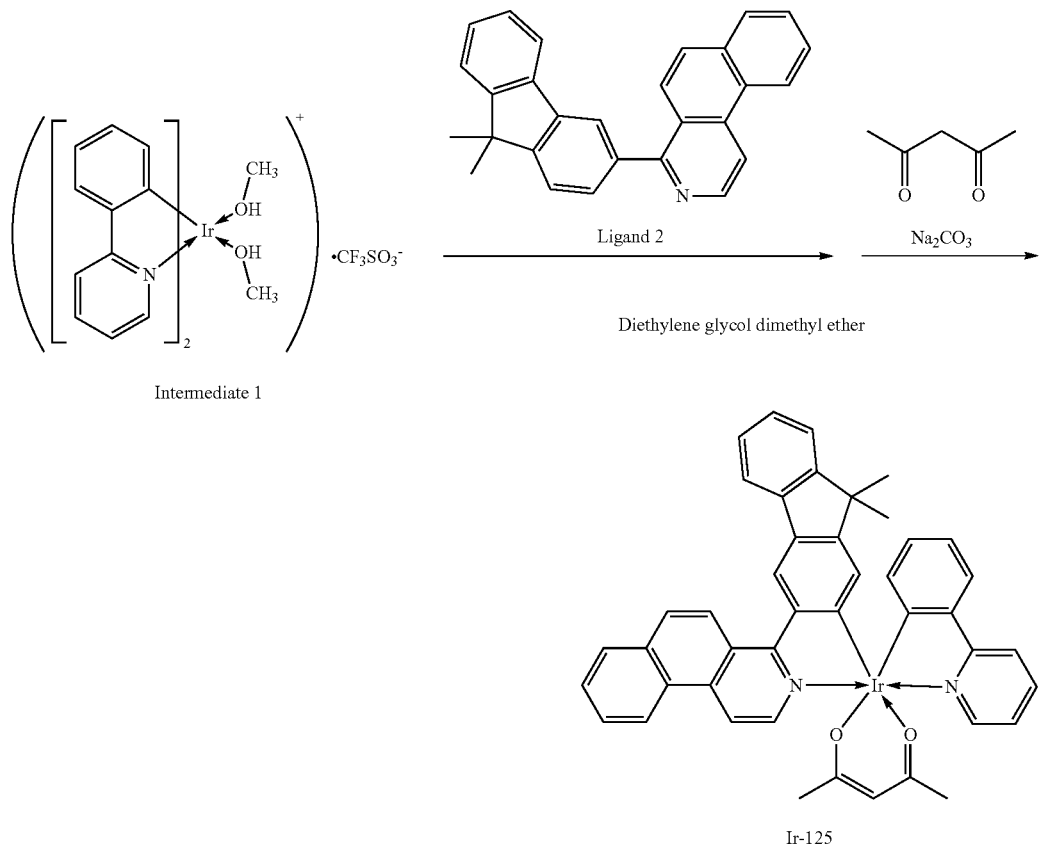

Intermediate 1

Ir-125

Exemplified Compound Ir-125 was obtained by the same method as that of Example 1 except that in Example 1, Ligand 2 was used instead of Ligand 1. It should be noted that Ligand 2 is a ligand synthesized with reference to PTL 3.

MALDI-TOF MS confirmed that the compound had an M$^+$ of 816.2.

In addition, the phosphorescence spectrum of Exemplified Compound Ir-125 in a dilute toluene solution state was measured in the same manner as in Example 1. As a result, its peak wavelength was 613 nm.

Example 4

Synthesis of Exemplified Compound Ir-106

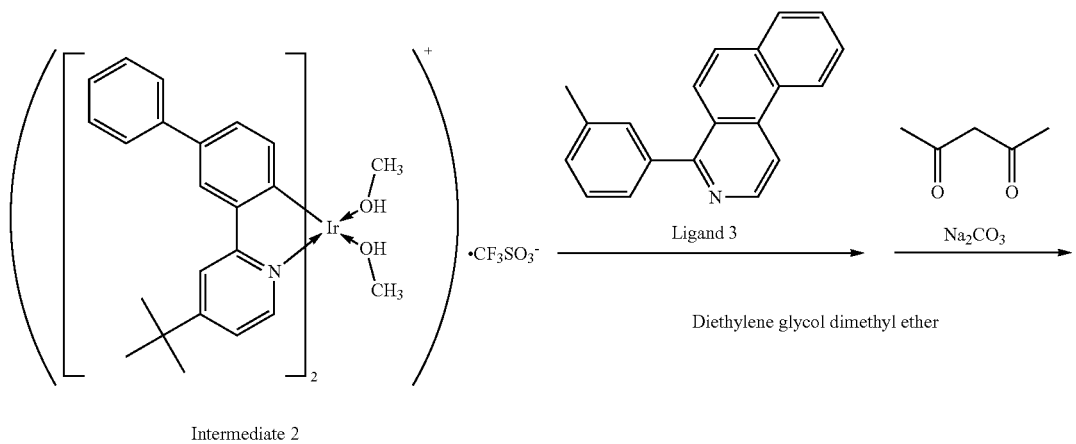

Intermediate 2

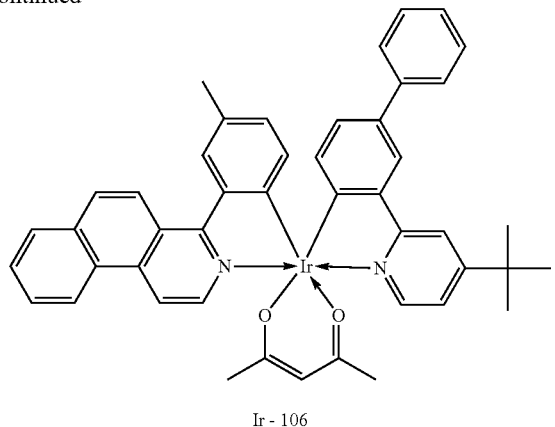

Ir-106

(1) Synthesis of Intermediate 2 and Ligand 3

Intermediate 2 (2-(biphenyl-3-yl)-4-tert-butylpyridine) was synthesized according to a method described in PTL 4. In addition, Ligand 3 was synthesized according to the method described in PTL 3.

(2) Synthesis of Exemplified Compound Ir-106

Exemplified Compound Ir-106 was obtained by the same method as that of Example 1 except that in the section (2) of Example 1, Intermediate 2 was used instead of Intermediate 1 and Ligand 3 was used instead of Ligand 1.

MALDI-TOF MS confirmed that the compound had an M+ of 846.3.

Further, the structure of the compound was identified by $^1$H-NMR measurement.

$^1$H-NMR {(CD$_3$)$_2$S=O, 500 MHz} δ (ppm): 8.96-8.94 (1H, m), 8.85 (1H, d), 8.69 (1H, d), 8.58 (1H, d), 8.35 (1H, d), 8.28 (1H, d), 8.18-8.15 (2H, m), 8.06 (1H, d), 7.99 (1H, s), 7.87-7.85 (2H, m), 7.59 (2H, d), 7.48 (1H, dd), 7.36 (2H, t), 7.23 (1H, t), 6.82 (1H, dd), 6.53 (1H, d), 6.18 (1H, d), 6.03 (1H, d), 5.27 (1H, s), 2.23 (3H, s), 1.75 (3H, s), 1.68 (3H, s), 1.47 (9H, s)

In addition, the phosphorescence spectrum of Exemplified Compound Ir-106 in a dilute toluene solution state was measured in the same manner as in Example 1. As a result, its peak wavelength was 606 nm.

Further, the T$_{sub}$ and T$_d$ of Exemplified Compound Ir-106 were determined in the same manner as in Example 1. As a result, the T$_{sub}$ and the T$_d$ were 290° C. and 375° C., respectively.

Example 5

Synthesis of Exemplified Compound Ir-136

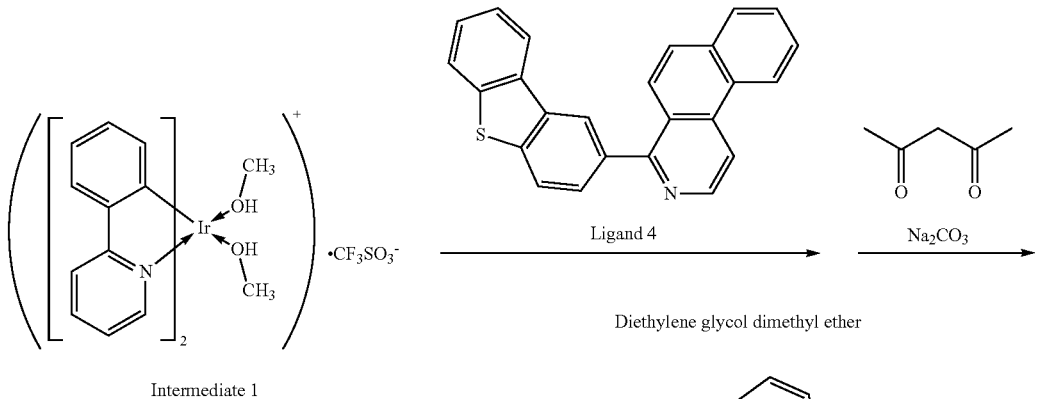

Intermediate 1     Ligand 4     Na$_2$CO$_3$

Diethylene glycol dimethyl ether

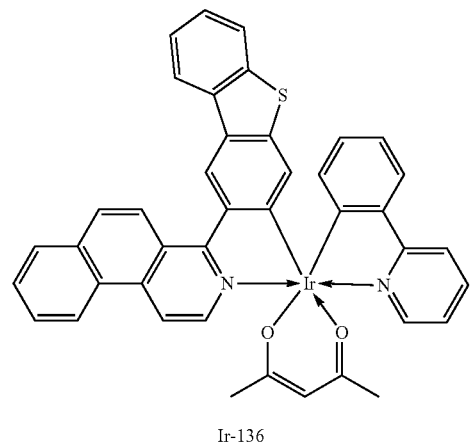

Ir-136

Exemplified Compound Ir-136 was obtained by the same method as that of Example 1 except that in Example 1, Ligand 4 was used instead of Ligand 1. It should be noted that Ligand 4 was synthesized according to the method described in PTL 3.

MALDI-TOF MS confirmed that the compound had an M+ of 806.2.

In addition, the phosphorescence spectrum of Exemplified Compound Ir-136 in a dilute toluene solution state was measured in the same manner as in Example 1. As a result, its peak wavelength was 610 nm.

Example 6

Synthesis of Exemplified Compound Ir-108

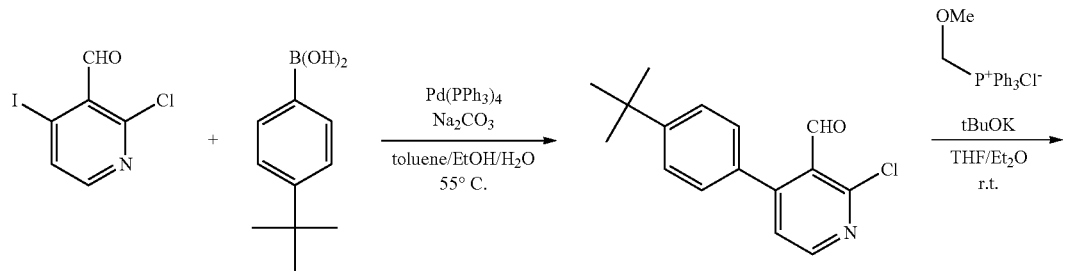

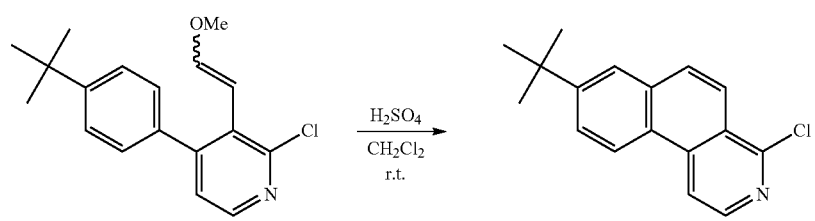

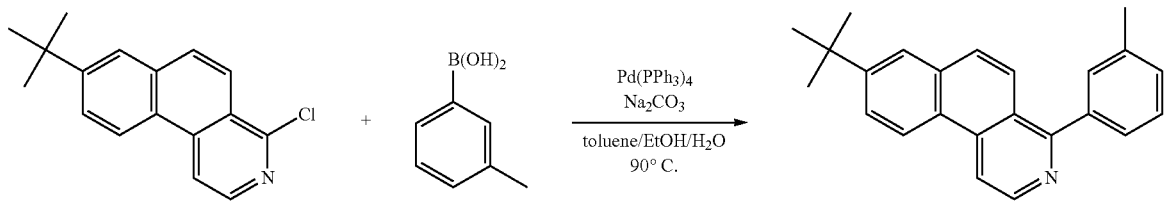

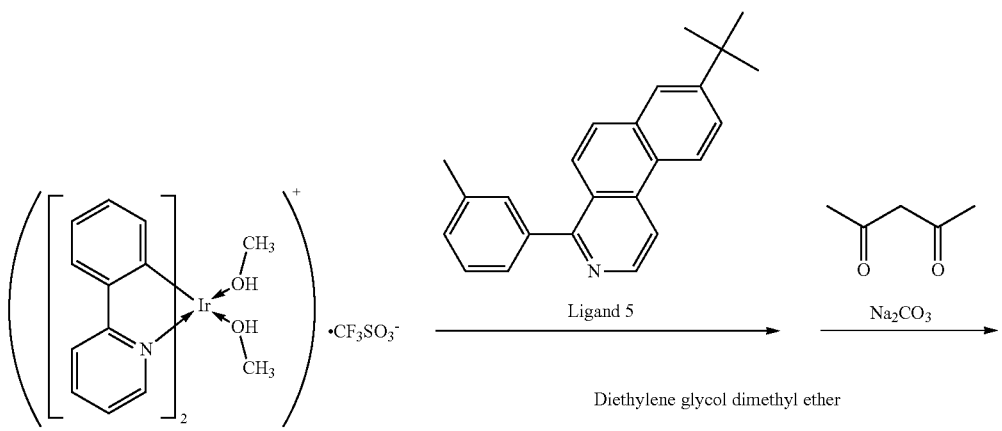

-continued

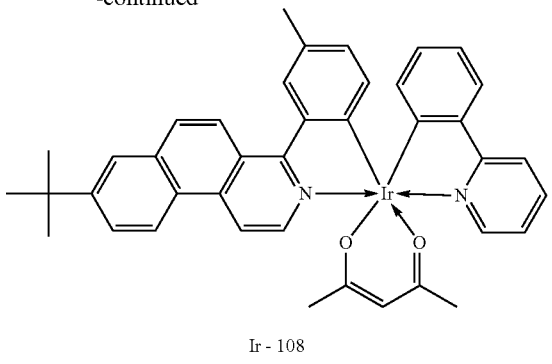

Ir-108

(1) Synthesis of Intermediate 3

Intermediate 3 was synthesized according to the synthesis scheme by using 2-chloro-4-iodonicotinaldehyde (manufactured by Shanghai P&T Fine Chemical) and 4-tert-butylphenylboronic acid (manufactured by Tokyo Chemical Industry Co., Ltd.) as starting raw materials.

(2) Synthesis of Ligand 5

Ligand 5 was synthesized according to the scheme by using Intermediate 3 and 3-methylphenylboronic acid (manufactured by Tokyo Chemical Industry Co., Ltd.).

(3) Synthesis of Exemplified Compound Ir-108

Exemplified Compound Ir-108 was obtained by the same method as that of Example 1 except that in the section (2) of Example 1, Ligand 5 was used instead of Ligand 1.

MALDI-TOF MS confirmed that the compound had an $M^+$ of 770.3.

In addition, the phosphorescence spectrum of Exemplified Compound Ir-108 in a dilute toluene solution state was measured in the same manner as in Example 1. As a result, its peak wavelength was 605 nm.

Example 7

Synthesis of Exemplified Compound Ir-134

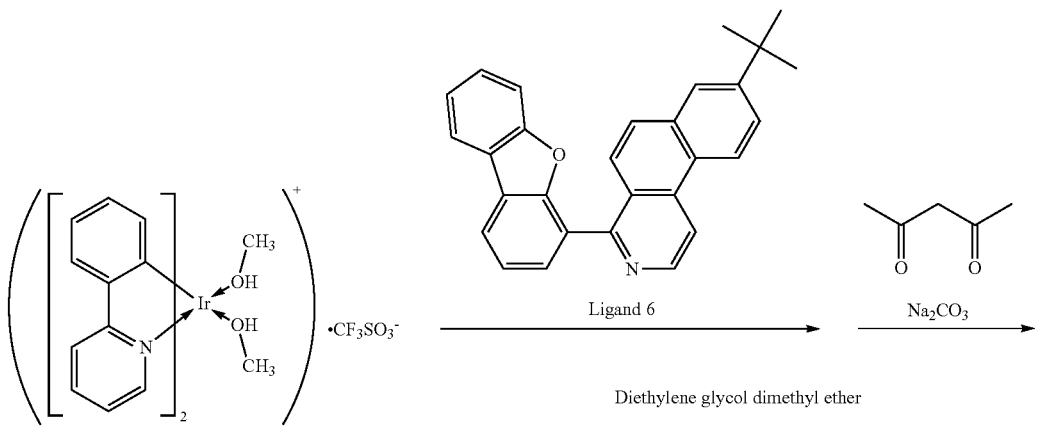

Intermediate 1   Ligand 6   $Na_2CO_3$

Diethylene glycol dimethyl ether

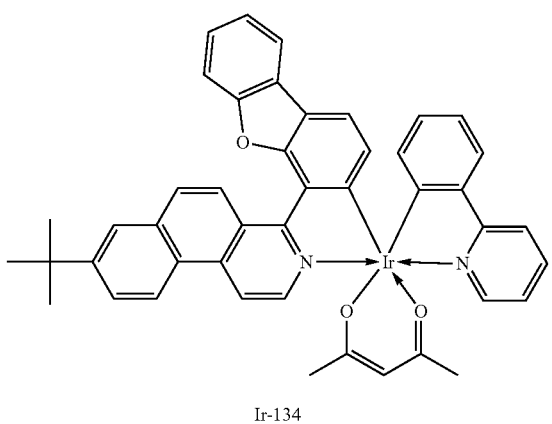

Ir-134

(1) Synthesis of Ligand 6

Ligand 6 was obtained by the same method as that of the section (2) of Example 6 except that in the section (2) of Example 6, 4-(dibenzofuranyl)boronic acid (manufactured by Sigma-Aldrich) was used instead of 3-methylphenylboronic acid.

(2) Synthesis of Exemplified Compound Ir-134

Exemplified Compound Ir-134 was obtained by the same method as that of Example 1 except that in the section (2) of Example 1, Ligand 6 was used instead of Ligand 1.

MALDI-TOF MS confirmed that the compound had an M+ of 846.2.

In addition, the phosphorescence spectrum of Exemplified Compound Ir-134 in a dilute toluene solution state was measured in the same manner as in Example 1. As a result, its peak wavelength was 608 nm.

Example 8

Synthesis of Exemplified Compound Ir-116

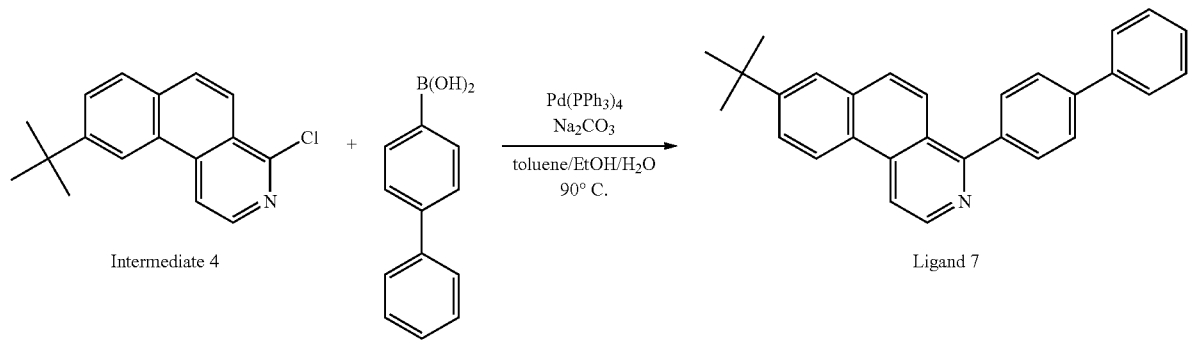

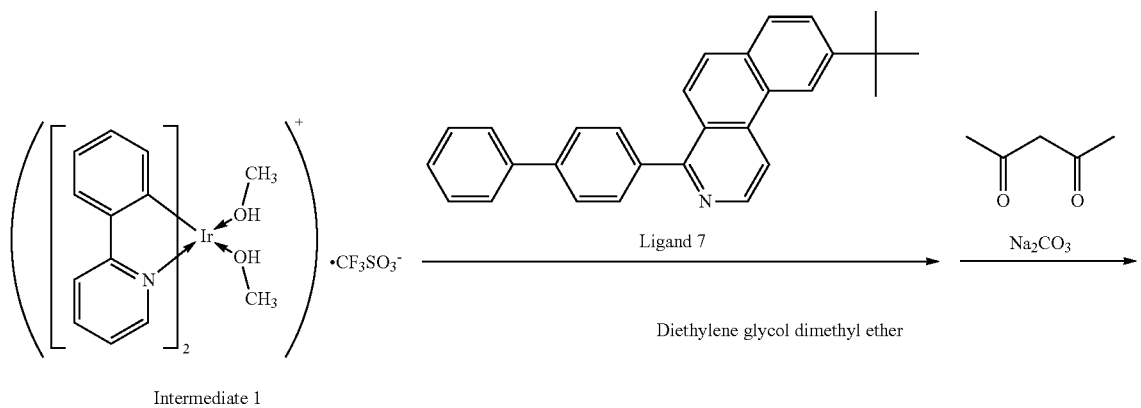

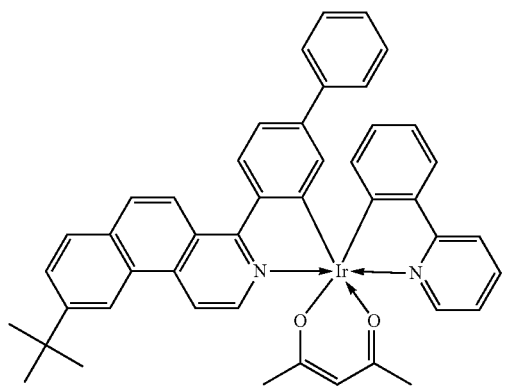

(1) Synthesis of Ligand 7

Intermediate 4 was obtained by the same method as that of the section (1) of Example 6 except that in the section (1) of Example 6, 3-tert-butylphenylboronic acid (manufactured by Wako Pure Chemical Industries, Ltd.) was used instead of 4-tert-butylphenylboronic acid.

Next, Ligand 7 was obtained by the same method as that of the section (2) of Example 6 except that in the section (2) of Example 6, Intermediate 4 was used instead of Intermediate 3 and 4-biphenylboronic acid (manufactured by Tokyo Chemical Industry Co., Ltd.) was used instead of 3-methylphenylboronic acid.

(2) Synthesis of Exemplified Compound Ir-116

Exemplified Compound Ir-116 was obtained by the same method as that of Example 1 except that in Example 1, Ligand 7 was used instead of Ligand 1.

MALDI-TOF MS confirmed that the compound had an $M^+$ of 832.3.

In addition, the phosphorescence spectrum of Exemplified Compound Ir-116 in a dilute toluene solution state was measured in the same manner as in Example 1. As a result, its peak wavelength was 609 nm.

Example 9

Synthesis of Exemplified Compound Ir-201

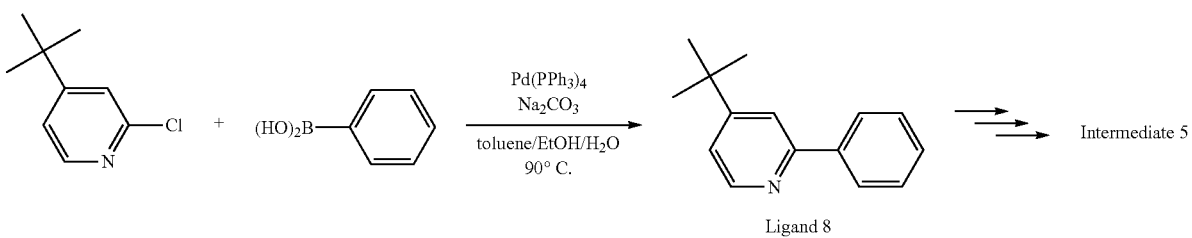

Ligand 8

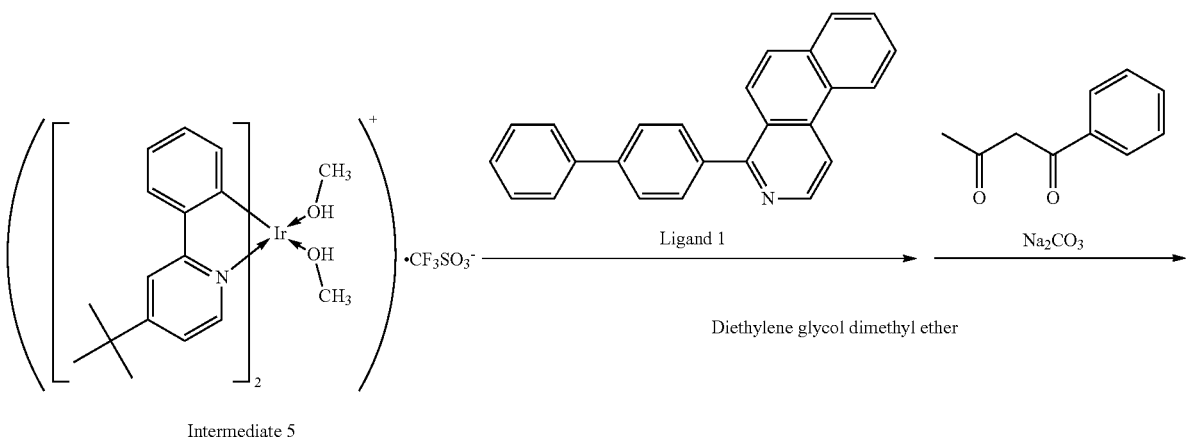

Intermediate 5

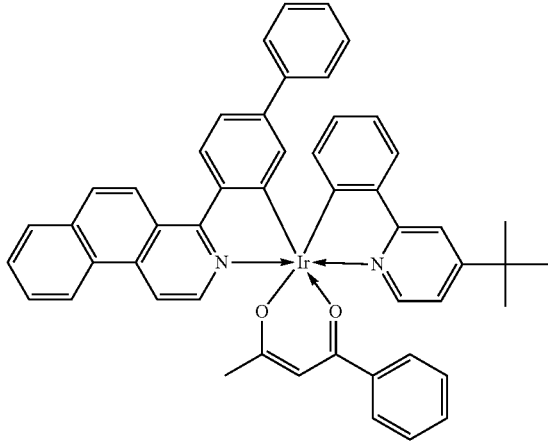

Ir-201

(1) Synthesis of Ligand 8

Ligand 8 was synthesized according to the scheme by using 2-chloro-4-tert-butylpyridine synthesized by the method described in NPL 1 and phenylboronic acid (Tokyo Chemical Industry Co., Ltd.) as starting raw materials.

(2) Synthesis of Exemplified Compound Ir-201

Intermediate 5 was obtained by the same method as that of the section (1) of Example 1 except that in the section (1) of Example 1, 2-phenyl-4-tert-butylpyridine was used instead of 2-phenylpyridine.

Next, Exemplified Compound Ir-201 was obtained by the same method as that of Example 1 except that in the section (2) of Example 1, Intermediate 5 was used instead of Intermediate 1 and 1-phenyl-1,3-butanedione (manufactured by Tokyo Chemical Industry Co., Ltd.) was used instead of acetylacetone.

MALDI-TOF MS confirmed that the compound had an $M^+$ of 894.3.

In addition, the phosphorescence spectrum of Exemplified Compound Ir-201 in a dilute toluene solution state was measured in the same manner as in Example 1. As a result, its peak wavelength was 610 nm.

Example 10

Synthesis of Exemplified Compound Ir-204

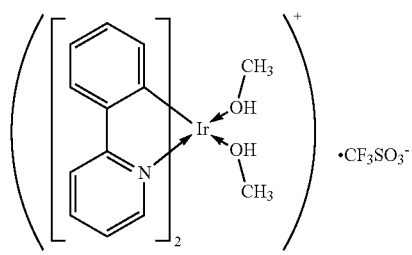

Intermediate 1

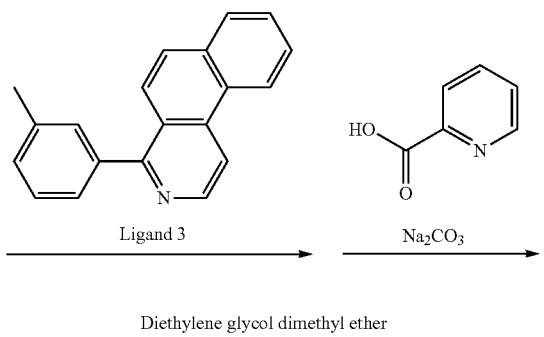

Ligand 3        Na$_2$CO$_3$

Diethylene glycol dimethyl ether

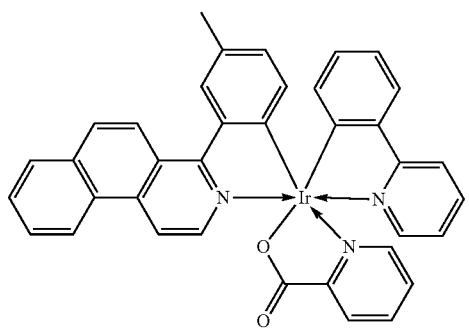

Ir - 204

Exemplified Compound Ir-204 was obtained by the same method as that of Example 1 except that in the section (2) of Example 1, Ligand 3 was used instead of Ligand 1 and pyridine-2-carboxylic acid (manufactured by Tokyo Chemical Industry Co., Ltd.) was used instead of acetylacetone.

MALDI-TOF MS confirmed that the compound had an $M^+$ of 737.2.

In addition, the phosphorescence spectrum of a dilute toluene solution of Exemplified Compound Ir-204 was measured in the same manner as in Example 1. As a result, its peak wavelength was 597 nm.

Synthesis Example 1

Synthesis of Exemplified Compound H-103

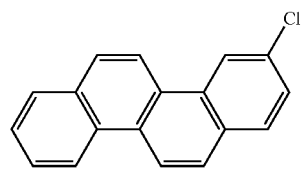

CRY-1

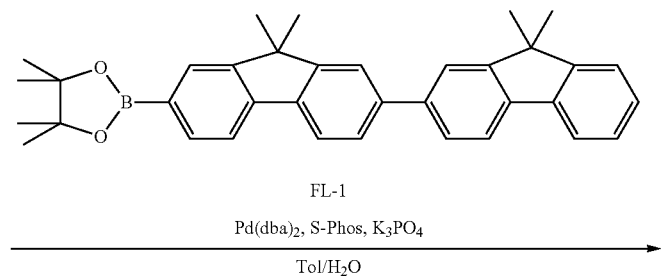

FL-1

Pd(dba)$_2$, S-Phos, K$_3$PO$_4$

Tol/H$_2$O

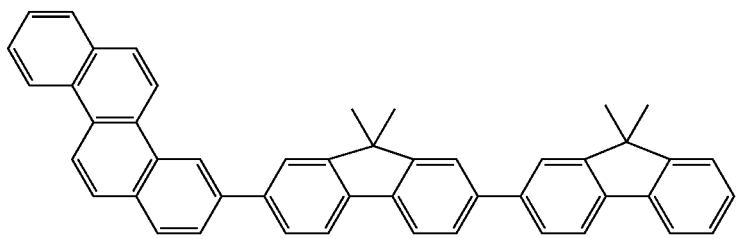

H-103

The following reagents and solvents were loaded in a 100-ml recovery flask.
3-Chlorochrysene (CRY-1): 525 mg (2.00 mmol)
Boronic acid compound (FL-1): 1,017 mg (2.00 mmol)
Palladium(II) acetate: 18 mg (80 μmol)
Dicyclohexyl(2',6'-dimethoxybiphenyl-2-yl)phosphine (S-Phos): 80 mg (194 μmol)
Potassium phosphate: 1.06 g (5.00 mmol)
Toluene: 50 ml
Water: 10 ml Next, the reaction solution was heated to reflux for 8 hours while being stirred. After the completion of the reaction, water was added to the resultant, a liquid-separating operation was performed, and an organic layer was recovered. Next, the recovered organic layer was dried and then the solvent was removed by distillation under reduced pressure, whereby a crude product was obtained. Next, the crude product was purified by silica gel column chromatography (developing solvent: heptane/toluene=4/1) and was then recrystallized with a toluene/ethanol mixed solvent to provide a crystal. Next, the resultant crystal was vacuum-dried at 150° C. and then subjected to sublimation purification to provide 830 mg of Exemplified Compound H-103 (yield: 68%).

The resultant compound was evaluated for its purity by employing HPLC. As a result, it was confirmed that the purity was 99% or more.

MALDI-TOF MS confirmed that the compound had an $M^+$ of 612.3.

Synthesis Example 2

Synthesis of Exemplified Compound D-102

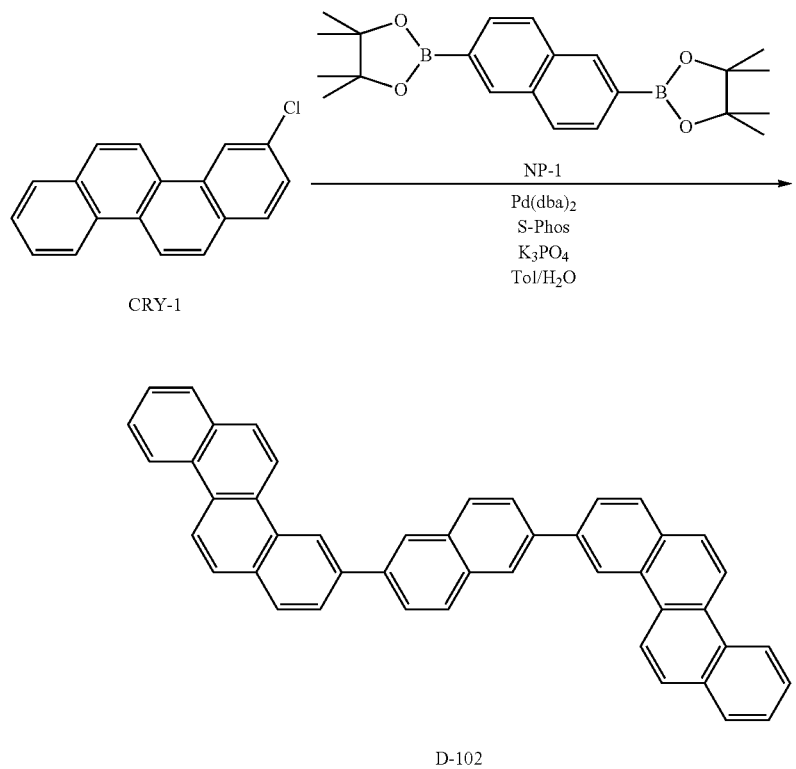

D-102

The following reagents and solvents were loaded in a 100-ml recovery flask.

3-Chlorochrysene (CRY-1): 578 mg (2.2 mmol)
Boronic acid compound (NP-1): 380 mg (1.0 mmol)
Palladium(II) acetate: 18 mg (80 μmol)
Dicyclohexyl(2',6'-dimethoxybiphenyl-2-yl)phosphine: 80 mg (194 μmol)
Potassium phosphate: 1.06 g (5.00 mmol)
Toluene: 50 ml
Water: 10 ml Next, the reaction solution was heated to reflux for 8 hours while being stirred. After the completion of the reaction, water was added to the resultant, a liquid-separating operation was performed, and an organic layer was recovered. Next, the recovered organic layer was dried and then the solvent was removed by distillation under reduced pressure, whereby a crude product was obtained. Next, the crude product was purified by silica gel column chromatography (developing solvent: heptane/toluene=4/1) and was then recrystallized with a toluene/ethanol mixed solvent to provide a crystal. Next, the resultant crystal was vacuum-dried at 150° C. and then subjected to sublimation purification to provide 337 mg of Exemplified Compound D-102 (yield: 58%).

The resultant compound was evaluated for its purity by employing HPLC. As a result, it was confirmed that the purity was 99% or more.

MALDI-TOF MS confirmed that the compound had an $M^+$ of 580.2.

Synthesis Example 3

Synthesis of Exemplified Compound F-101

Exemplified Compound F-101 was obtained by the same method as that of Synthesis Example 1 except that in Synthesis Example 1, 3-chlorophenanthrene was used instead of 3-chlorochrysene and FL-2 shown below was used instead of FL-1.

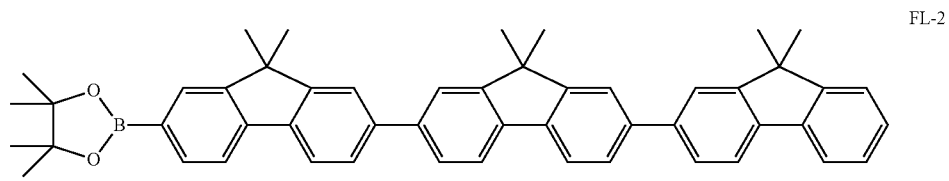 [SMILES: CC1(C)c2ccccc2-c2ccc(-c3ccc4c(c3)C(C)(C)c3cc(-c5ccc6c(c5)C(C)(C)c5cc(B7OC(C)(C)C(C)(C)O7)ccc5-6)ccc3-4)cc21]

FL-2

The resultant compound was evaluated for its purity by employing HPLC. As a result, it was confirmed that the purity was 99% or more.

MALDI-TOF MS confirmed that the compound had an $M^+$ of 755.0.

Synthesis Example 4

Synthesis of Exemplified Compound H-102

Exemplified Compound H-102 was obtained by the same method as that of Synthesis Example 1 except that in Synthesis Example 1, 3-chlorophenanthrene was used instead of 3-chlorochrysene.

The resultant compound was evaluated for its purity by employing HPLC. As a result, it was confirmed that the purity was 99% or more.

MALDI-TOF MS confirmed that the compound had an M+ of 562.3.

Synthesis Example 5

Synthesis of Exemplified Compound L-104

Exemplified Compound L-104 was obtained by the same method as that of Synthesis Example 1 except that in Synthesis Example 1, a compound NPTRP-1 shown below was used instead of FL-1.

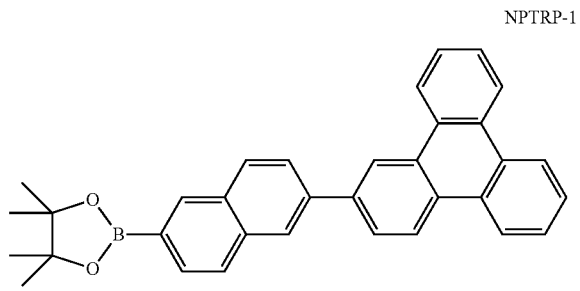 [SMILES: CC1(C)OB(c2ccc3cc(-c4ccc5c6ccccc6c6ccccc6c5c4)ccc3c2)OC1(C)C]

NPTRP-1

The resultant compound was evaluated for its purity by employing HPLC. As a result, it was confirmed that the purity was 99% or more.

MALDI-TOF MS confirmed that the compound had an M+ of 580.2.

Synthesis Example 6

Synthesis of Exemplified Compound L-105

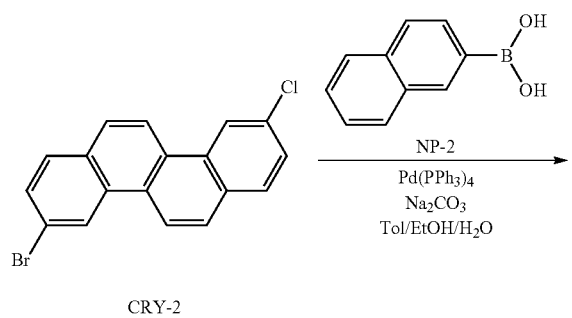

CRY-2

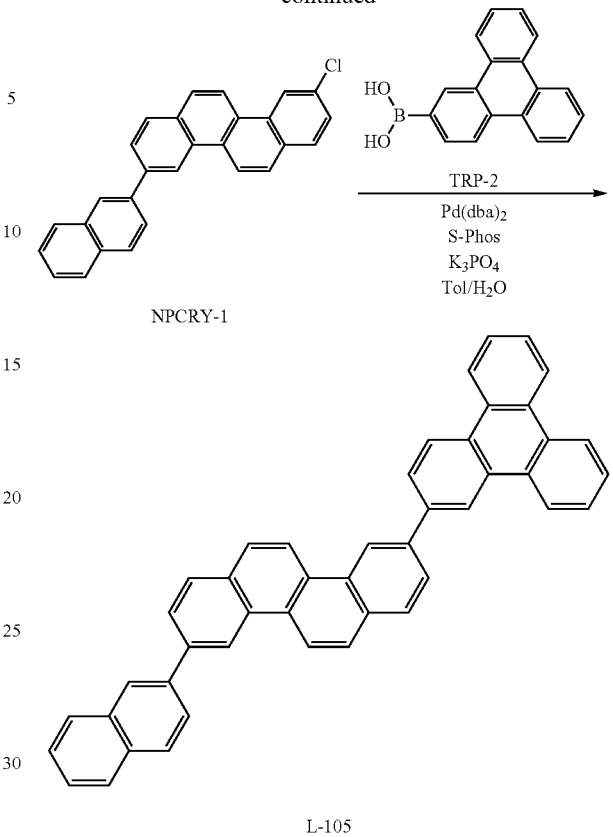

L-105

(1) Synthesis of Compound NPCRY-1

The following reagents and solvents were loaded in a 100-ml recovery flask.
CRY-2: 1.23 g (3.0 mmol)
NP-2: 0.53 g (3.1 mmol)
Tetrakis(triphenylphosphine)palladium(0): 0.1 g (0.08 mmol)
Toluene: 10 ml
Ethanol: 5 ml
10 wt % sodium carbonate aqueous solution: 5 ml Next, under nitrogen, the reaction solution was heated to reflux for 5 hours while being stirred. After the completion of the reaction, the reaction solution was washed with water and then dried with sodium sulfate, followed by concentration under reduced pressure. Thus, a crude product was obtained. Next, the crude product was purified by silica gel column chromatography (developing solvent: toluene/heptane=2/1) to provide 0.99 g of NPCRY-1 (yield: 85%).

(2) Synthesis of Exemplified Compound L-105

The following reagents and solvents were loaded in a 100-ml recovery flask.
Intermediate NPCRY-1: 389 mg (1.0 mmol)
Boronic acid compound TRP-2: 272 mg (1.0 mmol)
Palladium(II) acetate: 18 mg (80 μmol)
Dicyclohexyl(2',6'-dimethoxybiphenyl-2-yl)phosphine: 80 mg (194 μmol)
Potassium phosphate: 0.53 g (2.5 mmol)
Toluene: 10 ml
Water: 2 ml Next, the reaction solution was heated to reflux for 8 hours while being stirred. After the completion of the reaction, water was added to the resultant, a liquid-separating operation was performed, and an organic layer was recovered. Next, the recovered organic layer was dried and then the solvent was removed by distillation under reduced pressure, whereby a crude product was obtained. Next, the crude product was purified by silica gel column chromatography (developing solvent: heptane/toluene=4/1) and was then recrystallized with toluene/ethanol to provide a crystal. Next, the resultant crystal was vacuum-dried at 150° C. and then subjected to sublimation purification to provide 458 mg of Exemplified Compound L-105 (yield: 79%).

The resultant compound was evaluated for its purity by employing HPLC. As a result, it was confirmed that the purity was 99% or more.

MALDI-TOF MS confirmed that the compound had an M$^+$ of 580.2.

Synthesis Example 7

Synthesis of Exemplified Compound J-105

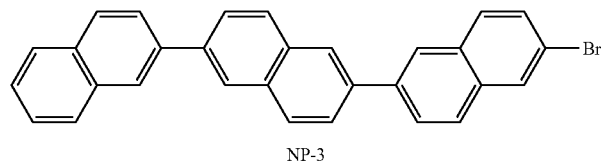

NP-3

Synthesis Example 9

Synthesis of Exemplified Compound X-108

Exemplified Compound X-108 was synthesized according to a method described in PTL 6.

Synthesis Example 10

Synthesis of Exemplified Compound X-111

Exemplified Compound X-111 was obtained by the same method as that of Synthesis Example 6 except that in Synthesis Example 6, FL-3 shown below was used instead of CRY-2 and NPTRP-1 was used instead of NP-2.

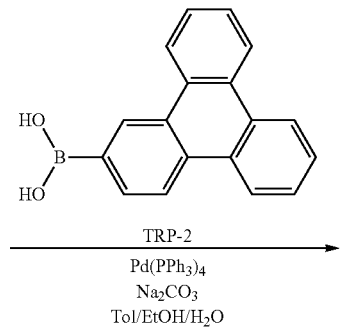

TRP-2

Pd(PPh$_3$)$_4$
Na$_2$CO$_3$
Tol/EtOH/H$_2$O

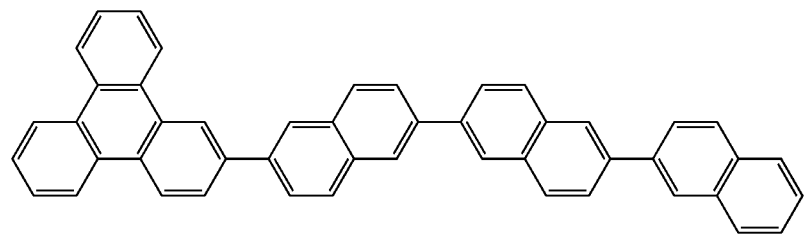

J-105

Exemplified Compound J-105 was obtained by the same method as that of Synthesis Example 6 except that in Synthesis Example 6, NP-3 was used instead of CRY-2 and TRP-2 was used instead of NP-2.

The resultant compound was evaluated for its purity by employing HPLC. As a result, it was confirmed that the purity was 99% or more.

MALDI-TOF MS confirmed that the compound had an M$^+$ of 606.2.

Synthesis Example 8

Synthesis of Exemplified Compound X-105
Exemplified Compound X-105 was synthesized according to a method described in PTL 5.

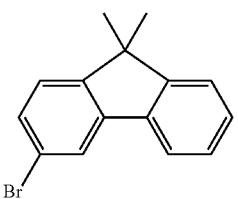

FL-3

The resultant compound was evaluated for its purity by employing HPLC. As a result, it was confirmed that the purity was 99% or more.

MALDI-TOF MS confirmed that the compound had an M+ of 546.2.

Example 11

Production of Organic Light-Emitting Element

In this example, an organic light-emitting element having a construction in which an anode, a hole injection layer, a hole transport layer, an emission layer, a hole/exciton blocking layer, an electron transport layer, and a cathode were formed on a substrate in the stated order was produced by the following method.

ITO was formed into a film on a glass substrate by a sputtering method to form an anode. At this time, the thickness of the anode was set to 100 nm. The substrate on which the anode had been thus formed was used as a transparent conductive supporting substrate (ITO substrate) in the following steps.

Next, organic compound layers and electrode layers shown in Table 3 below were continuously formed on the ITO substrate by a vacuum deposition method involving utilizing resistance heating in a vacuum chamber at $1\times10^{-5}$ Pa. At this time, the formation was performed so that an opposing electrode area became 3 mm$^2$.

TABLE 3

|  | Material | Thickness [nm] |
|---|---|---|
| Hole injection layer | HT-1 | 50 |
| Hole transport layer | HT-8 | 10 |
| Emission layer | Host: H-103<br>Guest: Ir-113<br>(Host:Guest = 95:5<br>(weight ratio)) | 30 |
| Hole/exciton blocking layer | ET-3 | 10 |
| Electron transport layer | ET-2 | 50 |
| First metal electrode layer | LiF | 0.5 |
| Second metal electrode layer | Al | 100 |

Finally, the produced element was sealed with a glass cap with a moisture absorbent in an inert atmosphere to provide an organic light-emitting element.

The current-voltage characteristics of the resultant organic light-emitting element were measured with an ammeter 2700 manufactured by Keithley Instruments, and its emission luminance was measured with a BM7-fast manufactured by TOPCON CORPORATION.

Table 3 shows a light-emitting efficiency when a current having a density of 10 mA/cm$^2$ was applied by using the ITO electrode as a positive electrode and the Al electrode as a negative electrode, and a luminance half-life when a current having a density of 100 mA/cm$^2$ was applied.

In addition, when a current having a density of 10 mA/cm$^2$ was applied, an emission peak wavelength was 616 nm and CIE chromaticity coordinates (x, y) were (0.66, 0.34). In other words, a good red color was shown.

Examples 12 to 23

Organic light-emitting elements were each obtained by the same method as that of Example 11 except that in Example 11, the host and the guest were each changed to a material shown in Table 4.

The resultant organic light-emitting elements were evaluated in the same manner as in Example 11. As a result, good red light emission was observed in each of the elements. Here, Table 4 shows a light-emitting efficiency when a current having a density of 10 mA/cm$^2$ was applied and a luminance half-life when a current having a density of 100 mA/cm$^2$ was applied.

Examples 24 to 27

Organic light-emitting elements were each obtained by the same method as that of Example 11 except that in Example 11, the host, guest, and third component shown in Table 4 below were used upon formation of the emission layer. It should be noted that a weight ratio "host:guest:third component" among the host, guest, and third component in the emission layer is 75:5:20.

The resultant organic light-emitting elements were evaluated in the same manner as in Example 11. As a result, good red light emission was observed in each of the elements. Here, Table 4 shows a light-emitting efficiency when a current having a density of 10 mA/cm$^2$ was applied and a luminance half-life when a current having a density of 100 mA/cm$^2$ was applied.

TABLE 4

|  | Host | Guest | Third component | Light-emitting efficiency (cd/A) | Luminance half-life (h) |
|---|---|---|---|---|---|
| Example 11 | H-103 | Ir-113 | — | 23 | 450 |
| Example 12 | F-101 | Ir-114 | — | 24 | 120 |
| Example 13 | J-105 | Ir-125 | — | 26 | 440 |
| Example 14 | L-105 | Ir-106 | — | 28 | 280 |
| Example 15 | D-102 | Ir-136 | — | 20 | 610 |
| Example 16 | H-102 | Ir-108 | — | 29 | 270 |
| Example 17 | L-104 | Ir-134 | — | 21 | 140 |
| Example 18 | D-102 | Ir-116 | — | 23 | 550 |
| Example 19 | J-105 | Ir-125 | — | 22 | 320 |
| Example 20 | L-105 | Ir-204 | — | 24 | 130 |
| Example 21 | X-105 | Ir-106 | — | 26 | 350 |
| Example 22 | X-108 | Ir-114 | — | 25 | 200 |
| Example 23 | X-111 | Ir-136 | — | 20 | 420 |
| Example 24 | H-102 | Ir-108 | M-103 | 31 | 400 |
| Example 25 | L-105 | Ir-113 | M-105 | 28 | 690 |
| Example 26 | L-104 | Ir-116 | O-101 | 26 | 560 |
| Example 27 | L-104 | Ir-201 | N-103 | 25 | 630 |

Example 28

In this example, a top emission-type organic light-emitting element was produced by a method described below.

First, Al was formed into a film on a glass substrate (transparent substrate) by a sputtering method to produce an Al layer. Next, an indium zinc oxide was formed into a film on the Al layer by the sputtering method to form a transparent electrode layer. At this time, the thickness of the transparent electrode layer was set to 80 nm. It should be noted that a laminate formed of the Al layer and the transparent electrode layer functions as an anode. Next, an acrylic resin was formed into a film on the anode and then the acrylic resin was subjected to patterning to form a pixel separation film. Thus, the substrate with the anode was obtained. It should be noted that the area of the anode became 3 mm$^2$ as a result of the formation of the pixel separation film. Next, organic compound layers shown in Table 5 below were formed on the substrate with the anode by a vacuum deposition method involving utilizing resistance heating in a vacuum chamber at $1\times10^{-5}$ Pa.

TABLE 5

| | Material | Thickness [nm] |
|---|---|---|
| Hole injection layer | HT-1 | 50 |
| Hole transport layer | HT-8 | 10 |
| Emission layer | Host: L-105<br>Guest: Ir-106<br>Third component: M-103<br>(Host:Guest:Third component = 75:5:25 (weight ratio)) | 30 |
| Hole/exciton blocking layer | ET-3 | 10 |
| Electron transport layer | ET-2, cesium carbonate (ET-2:Cs$_2$CO$_3$ = 97:3) | 50 |

Next, an indium zinc oxide was formed into a film on the organic compound layers by the sputtering method to form a cathode. At this time, the thickness of the cathode was set to 30 nm.

Finally, the produced element was sealed with a glass cap with a moisture absorbent in an inert atmosphere to provide an organic light-emitting element.

The element performance of the resultant organic light-emitting element was measured and evaluated in the same manner as in Example 11. As a result, its light-emitting efficiency when a current having a density of 10 mA/cm$^2$ was applied was 38 cd/A.

It was understood that an organic light-emitting element showing good light-emitting efficiency and a good element lifetime was obtained by incorporating, into its emission layer, the iridium complex according to the present invention as a guest and an aromatic hydrocarbon compound having a predetermined structure as a host as described above.

Advantageous Effects of Invention

As described above with reference to the embodiments and Examples, according to the present invention, it is possible to provide the organic light-emitting element having high light-emitting efficiency and a long element lifetime.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-008463, filed on Jan. 21, 2013, which is hereby incorporated by reference herein in its entirety.

The invention claimed is:

1. An iridium complex comprising a compound represented by the following general formula [1]:

Ir(L$_1$)(L$_2$)(L$_3$)      [1]

in the general formula [1]:
L$_1$, L$_2$, and L$_3$ represent bidentate ligands different from one another; and
the partial structure IrL$_1$ comprises a partial structure represented by the following general formula [2]:

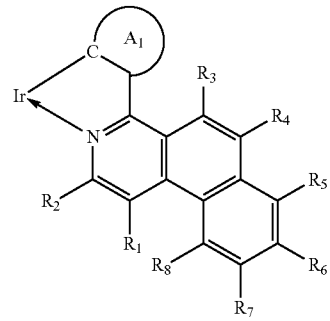

[2]

in the general formula [2]:
the ring A$_1$ represents an aromatic ring or an aromatic heterocycle, and the ring A$_1$ can further have a substituent selected from the group consisting of an alkyl group having 1 or more and 4 or less carbon atoms, an aralkyl group, an aryl group, a heterocyclic group, a substituted amino group, an alkoxy group, an aryloxy group, a halogen atom, and a cyano group; and
R$_1$ to R$_8$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group, and can be identical to or different from one another, and when any one of substituents represented by R$_1$ to R$_8$ is an alkyl group having 1 or more and 4 or less carbon atoms, an aralkyl group, an aryl group, a heterocyclic group, a substituted amino group, an alkoxy group, or an aryloxy group, the substituent can further have a substituent selected from the group consisting of an alkyl group having 1 or more and 4 or less carbon atoms, an aralkyl group, an aryl group, a heterocyclic group, a substituted amino group, an alkoxy group, an aryloxy group, a halogen atom, and a cyano group;
in the general formula [1]:
the partial structure IrL$_2$ comprises a partial structure represented by the following general formula [3]:

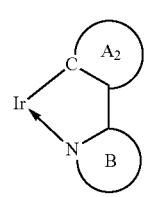

[3]

in the general formula [3]:
the ring A$_2$ represents an aromatic ring or an aromatic heterocycle, and the ring A$_2$ can further have a substituent selected from the group consisting of an alkyl group having 1 or more and 4 or less carbon atoms, an aralkyl group, an aryl group, a heterocyclic group, a substituted amino group, an alkoxy group, an aryloxy group, a halogen atom, and a cyano group; and
the ring B represents a nitrogen-containing aromatic heterocycle, and the ring B can further have a substituent selected from the group consisting of an alkyl group having 1 or more and 4 or less carbon atoms, an aralkyl group, an aryl group, a heterocyclic group, a substituted amino group, an alkoxy group, an aryloxy group, a halogen atom, and a cyano group; and $L_3$ represents a monovalent bidentate ligand having a first atom that forms a bond with iridium and is selected from N, O, S, and P, and a second atom that forms a bond with iridium and is selected from N, O, S, and P, and the first atom and the second atom can be identical to or different from each other.

2. The iridium complex according to claim 1, wherein the ring $A_1$ is a benzene ring, a naphthalene ring, a fluorene ring, a phenanthrene ring, a carbazole ring, a dibenzofuran ring, or a dibenzothiophene ring; and the ring $A_1$ can further have a substituent selected from the group consisting of an alkyl group having 1 or more and 4 or less carbon atoms, an aralkyl group, an aryl group, a heterocyclic group, a substituted amino group, an alkoxy group, an aryloxy group, a halogen atom, or a cyano group.

3. The iridium complex according to claim 1, wherein the partial structure represented by the general formula [2] comprises a partial structure represented by the following general formula [4]:

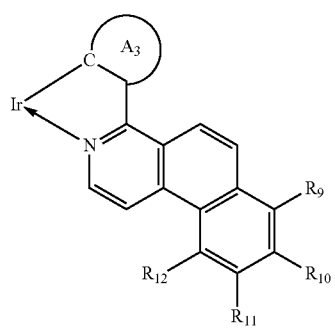

[4]

in the general formula [4]:

the ring $A_3$ is a benzene ring, a naphthalene ring, a fluorene ring, a phenanthrene ring, a carbazole ring, a dibenzofuran ring, or a dibenzothiophene ring and the ring $A_3$ can further have a substituent selected from the group consisting of an alkyl group having 1 or more and 4 or less carbon atoms, an aralkyl group, an aryl group, a heterocyclic group, a substituted amino group, an alkoxy group, an aryloxy group, a halogen atom, and a cyano group; and $R_9$ to $R_{12}$ each represent a hydrogen atom, an alkyl group having 1 or more and 4 or less carbon atoms, or a phenyl group, and when any one of substituents represented by $R_9$ to $R_{12}$ is an alkyl group having 1 or more and 4 or less carbon atoms or a phenyl group, the substituent can further have a substituent selected from the group consisiting of an alkyl group having 1 or more and 4 or less carbon atoms, an aralkyl group, an aryl group, a heterocyclic group, a substituted amino group, an alkoxy group, an aryloxy group, a halogen atom, and a cyano group, and $R_9$ to $R_{12}$ can be identical to or different from one another.

4. The iridium complex according to claim 1, wherein the ring $A_2$ represents a benzene ring, a naphthalene ring, a fluorene ring, a phenanthrene ring, a carbazole ring, a dibenzofuran ring, or a dibenzothiophene ring;

the ring $A_2$ can further have a substituent selected from the group consisting of an alkyl group having 1 or more and 4 or less carbon atoms, an aralkyl group, an aryl group, a heterocyclic group, a substituted amino group, an alkoxy group, an aryloxy group, a halogen atom, or a cyano group;

the ring B represents a pyridine ring, a quinoline ring, an isoquinoline ring, a benzo[f]quinoline ring, a benzo[h]quinoline ring, a benzo[f]isoquinoline ring, a benzo[h]isoquinoline ring, an oxazole ring, a benzo[d]oxazole ring, a benzo[d]thiazole ring, or an imidazole ring; and the ring B can futher have a substutent selected from the group consisting of an alkyl group having 1 or more and 4 or less carbon atoms, an aralkyl group, an aryl group, a heterocyclic group, a substituted amino group, an alkoxy group, an aryloxy group, a halogen atom, or a cyano group.

5. The iridium complex according to claim 1, wherein the partial structure represented by $IrL_1$ comprises a partial structure represented by the following general formula [8]:

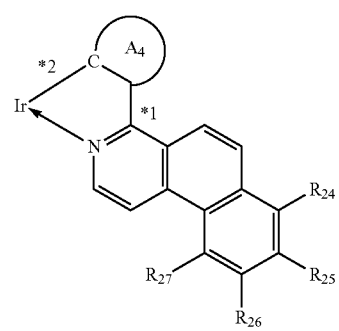

[8]

in the formula [8]:

a ring $A_4$ represents any one of partial structures represented by the following general formula [9] to [13];

*1 represents a bond between the ring $A_4$ and an isoquinoline skeleton and *2 represents a bond between the ring $A_4$ and an Ir metal; and $R_{24}$ to $R_{27}$ each represent a hydrogen atom, an alkyl group having 1 or more and 4 or less carbon atoms, or a phenyl group, and may be identical to or different from one another, and when any one of substituents represented by $R_{24}$ to $R_{27}$ is an alkyl group having 1 or more and 4 or less carbon atoms or a phenyl group, the substituent can futher have a substutent selected from the group consisting of an alkyl group having 1 or more and 4 or less carbon atoms, an aralkyl group, an aryl group, a heterocyclic group, a substituted amino group, an alkoxy group, an aryloxy group, a halogen atom, and a cyano group:

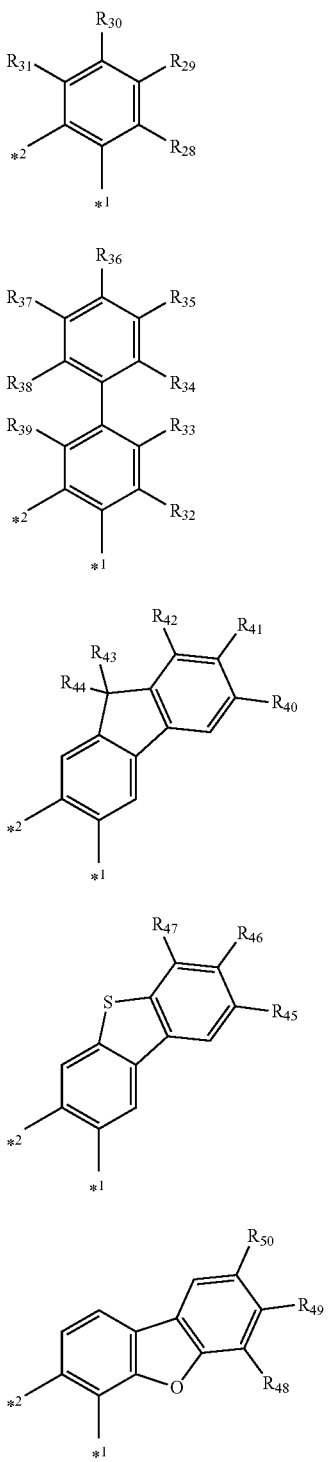

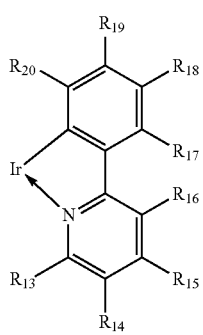

in the general formulae [9] to [13], $R_{28}$ to $R_{50}$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group, and when any one of substituents represented by $R_{28}$ to $R_{50}$ is an alkyl group having 1 or more and 4 or less carbon atoms, an aralkyl group, an aryl group, a heterocyclic group, a substituted amino group, an alkoxy group, or an aryloxy group, the substituent can further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

6. The iridium complex according to claim 1, wherein the partial structure represented by the general formula [3] comprises a partial structure represented by the following general formula [5]:

in the general formula [5]:
$R_{13}$ to $R_{20}$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group, and can be identical to or different from one another, and when any one of substituents represented by $R_{13}$ to $R_{20}$ is an alkyl group having 1 or more and 4 or less carbon atoms, an aralkyl group, an aryl group, a heterocyclic group, a substituted amino group, an alkoxy group, the substituent can futher have a substutent selected from the group consisting of an alkyl group having 1 or more and 4 or less carbon atoms, an aralkyl group, an aryl group, a heterocyclic group, a substituted amino group, an alkoxy group, an aryloxy group, a halogen atom, or a cyano group.

7. The iridium complex according to claim 6, wherein the $R_{13}$ to $R_{20}$ each represent a hydrogen atom, an alkyl group having 1 or more and 4 or less carbon atoms, or a phenyl group; and when any one of the substituents represented by the $R_{13}$ to $R_{20}$ is an alkyl group having 1 or more and 4 or less carbon atoms, or a phenyl group, the substituent can futher have a substutent selected from the group consisting of an alkyl group having 1 or more and 4 or less carbon atoms, an aralkyl group, an aryl group, a heterocyclic group, a substituted amino group, an alkoxy group, an aryloxy group, a halogen atom, or a cyano group.

8. The iridium complex according to claim 1, wherein in the general formula [1], a partial structure $IrL_3$ comprises a partial structure represented by the following general formula [6]:

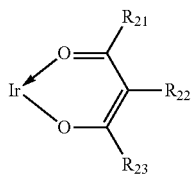

[6]

in the general formula [6]:
$R_{21}$ to $R_{23}$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group, and can be identical to or different from one another, and when any one of substituents represented by $R_{21}$ to $R_{23}$ is an alkyl group having 1 or more and 4 or less carbon atoms, an aralkyl group, an aryl group, a heterocyclic group, a substituted amino group, an alkoxy group, or an aryloxy group, the substituent can futher have a substituent selected from the group consisting of an alkyl group having 1 or more and 4 or less carbon atoms, an aralkyl group, an aryl group, a heterocyclic group, a substituted amino group, an alkoxy group, an aryloxy group, a halogen atom, or a cyano group.

9. The iridium complex according to claim 8, wherein the $R_{21}$ to $R_{23}$ each represent a hydrogen atom or an alkyl group having 1 or more and 4 or less carbon atoms; and
when any one of the substituents represented by the $R_{21}$ to $R_{23}$ is an alkyl group having 1 or more and 4 or less carbon atoms, the substituent can futher have a substutent selected from the group consisting of an alkyl group having 1 or more and 4 or less carbon atoms, an aralkyl group, an aryl group, a heterocyclic group, a substituted amino group, an alkoxy group, an aryloxy group, a halogen atom, or a cyano group.

10. An organic light-emitting element comprising:
an anode;
a cathode; and
an organic compound layer placed between the anode and the cathode,
wherein the organic compound layer includes an emission layer;
the emission layer comprises at least a host and a guest;
the host comprises an aromatic hydrocarbon compound; and
the guest comprises the iridium complex according to claim 1.

11. The organic light-emitting element according to claim 10, wherein the aromatic hydrocarbon compound has multiple aromatic hydrocarbon compound skeletons each independently selected from the group consisting of benzene, naphthalene, phenanthrene, fluorene, triphenylene, chrysene, fluoranthene, picene, indeno[2,1-a]phenanthrene having, only on sp³ carbon, two alkyl groups each having 1 or more and 4 or less carbon atoms, and indeno[1,2-b] phenanthrene having, only on sp³ carbon, two alkyl groups each having 1 or more and 4 or less carbon atoms; and
the benzene, the naphthalene, the phenanthrene, the triphenylene, the chrysene, the fluoranthene, and the picene are each free of a substituent except a bond between the skeletons of the aromatic hydrocarbon compound.

12. The organic light-emitting element according to claim 11, wherein the aromatic hydrocarbon compound comprises a compound represented by the following general formula [7]:

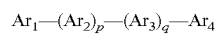

[7]

in the general formula [7]:
p and q each represent 0 or 1, provided that any one of p and q represents 1;
$Ar_1$ represents any one of substituents represented in the following substituent group α1;
$Ar_2$ and $Ar_3$ each represent any one of substituents represented in the following substituent group β1; and
$Ar_4$ represents any one of substituents represented in the following substituent group γ1:

[Substituent group α1]

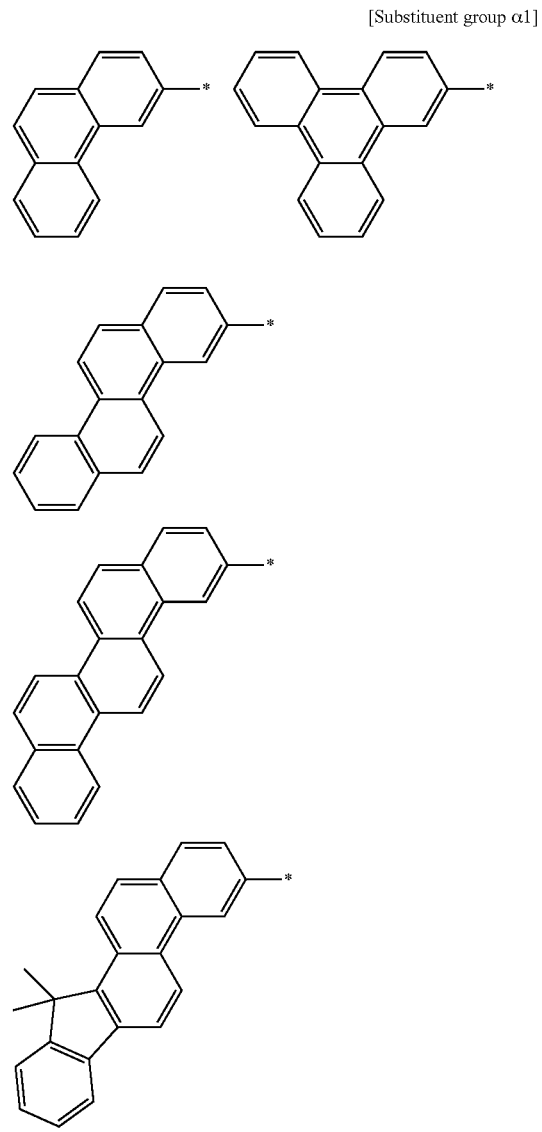

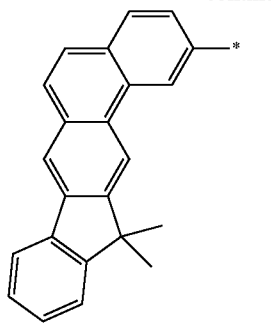
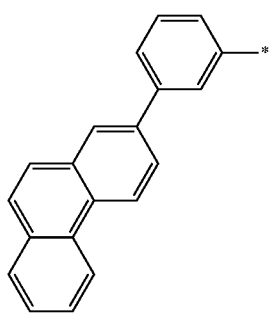
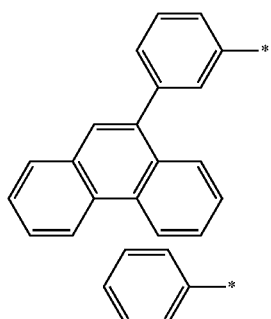
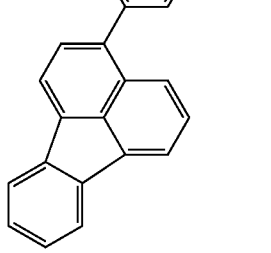
[Substituent group β1]
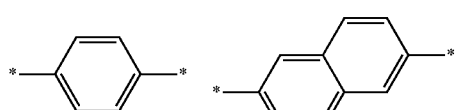
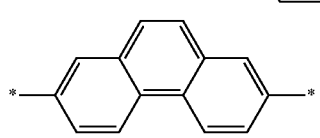
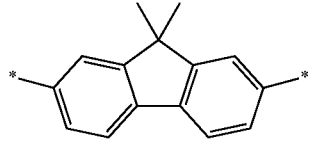
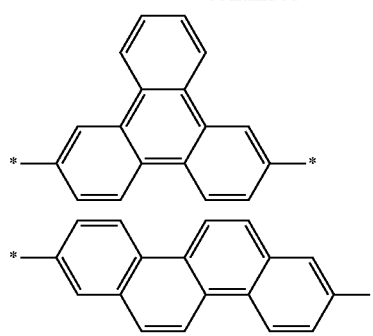
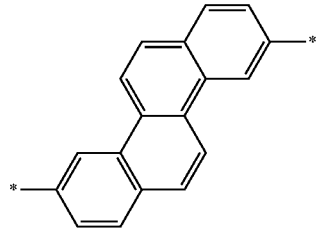
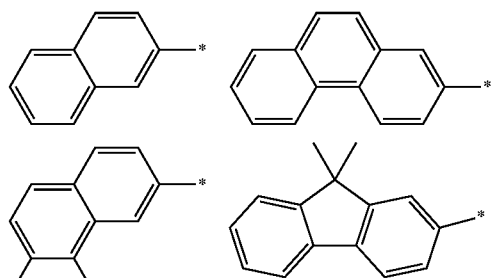
[Substituent group γ1]
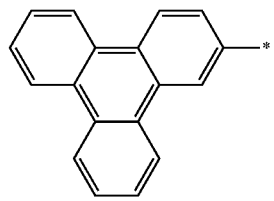
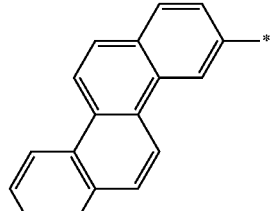
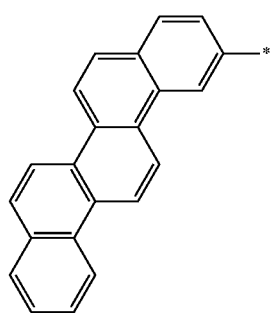

-continued

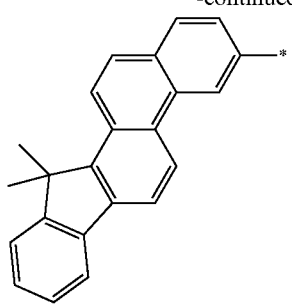

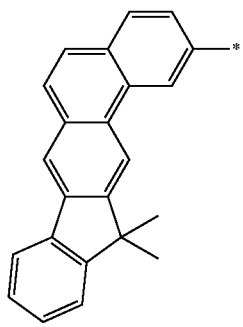
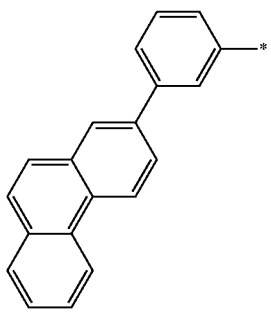

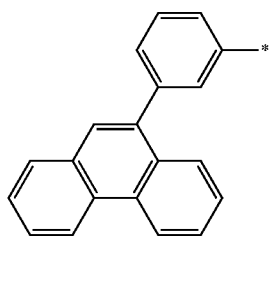
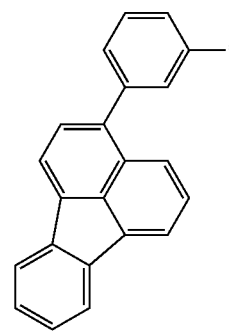

* represents a bonding hand with an adjacent substituent.

13. The organic light-emitting element according to claim 12, wherein the $Ar_1$ and the $Ar_4$ represent substituents that are not identical to each other.

14. The organic light-emitting element according to claim 12, wherein the $Ar_1$ represents a substituent selected from the following substituent group α2;

the $Ar_2$ and the $Ar_3$ each represent a substituent selected from the following substituent group β2; and the $Ar_4$ represents a substituent selected from the following substituent group γ2:

[Substituent group α2]

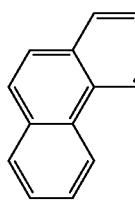
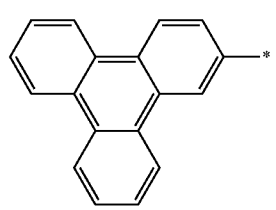

-continued

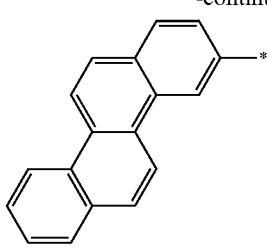

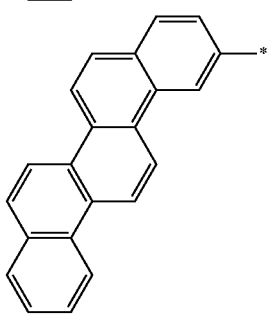

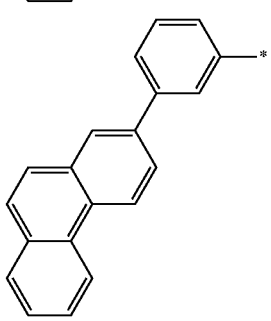

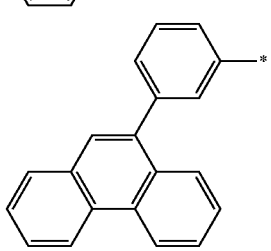

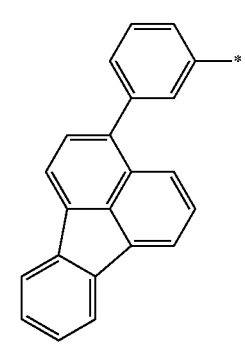

[Substituent group β2]

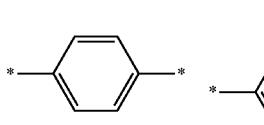

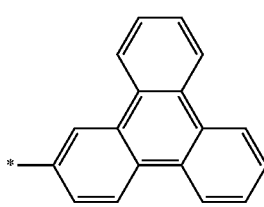

-continued

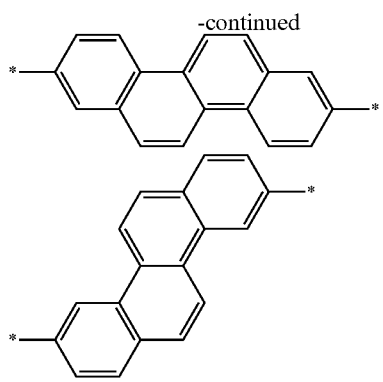

[Substituent group γ2]

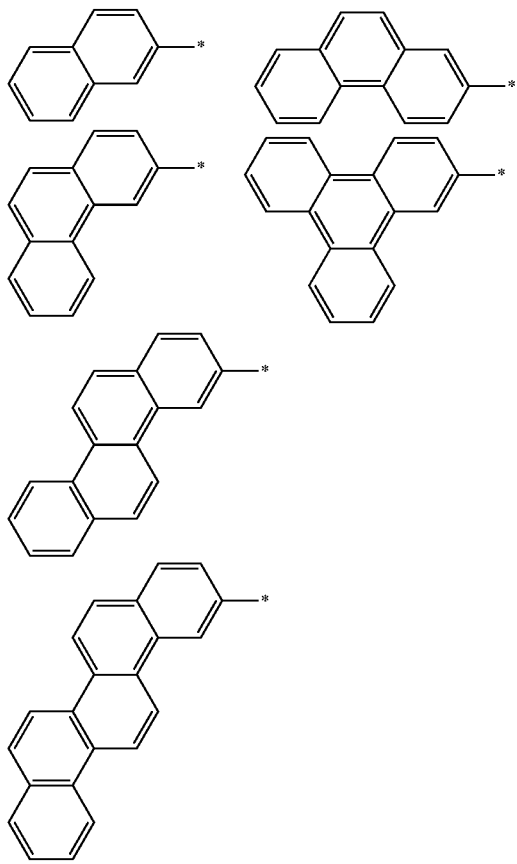

-continued

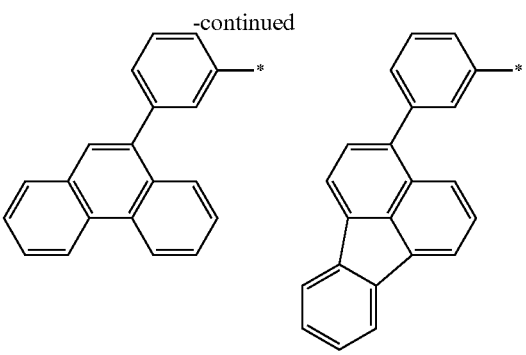

* represents a bonding hand with an adjacent substituent.

15. The organic light-emitting element according to claim 14, wherein the $Ar_1$ and the $Ar_4$ represent substituents that are not identical to each other.

16. The organic light-emitting element according to claim 10, wherein the emission layer includes the iridium complex, the aromatic hydrocarbon compound, and a third component; and
wherein the third component is a material having at least one of the features (a), (b), and (c):
(a) a material having a larger HOMO level that the HOMO level of the host;
(b) a material having a LUMO level smaller in energy than the LUMO level of the host; and
(c) a material having a HOMO level large in energy than the HOMO level of the host and having a LUMO level smaller in energy than the LUMO level of the host.

17. The organic light-emitting element according to claim 16, wherein a HOMO of the third component is higher than an HOMO of the hydrocarbon compound.

18. The organic light-emitting element according to claim 16, wherein a LUMO of the third component is higher than an LUMO of the hydrocarbon compound.

19. A display apparatus comprising multiple pixels, wherein the pixels each comprise the organic light-emitting element according to claim 10 and a transistor connected to the organic light-emitting element.

20. The display apparatus according to claim 19, wherein an electrode of the transistor is formed of a transparent oxide semiconductor.

21. The display apparatus according to claim 19, further comprising a color filter.

22. A display apparatus, which is formed by laminating the organic light-emitting element according to claim 10 to thereby output white light as a whole.

23. A lighting apparatus comprising:
the organic light-emitting element according to claim 10; and
an inverter circuit connected to the organic light-emitting element.

* * * * *